US010961565B2

(12) United States Patent
Fu et al.

(10) Patent No.: US 10,961,565 B2
(45) Date of Patent: Mar. 30, 2021

(54) DNA LOGIC-GATED PROXIMITY ASSEMBLY CIRCUIT FOR BIOCHEMICAL SENSING

(71) Applicant: Rutgers, The State University of New Jersey, New Brunswick, NJ (US)

(72) Inventors: Jinglin Fu, Cherry Hill, NJ (US); Sung Won Oh, Cherry Hill, NJ (US); Adriana Rosa Pereira, Riverside, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/361,794

(22) Filed: Mar. 22, 2019

(65) Prior Publication Data

US 2019/0292580 A1 Sep. 26, 2019

Related U.S. Application Data

(60) Provisional application No. 62/647,014, filed on Mar. 23, 2018.

(51) Int. Cl.
*C12Q 1/682* (2018.01)
*C12Q 1/6825* (2018.01)
*C12Q 1/6823* (2018.01)

(52) U.S. Cl.
CPC .......... *C12Q 1/682* (2013.01); *C12Q 1/6823* (2013.01); *C12Q 1/6825* (2013.01)

(58) Field of Classification Search
CPC .............................. C12Q 1/682; C12Q 1/6897
See application file for complete search history.

(56) References Cited

U.S. PATENT DOCUMENTS 7,115,369 B2 10/2006 Nilsen-Hamilton
8,071,734 B2 12/2011 Stanton et al.
8,552,167 B2 10/2013 Chang et al.
8,883,994 B2 11/2014 Wang et al.

OTHER PUBLICATIONS

Ahern, Biochemical, Reagents Kits Offer Scientists Good Return on Investment, 1995, 9, pp. 1-7. (Year: 1995).*
Liu et al, An oligonucleotide microchip for genome-wide microRNA profiling in human and mouse tissues, 2004, PNAS, 101, 9740-9744. (Year: 2004).*
Evanko, D., “Hybridization chain reaction,” *Nat. Methods* 1:186-187, 2004.
Jiang et al., “Real-Time Detection of Isothermal Amplification Reactions with Thermostable Catalytic Hairpin Assembly,” *J Am Chem Soc.* 135:7430-3, 2013.
Fu et al., “Multi-enzyme complexes on DNA scaffolds capable of substrate channeling with an artificial swinging arm,” *Nat Nanotechnol.* 9:531-6, 2014.
Liu et al., “A DNA tweezer actuated enzyme nanoreactor,” *Nat Commun.* 4:2127, 2013.
Oh et al., “Logic- Gated Catalytic Circuits for Sensing Bio-Targets,” Poster presented at 14th Annual Conference on Foundations of Nanoscience: Self-Assembled Architectures and Devices (FNANO17), Snowbird, Utah, Apr. 13, 2017.
Oh et al., “DNA-Mediated Proximity-Based Assembly Circuit for Actuation of Biochemical Reactions,” *Angew. Chem. Int. Ed.* 57:13086-13090, 2018.

* cited by examiner

*Primary Examiner* — Narayan K Bhat
(74) *Attorney, Agent, or Firm* — Klarquist Sparkman, LLP

(57) ABSTRACT

Provided are nucleic acid-based sensors, kits that include such sensors, and methods for making and using such sensors. The sensors permit detection of a broad array of target agents, such as nucleic acids (e.g., DNA and RNA), proteins, cells, and small molecules (e.g., toxins and metals). In some examples, the sensors determine the activity of a protein, such as an enzyme's activity. The assays provide easy-to-read signals for point-of-care diagnosis. The sensors control the conformational switch for recognizing targets and to trigger the subsequent assembly of enzyme/cofactor structures for producing and amplifying signals.

21 Claims, 27 Drawing Sheets
(18 of 27 Drawing Sheet(s) Filed in Color)

Specification includes a Sequence Listing.

FIG. 5A

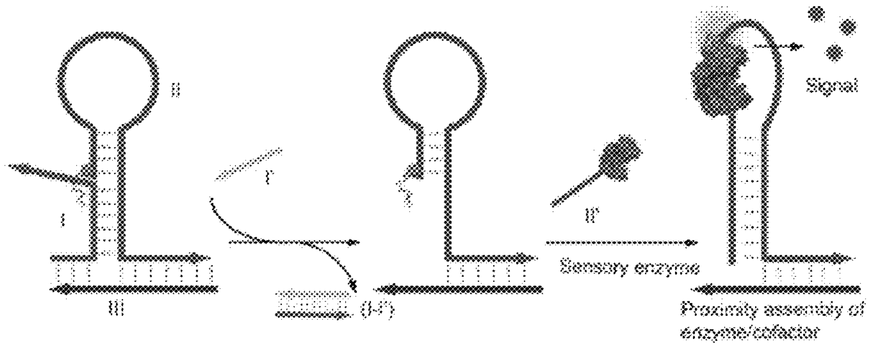

| Sample | DNA Sequence (SEQ ID NO: ) | Bases |
|---|---|---|
| Hairpin-II | 5'-/5AmMC6/ACC AGC CGT TTT TTC GGC TGG TGA CGG CTC CTT GGC GCC GGC TTT C (1) | 46 |
| Toehold-I | 5'-GTG CGA ATT GGA GCC GTC GTT GGT GTG C (2) | 28 |
| Base-III | 5'-TTT AGA AAG CCG GCG CCT TCG CAC TTT (3) | 27 |
| Trigger-I' | 5'-GCA CAC CAA CGA CGG CTC C (4) | 19 |
| Enzyme-DNA II' | 5'-AGC CGT CAC CAG CCG TTT TT/3AmMO/ (5) | 20 |
| G-halve-hairpin | 5'-TGG GTA GGG CGG GTT TTC CTA CCC ACC TTG TCA TAG AGC AC (6) | 41 |
| G-halve-II' | 5'-GTG CTC TAT GAC AAG GAC CCA TGG GTA GGT TTT GGG TCC TTG TCA (7) | 45 |
| Compliment ary of II' | 5'-AA AAA CGG CTG GTG ACG GCT (8) | 20 |

FIG. 5B

| Sample | DNA Sequence (SEQ ID NO: ) | Bases |
|---|---|---|
| Hairpin-II | 5'-/5AmMC6/ACC AGC CGT TTT TTC GGC TGG TGA CTG ATG TTG ATT GGC GCC GGC TTT C (9) | 49 |
| Toehold-I | 5'-GTG CGA ATT TCA ACA TCA GTC TGA TAA GCT A (10) | 31 |
| Base-III | 5'-TTT AGA AAG CCG GCG CCT TCG CAC TTT (3) | 27 |
| miR-21 | 5'-rUAG CrUrU ArUC AGA CrUG ArUG rUrUG A (11) | 22 |
| Enzyme-DNA II' | AAC ATC AGT CAC CAG CCG TTTTT /3AmMO/ (12) | 23 |

FIG. 5C

| Sample | DNA Sequence (SEQ ID NO: ) | Bases |
|---|---|---|
| Hairpin-II | 5'-/5AmMC6/ACC AGC CGT TTT TTC GGC TGG TCC CAG GTT CTC TTG GCG CCG GCT TTC (13) | 48 |
| Adenosine Aptamer | 5'-GTG CGA ATT GAG AAC CTG GGG GAG TAT TGC GGA GGA AGG T (14) | 40 |
| Enzyme-DNA II' | 5'-GAG AAC CTG GGA CCA GCC GTT TTT/3AmMO/ (15) | 24 |
| Base-III | 5'-TTT AGA AAG CCG GCG CCT TCG CAC TTT (3) | 27 |

FIG. 5D

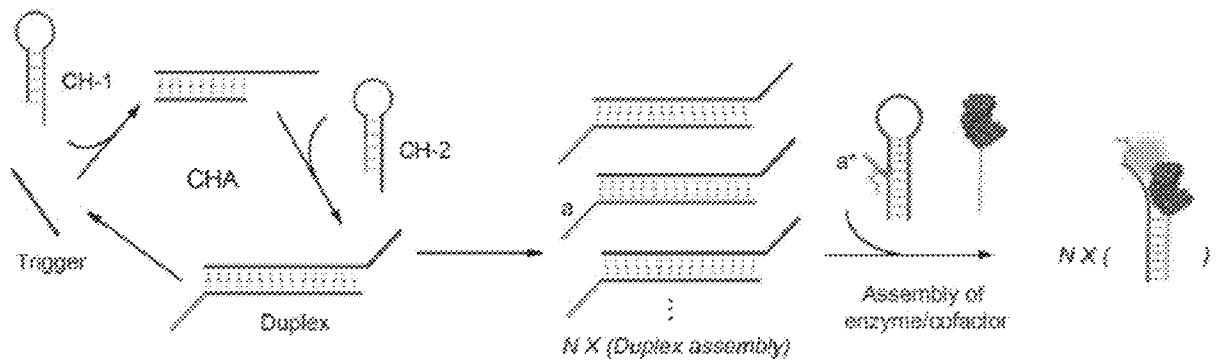

| Sample | DNA Sequence (SEQ ID NO: ) | Bases |
|---|---|---|
| CH-1 | 5'-AGA GGC ATC AAT GGG AAT GGG ATC ATG CCT CTA ACC TAG CGA TCC CAT TCC CAT TG (16) | 56 |
| CH-2 | 5'-ATG GGA TCG CTA GGT TAG AGG CAT GAT CCC ATT CCC AAA CAT GCC TCT AAC CTA GCC CTT GTC ATA GAG CAC (17) | 72 |
| Trigger | 5'-GAT CCC ATT CCC ATT GAT GCC TCT (18) | 24 |
| Hairpin-cofactor | 5'-/5AmMC6/TAC CAG CCG TTT TTT TTC GGC TGG TCC TTG TCA TAG AGC AC (19) | 41 |
| Toehold a* | 5'-GTG CTC TAT GAC AAG GGC TAG GTT (20) | 24 |
| Enzyme-DNA | 5'-TGA CAA GGA CCA GCT TTT T/3AmMO/ (21) | 19 |

FIG. 5E

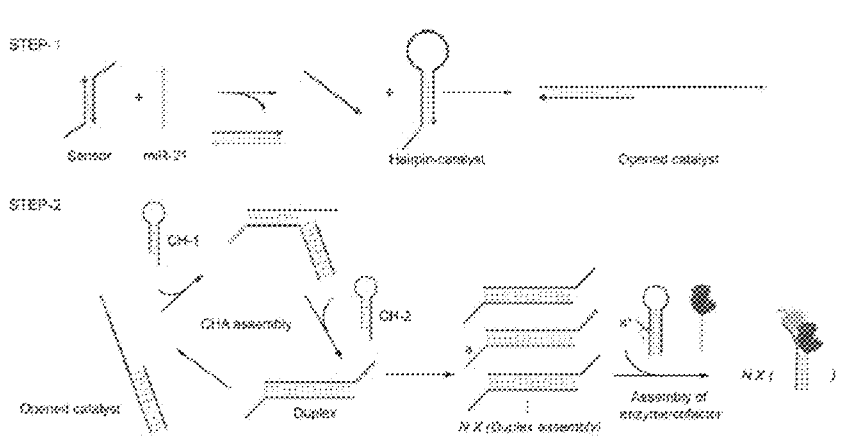

| Sample | DNA Sequence (SEQ ID NO: ) | Bases |
|---|---|---|
| Sensor (purple strand) | 5'-ATG CCT CTT AGC TTA TCA GAC T (22) | 22 |
| Sensor (red strand) | 5'-TCA ACA TCA GTC TGA TAA GCT A (23) | 22 |
| miR-21 | 5'-rUAG CrUrU ArUC AGA CrUG ArUG rUrUG A (11) | 22 |
| Hairpin-locked catalyst | 5'-AGT CTG ATA AGC TAA GAG GCA TGA TCC CAT TCC CAT TGA TGC CTC TTA GCT T (24) | 52 |
| CH-1 | 5'-AGA GGC ATC AAT GGG AAT GGG ATC ATG CCT CTA ACC TAG CGA TCC CAT TCC CAT TG (16) | 56 |
| CH-2 | 5'-ATG GGA TCG CTA GGT TAG AGG CAT GAT CCC ATT CCC AAA CAT GCC TCT AAC CTA GCC CTT GTC ATA GAG CAC (17) | 72 |
| Hairpin-cofactor | 5'-/5AmMC6/TAC CAG CCG TTT TTT TTC GGC TGG TCC TTG TCA TAG AGC AC (19) | 41 |
| Toehold a* | 5'-GTG CTC TAT GAC AAG GGC TAG GTT (20) | 24 |
| Enzyme-DNA | 5'-TGA CAA GGA CCA GCT TTT T/3AmMO/ (21) | 19 |

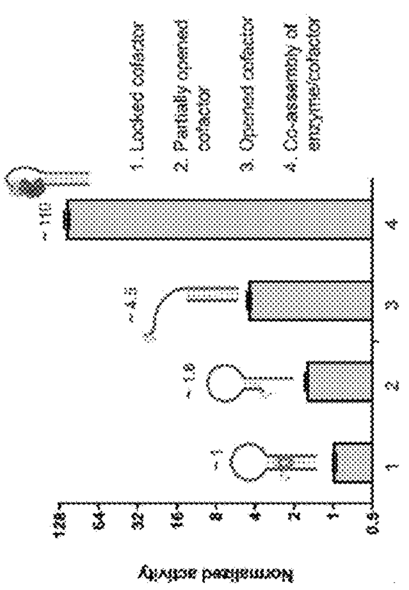
FIG. 6B
FIG. 6A
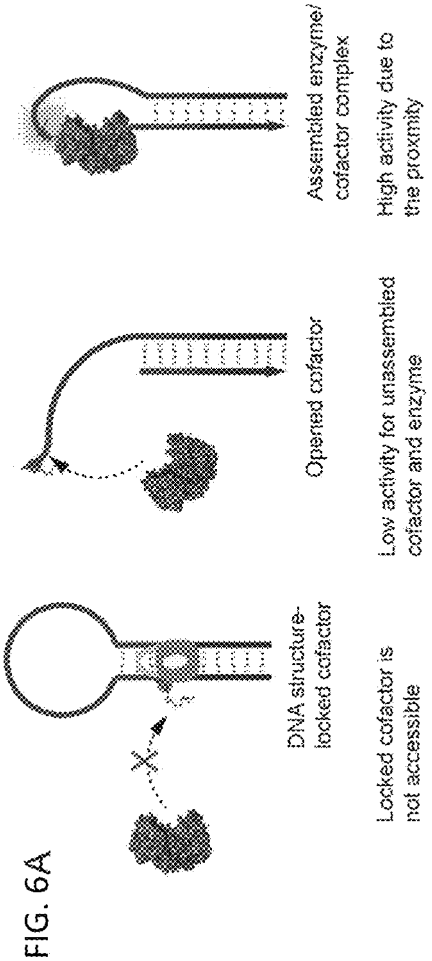
FIG. 6C
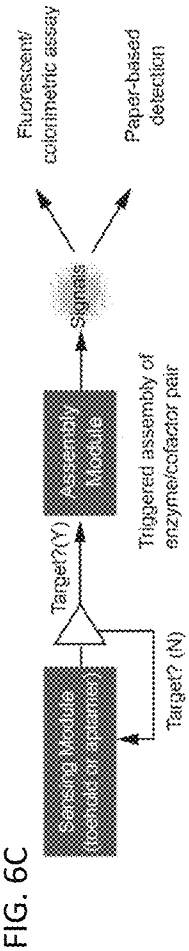

glucose-6-phosphate
6-phosphogluconolactone
resorufin (pink)
resazurin (blue)

DNA LOGIC-GATED PROXIMITY ASSEMBLY CIRCUIT FOR BIOCHEMICAL SENSING

CROSS-REFERENCE TO RELATED APPLICATION

This application claims the benefit of U.S. Provisional Application No. 62/647,014, filed Mar. 23, 2018. The provisional application is herein incorporated by reference in its entirety.

ACKNOWLEDGMENT OF GOVERNMENT SUPPORT

This invention was made with government support under W911NF-14-1-0434 awarded by the Army Research Office. The government has certain rights in the invention.

FIELD

This application relates to nucleic acid-based sensors, kits that include such sensors, and methods for making and using such sensors. The sensors permit detection of a broad array of target agents, such as nucleic acids (e.g., DNA and RNA), proteins, cells, and small molecules (e.g., toxins and metals).

BACKGROUND

Point-of Care (POC) testing includes assays that are simply operated, easy-to-read, rapid, and low-cost, which can be used by non-specialists at home, in the wild field, or on an ambulance. POC testing provides timely diagnostic results, which enables early diagnosis of diseases, protective therapy, and rapid treatment of the patients. Examples include glucose meters and pregnancy strips.

SUMMARY

Provided herein are sensors, which in includes (a) a trigger module and (b) a sensory module. In one example the trigger module of the sensor can include at least two nucleic acid molecules, wherein the first nucleic acid molecule includes a first portion specific for a target, a second portion, and a third portion, and the second nucleic acid molecule includes a terminal cofactor, a first stem portion, a loop portion, a second stem portion, a third stem portion, and a fourth portion. The first stem portion can include the terminal cofactor and is complementary to the second stem portion, thereby resulting in hybridization between the first stem portion and the second stem portion, thereby producing the loop portion. The third stem portion is complementary to the second portion of the first nucleic acid molecule, thereby resulting in hybridization between the third stem portion and the second portion of the first nucleic acid molecule. The trigger module can optionally include a third nucleic acid molecule (and in some examples includes the third nucleic acid molecule. Such a third nucleic acid molecule if included includes a first portion and a second portion, wherein the first portion of the third nucleic acid molecule is complementary to the third portion of the first nucleic acid molecule thereby resulting in hybridization between the first portion of the third nucleic acid molecule and the third portion of the first nucleic acid molecule, wherein the second portion of the third nucleic acid molecule is complementary to the fourth portion of the second nucleic acid molecule thereby resulting in hybridization between the second portion of the third nucleic acid molecule and the fourth portion of the second nucleic acid molecule, and wherein hybridization between nucleotides of the first and second nucleic acid molecules, first and third nucleic acid molecules, and second and third nucleic acid molecules, forms the trigger module.

The sensory module of the sensor can include a fourth nucleic acid molecule comprising a nucleic acid strand and an enzyme, wherein the nucleic acid strand of the fourth nucleic acid molecule is complementary to the second and third stem portion of the second nucleic acid molecule, and wherein the enzyme is activated by the cofactor.

In another example, the trigger module of the sensor includes (i) a first nucleic acid molecule, comprising a first portion specific for a target and a second portion, (ii) a second nucleic acid molecule comprising a terminal cofactor, a first stem portion, a loop portion, a second stem portion, and a third stem portion, wherein the first stem portion includes the terminal cofactor and is complementary to the second stem portion, thereby resulting in hybridization between the first stem portion and the second stem portion, thereby producing the loop portion, wherein the third stem portion is complementary to the second portion of the first nucleic acid molecule, thereby resulting in hybridization between the third stem portion and the second portion of the first nucleic acid molecule, wherein hybridization between nucleotides of the first and second nucleic acid molecules, forms the trigger module. The sensory module of such a sensor can include a third nucleic acid molecule comprising a nucleic acid strand and an enzyme, wherein the nucleic acid strand of the third nucleic acid molecule is complementary to the second and third stem portion of the second nucleic acid molecule, and wherein the enzyme is activated by the cofactor.

In one example, a sensor includes a sensory module and a trigger module. In some examples the sensory module includes a first nucleic acid molecule comprising a nucleic acid strand and a terminal enzyme, for example at or near a 3'-end of the nucleic acid strand. In some examples the trigger module includes a second nucleic acid molecule having a loop or linker portion (for example at a 5'end) and an aptamer portion (for example at al 3'-end). The trigger module also includes an inhibitor of the enzyme, for example at or near the 5'-end of the second nucleic acid molecule. At least a portion of the aptamer portion shares complementary to the first nucleic acid molecule, resulting in hybridization between the first nucleic acid molecule of the sensor module and the aptamer portion of the trigger module. This brings the inhibitor of the enzyme and the enzyme into proximity such that the inhibitor of the enzyme inhibits the enzyme.

Also provided are kits and compositions that include a disclosed sensor, as well as methods of using a disclosed sensor to detect one or more targets, for example in a sample. Also provided are methods of using a disclosed sensor to determine the activity of a protein.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A-5E show sequences used in the exemplary sensors. Sequences for sensor shown in (A) FIG. 9A (SEQ ID NOS: 1-8), (B) DNA toehold-displacement circuit for detecting miRNA-21 in FIG. 13B (SEQ ID NOS: 9-10, 3, 11-12), (C) aptamer switch circuit for detecting adenosine in FIG. 13E (SEQ ID NOS: 13-15, 3), (D) CHA circuit-mediated assembly of enzyme/cofactor pairs in FIG. 14B (SEQ ID NOS: 16-21), and (E) miR-2 detection using CHA assembly circuit in FIG. 15A (SEQ ID NOS: 22, 23, 11, 24, 16, 17, 19, 20, 21).

FIGS. 6A-6C provide the design of DNA-mediated proximity assembly of an enzyme/cofactor pair. (A) The design rationale is based on a DNA hairpin-locked cofactor. (B) The enzyme/cofactor activities on different DNA hairpin structures: 1) hairpin-locked cofactor, 2) partially opened hairpin, 3) opened hairpin with exposed cofactor, 4) proximity assembly of an enzyme/cofactor pair. The assay was monitored for one hour. Error bars represent three replicates. (C) A design chart of a biochemical sensing with the integration of DNA structural switches (sensing module) with the triggered assembly of an enzyme/cofactor pair (signal production).

The schematic drawings are not necessarily to scale.

SEQUENCE LISTING

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing generated on Mar. 17, 2019 (8 kb) and submitted herewith is herein incorporated by reference.

Figure 9B:
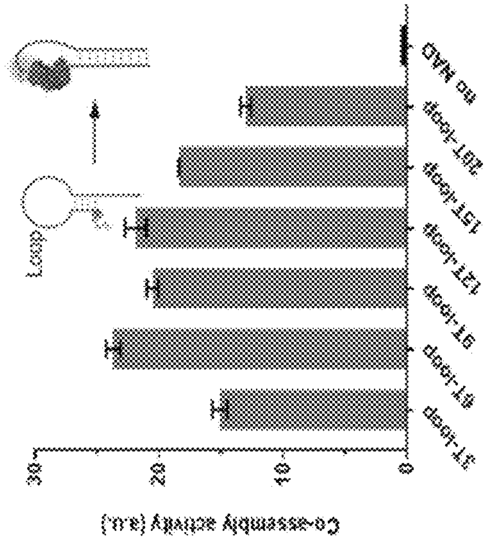
FIGS. 9A-9B: DNA logic-gated assembly of biochemical reactions. (A) A DNA "AND" gated mediation of an enzyme/cofactor pair. (B) Optimization of the hairpin loop length for maximizing the activity performance of the assembled enzyme/cofactor pairs. The assay was monitored for one hour.
Figure 9A:
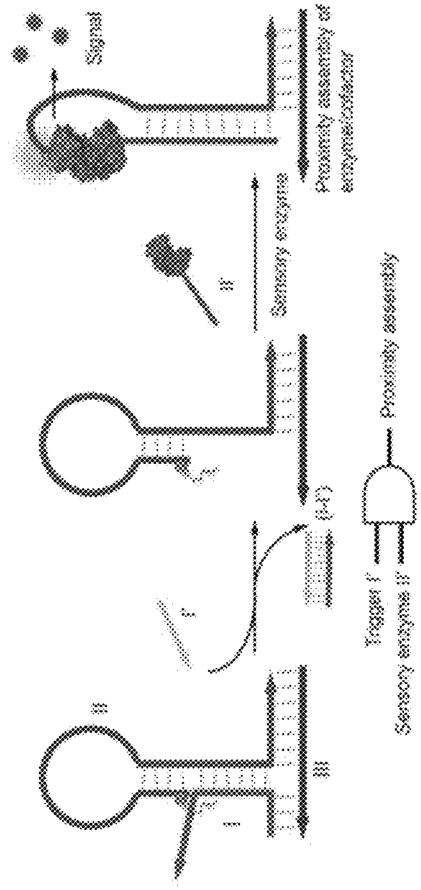

SEQ ID NO: 1 is the sequence of hairpin II in FIG. 9A.

SEQ ID NO: 2 is the sequence of toehold I in FIG. 9A.

Figure 13A:
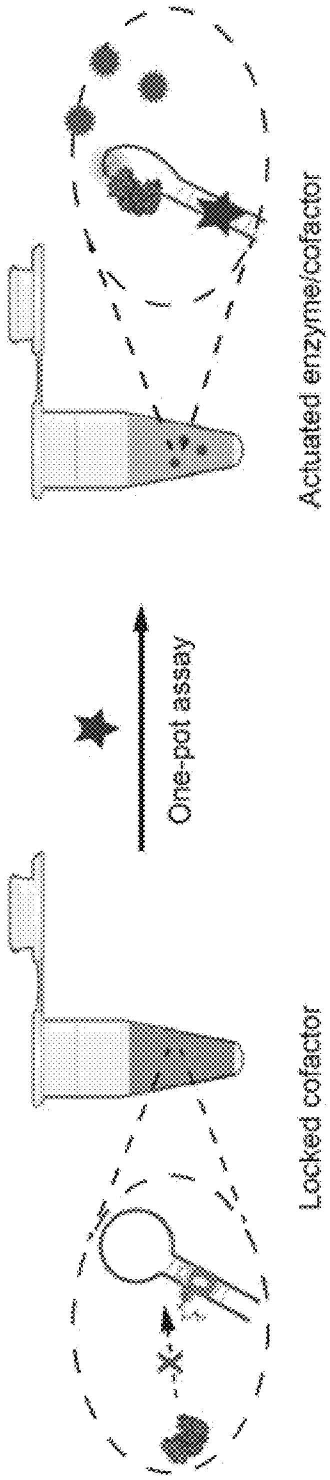
FIGS. 13A-13G. The detection of bio-targets with DNA-mediated assembly circuit. (A) One-pot assay of bio-targets with the actuated enzyme reaction. (B) A DNA hairpin with the toehold displacement for detecting hsa-miR-21. (C) The actuation of G6PDH/NAD+ reactions depending on the addition of hsa-miR-21 from 0 to 64 nM, and (D) the activities of G6PDH/NAD+ pairs depending on the addition of miRNA. The activities are normalized to the reaction of 64 nM miR-21. (E) An aptamer-locked hairpin for detecting adenosine, (F) the actuation of G6PDH/NAD+ reactions depending on the addition of adenosine from 0 to 320 μM, and (G) the activities of G6PDH/NAD+ pairs depending on the addition of adenosine. The activities are normalized to the reaction of 0.32 mM adenosine. The concentrations of DNA hairpin-locked cofactors and enzymes are 100 nM. The apparent dissociation constant (Kd) of aptamer-locked sensor is ~24±4 μM. Error bar: range of data from three replicates. Sequences shown in FIG. 13B are provided in SEQ ID NOS: 9-10, 3, 11-12 and sequences shown in FIG. 13E are provided in SEQ ID NOS: 13, 14, 15, and 3.
Figure 13B:
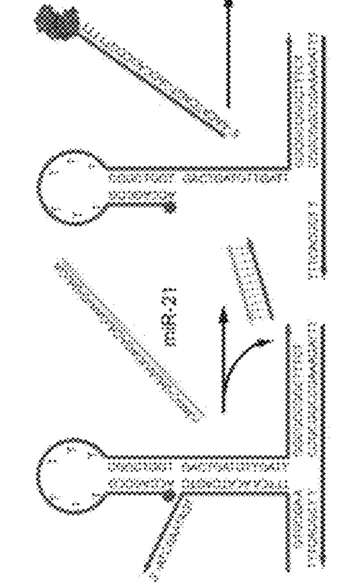

SEQ ID NO: 3 is the sequence of base III in FIGS. 9A and 13B.

SEQ ID NO: 4 is the sequence of trigger-I' in FIG. 9A.

SEQ ID NO: 5 is the sequence of enzyme DNA II' in FIG. 9A.

SEQ ID NO: 6 is the sequence of G-halve-hairpin in FIG. 9A.

SEQ ID NO: 7 is the sequence of G-halve-II' in FIG. 9A.

SEQ ID NO: 8 is the sequence of complimentary of II' in FIG. 9A.

SEQ ID NO: 9 is the sequence of hairpin II in FIG. 13B.

SEQ ID NO: 10 is the sequence of toehold I in FIG. 13B.

SEQ ID NO: 11 is the sequence of miR-21.

SEQ ID NO: 12 is the sequence of enzyme DNA II' in FIG. 13B.

Figure 13C:
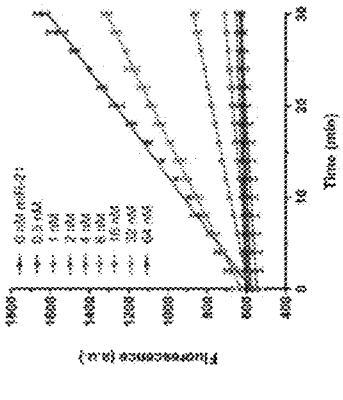
Figure 13D:
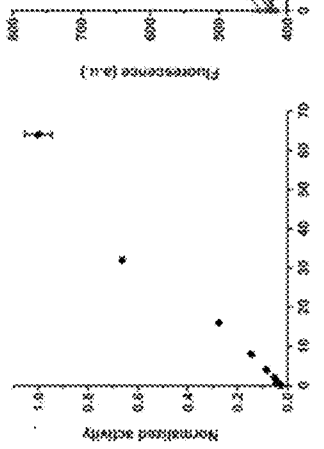
Figure 13E:
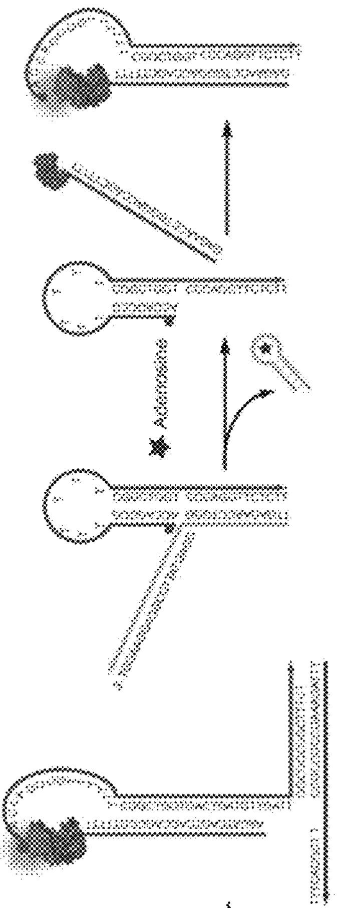

SEQ ID NO: 13 is the sequence of hairpin II in FIG. 13E.

SEQ ID NO: 14 is the sequence of adenosine aptamer.

SEQ ID NO: 15 is the sequence of enzyme DNA II' in FIG. 13E.

Figures 14A, 14B, 14C, 14D:
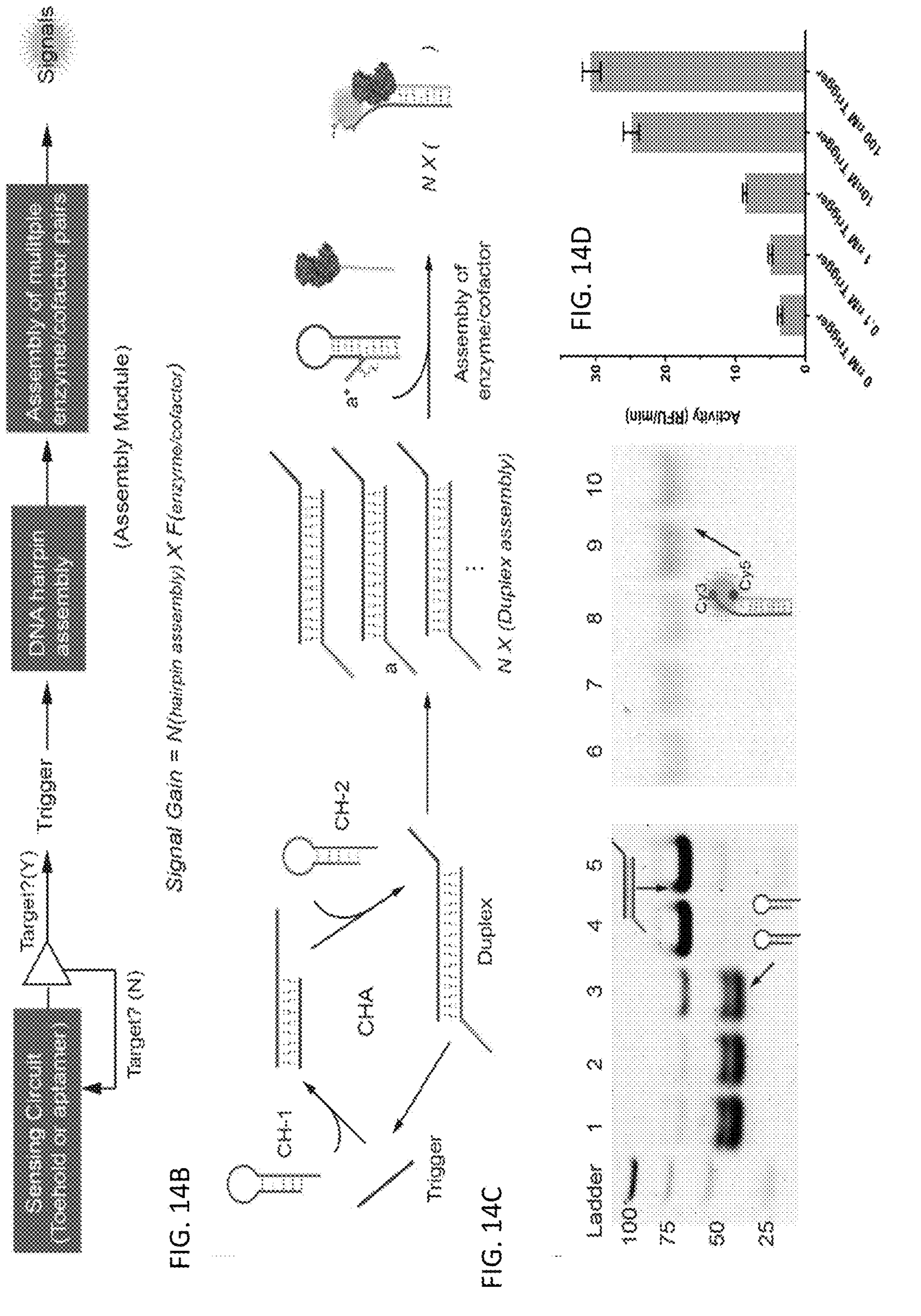
FIGS. 14A-14D. The DNA hairpin assembly-mediated actuation of enzyme/cofactor pairs for increasing the detection sensitivity. (A) The design concept of using DNA hairpin assembly to assemble multiple enzyme/cofactor pairs with one trigger molecule. (B) The CHA is used to produce short DNA duplexes for assembling multiple G6PDH/NAD+ pairs: T, trigger strand. (C) Left panel: Native PAGE for characterizing the CHA production of duplexes. Lane 1: 100 nM mixture of CH-1 and CH-2 hairpins; Lane 2-5: 100 nM mixture of CH-1 and CH-2 with the addition of 0.1 nM (lane 2), 1 nM (lane 3), 10 nM (land 4) and 100 nM (lane 5) trigger strands. Right panel (lane 6-10): Cy3-Cy5 fluorescence gel for the product of lane 1-5 incubating with 100 nM DNA hairpin-locked NAD+(Cy3 label) and G6PDH strand (Cy5 label). (D) The G6PDH/NAD+ activities depending on the addition of trigger strands from 0-100 nM. Error bar: range of data from three replicates.
Figure 15A:
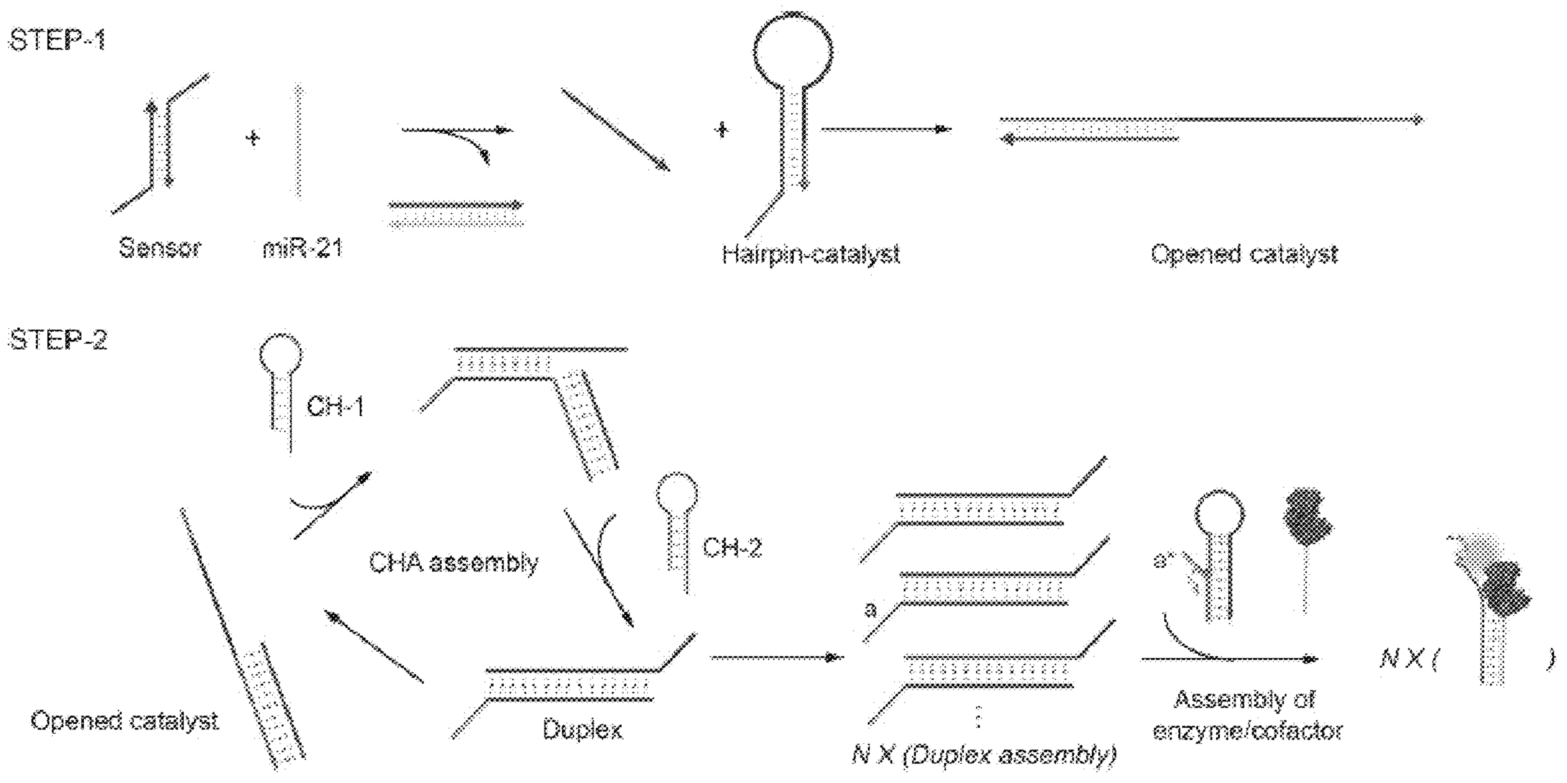
FIG. 15A. The design scheme of a two-step assay for miR-21 detection using a CHA circuit mediated assembly of enzyme/cofactor pairs. In Step-1, a sensor structure first recognizes a miR-21 strand and releases a trigger strand (purple) by strand displacement. The trigger strand subsequently opens a hairpin-locked catalyst strand. In Step-2, the opened catalyst strand catalyzes the CHA assembly of hairpin 1 (CH-1) and hairpin-2 (CH-2), with the production of short duplexes. The duplexes can assemble together an enzyme and a cofactor with the activated enzyme reaction.

SEQ ID NO: 16 is CH-1 in FIGS. 14B and 15A.

SEQ ID NO: 17 is CH-2 in FIGS. 14B and 15A.

SEQ ID NO: 18 is the trigger sequence in FIG. 14B.

SEQ ID NO: 19 is the sequence of hairpin-cofactor in FIGS. 14B and 15A.

SEQ ID NO: 20 is the sequence of toehold a* in FIGS. 14B and 15A.

SEQ ID NO: 21 is the sequence enzyme-DNA in FIGS. 14B and 15A.

SEQ ID NO: 22 is the sequence of the sensor (purple) in FIG. 15A.

SEQ ID NO: 23 is the sequence of the sensor (red) in FIG. 15A.

SEQ ID NO: 24 is the sequence of the hairpin-locked catalyst in FIG. 15A.

SEQ ID NO: 25 is the sequence of miR-141.

SEQ ID NO: 26 is the sequence of miR-375.

SEQ ID NO: 27 is the sequence of a SNV EGFR-L858R.

SEQ ID NO: 28 is the sequence of the nucleic acid strand comprising an adenosine aptamer and a 5'-AppNHP in FIG. 16.

SEQ ID NO: 29 is the sequence of the nucleic acid strand comprising an enzyme (HEK) in FIG. 16.

DETAILED DESCRIPTION

Unless otherwise explained, all technical and scientific terms used herein have the same meaning as commonly understood by one of ordinary skill in the art to which a disclosure belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods are described in various general and more specific references, including, for example, Sambrook et al., *Molecular Cloning: A Laboratory Manual,* 2nd ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology,* 4th ed., *Wiley & Sons,* 1999; Harlow and Lane, *Antibodies: A Laboratory Manual*, Cold Spring Harbor Laboratory Press, 1990; and *Harlow and Lane, Using Antibodies: A Laboratory Manual*, Cold Spring Harbor Laboratory Press, 1999.

All publications, patent applications, patents, and other references mentioned herein are incorporated by reference in their entirety for all purposes. All sequences associated with the GenBank® Accession numbers provided herein are incorporated by reference in their entirety as were present on Mar. 23, 2018.

In order to facilitate review of the various embodiments of the disclosure, the following explanations of specific terms are provided:

Binding: An association between two substances or molecules, such as the hybridization of one nucleic acid molecule to another (or itself), the association of an antibody with a peptide, the association of a protein with another protein, molecule, or with a nucleic acid molecule, or the association between a hapten and an antibody. Binding can be detected by any procedure known to one skilled in the art, for example using the methods provided herein. In one example binding occurs between an enzyme and an enzyme inhibitor.

One molecule is said to "specifically bind" to another molecule when a particular agent (e.g., a "specific binding agent") can specifically react with a particular analyte, for example to specifically immunoreact with an antibody, or to specifically bind to a particular target agent. The binding is a non-random binding reaction, for example between an antibody molecule and an antigenic determinant or between one oligonucleotide (such as a functional nucleic acid) and a target agent (such as DNA or RNA). Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody". An oligonucleotide molecule binds or stably binds to a target nucleic acid molecule if a sufficient amount of the oligonucleotide molecule forms base pairs or is hybridized to its target nucleic acid molecule, to permit detection of that binding.

In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using known methods.

Co-factor: A non-protein chemical compound or metallic ion required for an enzyme's activity. Cofactors assist in biochemical transformations. Cofactors can be inorganic ions (such as Mg2+, Cu+, Mn2+, cupric, nickel, zinc, molybdenum, and iron) or organic molecules (which are typically less than 1000 Da) (e.g., flavin, heme, nicotinamide adenine dinucleotide, and adenosine (di)triphosphate). Exemplary co-factors and their corresponding enzymes are shown in Table 1, and can be part of a sensor provided herein (e.g., co-factor 160 of FIGS. 1A, 1C, 1E 260 of FIGS. 1B, 1C, 1H, 2, 3). Such co-factors and enzymes can be used in the sensors provided herein.

TABLE 1

Exemplary co-factors and corresponding enzymes

| Co-Factor | Enzyme |
|---|---|
| Cu+ | Cytochrome oxidase |
| Ferrous or Ferric | Catalase |
| | Cytochrome |
| | Nitrogenase |
| | hydrogenase |
| Mg2+ | Glucose 6-phosphase |
| | Hexokinase |
| | DNA polymerase |

TABLE 1-continued

| Exemplary co-factors and corresponding enzymes | |
|---|---|
| Co-Factor | Enzyme |
| Mn2+ | Arginase |
| Molybdenum | Nitrate reductase<br>Nitrogenase |
| Nickel | urease |
| Zinc | Alcohol dehydrogenase<br>Carbonic anhydrase<br>DNA polymerase |
| Thiamine pyrophosphate | Pyruvate dehydrogeanse |
| NAD+ and NADP+ | Most dehydrogenase,<br>such as glucose-6-phosphate<br>dehydrogenase, lactate<br>dehydrogenase |
| Pyridoxal phosphate | aminotransferease |
| Methylcobalamin | vitamin B12-dependent<br>enzymes, e.g.<br>Methionine synthase |
| Cobalamine | Methyltransferase |
| Biotin | Streptavidin-fused enzyme |
| Coenzyme A | Pyruvate dehydrogenase |
| Tetrahydrofolic acid | Dihydrofolate reductase |
| Menaquinone | γ-glutamyl carboxylase |
| Ascorbic acid | Ascorbate peroxidase |
| Flavin adenine dinucleotide | Glucose oxidase, glucose<br>dehydrogenase |
| Flavin mononucleotide | diaphorase |
| Coenzyme F420 | Coenzyme F420 hydrogenase |
| Adenosine triphosphate | Hexokinase, pyruvate<br>kinase, acetate kinase; |
| S-Adenosyl methionine | Radical SAM enzymes |
| Coenzyme B | enzyme methyl coenzyme<br>M reductase |
| Coenzyme M | enzyme methyl-coenzyme<br>M reductase, |
| Cytidine triphosphate | Aspartate carbamoyltransferase |
| Glutathione | Glutathione reductase |
| Heme | Horseradish peroxidase, DNA<br>G-quadruplex |
| Lipoamide | dihydrolipoyl transacetylase |
| Methanofuran | formyltransferase |
| Molybdopterin | xanthine oxidase,<br>DMSO reductase,<br>sulfite oxidase,<br>nitrate reductase |
| 3'-Phosphoadenosine-<br>5'-phosphosulfate | Adenylyl-sulfate kinase |
| Pyrroloquinoline quinone | Quinoprotein glucose<br>dehydrogenase |
| Tetrahydrobiopterin | Tryptophan hydroxylase |

Complementarity and percentage complementarity: Molecules with complementary nucleic acid molecules form a stable duplex or triplex when the strands bind (i.e., hybridize), to each other by forming Watson-Crick, Hoogsteen or reverse Hoogsteen base pairs. Stable binding occurs when an oligonucleotide molecule remains detectably bound to a target nucleic acid sequence under the required conditions. Since there is one complementary base for each base found in DNA/RNA (such as A/T, and C/G), the complementary strand for any single strand can be determined.

Complementarity is the degree to which bases in one nucleic acid strand base pair (such as a nucleic acid molecule obtained from a subject or a nucleic acid molecule that is part of a sensor provided herein) hybridize with the bases in a second nucleic acid strand (such as a nucleic acid molecule that is part of a sensor provided herein). In one example, complementarity is the degree to which bases in a nucleic acid molecule portion of a sensory module hybridize with the bases in an aptamer portion of a trigger module. Complementarity is described by percentage, that is, the proportion of nucleotides that form base pairs between two strands or within a specific region or domain of two strands. For example, if 10 nucleotides of a 15-nucleotide nucleic acid molecule form base pairs with a target nucleic acid molecule, that nucleic acid molecule is said to have 66.67% complementarity to the region of nucleic acid targeted.

In the present disclosure, "sufficient complementarity" means that a sufficient number of base pairs exist between a first nucleic acid molecule and a second nucleic acid molecule (such as a nucleic acid molecule of a sensor provided herein and a target nucleic acid sequence or a second nucleic acid molecule of a sensor provided herein) to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 80% complementarity, at least about 90% complementarity, at least about 95% complementarity, at least about 98% complementarity, or even at least about 100% complementarity.

A thorough treatment of the qualitative and quantitative considerations involved in establishing binding conditions that allow one to design appropriate oligonucleotides for use under the desired conditions is provided by Beltz et al. Methods Enzymol. 100:266-285, 1983, and by Sambrook et al. (ed.), Molecular Cloning: A Laboratory Manual, 2nd ed., vol. 1-3, Cold Spring Harbor Laboratory Press, Cold Spring Harbor, N.Y., 1989.

DNA: Deoxyribonucleic acid. A long chain polymer which includes the genetic material of most living organisms (some viruses have genes comprising ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed. The DNA molecules described herein can include naturally occurring or non-naturally occurring nucleotides.

Detect: To determine if a target agent is present or absent, and in some examples further includes quantification of the agent if detected, for example using the sensors provided herein. Thus, detection can be qualitative or quantitative. In some example, it is to determine an activity of a protein.

Hybridization: The ability of complementary single-stranded DNA, RNA, or DNA/RNA hybrids, to form a duplex molecule (e.g., ds DNA molecule). For example, the features (such as length, base composition, and degree of complementarity) that will enable a nucleic acid (e.g., a first nucleic acid molecule) to hybridize to another nucleic acid (e.g., a target DNA or RNA, or second nucleic acid molecule) under conditions of selected stringency, while minimizing non-specific hybridization to other substances or molecules can be determined based on the present disclosure. "Specifically hybridize" and "specifically complementary" are terms that indicate a sufficient degree of complementarity such that stable and specific binding occurs between a first nucleic acid molecule and a second nucleic acid molecule. The first and second nucleic acid molecules need not be 100% complementary to be specifically hybridizable (for example, at least 50%, at least 75%, at least 80%, at least 90%, at least 95%, at least 99%, or at least 99% may be sufficient). Specific hybridization is also referred to herein as "specific binding."

Hybridization conditions resulting in particular degrees of stringency will vary depending upon the nature of the hybridization method and the composition and length of the hybridizing nucleic acid sequences. Generally, the temperature of hybridization and the ionic strength (such as the $Na+$ concentration) of the hybridization buffer determines the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). Exemplary hybridization conditions include hybridization at about 37° C. or higher (such as about 37° C., 42° C., 50° C., 55° C., 60° C., 65° C., 70° C., 75° C., or higher, such as 45-55° C. or 48-52° C.). Among the hybridization reaction parameters which can be varied are salt concentration, buffer, pH, temperature, time of incubation, amount and type of denaturant such as formamide.

Immobilized: Bound to a surface, such as a solid support. In one embodiment, the solid surface is a bead. In one embodiment, the solid surface is a paper, such as a cellulose based paper, such as nitrocellulose. In some examples, a sensor of the present disclosure is immobilized to a support by simply applying the sensor in solution to the support, and allowing the solution to dry, thereby immobilizing the sensor to the support.

Inhibitor: An inhibitor of a protein, such as an enzyme inhibitor, is a molecule that binds to the protein and significantly decreases its activity, such as a reduction in the activity by at least 25%, at least 50%, at least 60%, at least 75%, at least 80%, at least 90%, at least 95%, or 100%, as compared to the activity of the protein in the absence of the inhibitor. The binding of an inhibitor can stop a substrate from entering an enzyme's active site and/or hinder the enzyme from catalyzing its reaction. Inhibitor binding can be reversible or irreversible. Exemplary inhibitors and their corresponding enzymes and co-factors are shown in Table 2. Such inhibitors, co-factors and enzymes can be used in the sensors provided herein.

TABLE 2

Exemplary Enzyme Inhibitors

| Enzyme | Cofactor | Inhibitor |
|---|---|---|
| Hexokinase (HEK), Pyruvate Kinase, Acetate Kinase, Adenylate Kinase, Creatine Kinase | ATP, ADP, AMP | AppNHP, Lonidamine, 2-Deoxy-D-glucose |
| Glucose Oxidase, diaphorase, glucose dehydrogenase | FMN, FAD | 2-Deoxy-D-glucose |
| Beta-galactosidase | | phenylthyl thio-beta-D-galactoside |
| Alkaline phosphatase | | Na[VO(O2)2(triglycine)] |
| Hexokinase | | AppNHP |
| Glucose oxidase | | 2-deoxy-D-glucose |
| Protein kinase A | | PKI peptide |
| dihydrofolate reductase | | Methotrexate |

Isolated: An "isolated" biological component (such as a nucleic acid molecule, protein, virus, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Locked Nucleic Acid (LNA™): A bicyclic nucleic acid where a ribonucleoside is linked between the 2'-oxygen and the 4'-carbon atoms with a methylene unit. This link restricts the flexibility of the ribofuranose ring of the nucleotide analog and locks it into the rigid bicyclic N-type conformation. The LNA also induces adjacent bases to adopt a conformation of the more thermodynamically stable form of the A duplex.

LNA oligonucleotides can be synthesized by standard phosphoramidite chemistry using DNA-synthesizers. In addition, LNA can be mixed with DNA, RNA as well as other nucleic acid analogs. In particular examples, LNAs are included as part of a sensor provided herein.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). MicroRNAs modulate gene expression by promoting cleavage of target mRNAs or by blocking translation of the cellular transcript.

The sensors and methods of the present disclosure can be used to detect miRNAs, such as one associated with disease, such as a cancer, for example, circulating miRNAs can be used as biomarkers for noninvasive diagnosis in cancer diagnosis. hsa-miR-141 (5'-UAACACUGUCUGGUAAAGAUGG; SEQ ID NO: 25) and hsa-miR-375 (UUUGUUCGUUCGGCUCGCGUGA; SEQ ID NO: 26) are the two most overexpressed in prostate epithelial cells hsa-miR-21 (5'-UAGCUUAUCAGACUGAUGUUGA; SEQ ID NO: 3) is one of the most frequently upregulated miRNAs in solid tumors, such as breast cancer. Thus they can be detected in circulation as cancer biomarkers. Another target are a single-nucleotide variants (SNVs) of EGFR-L858R (c.2573 T>G: GTCAAGATCACAGATTTTGGGCGGGC; SEQ DI NO: 27) that is expressed in non-small cell lung cancer. In one example, the sample tested is a breast tissue sample, such as a breast cancer sample, and the miRNA is one or more of miR-125b, miR-145, miR-21 and miR-155. let-7d, miR-210 or miR-221. In one example, the sample tested is a serum sample, and the miRNA is one or more of miR-141, miR-375miR-26a, miR-195 or let-7i (e.g., to test for prostate cancer). In one example, the sample tested is a plasma sample, and the miRNA is one or more of miR-28-3p, miR-30c, miR-92a, miR-140-5p, miR-451 and miR660 (e.g., to test for lung cancer). In one example, the sample tested is a serum sample, and the miRNA is one or more of miR-27b, miR-158a, miR-326 signature or miR-200c (e.g., to test for colon cancer). In one example, a sample is tested for miR-10b for glioma. In one example, a sample is tested for the miR-29 family (miR-29a/-b/-c) for head and neck squamous cell carcinoma metastasis. In one example, a sample is tested for microRNA-712 as a biomarker for atherosclerosis. Thus, in some examples, nucleic acid molecule 132 of FIG. 1D is complementary in sequence to one of these miRNAs.

Nucleic acid molecule: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. It will be understood that when a nucleotide sequence is represented by a DNA sequence (i.e., A, T, G, C), this also includes an RNA sequence (i.e., A, U, G, C) in which "U" replaces "T." Such nucleic acid molecules can be used to form the sensors provided herein.

Conventional notation is used herein to describe nucleotide sequences: the left-hand end of a single-stranded nucleotide sequence is the 5'-end; the left-hand direction of a double-stranded nucleotide sequence is referred to as the 5'-direction.

"cDNA" refers to a DNA that is complementary or identical to an mRNA, in either single stranded or double stranded form.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide. Naturally occurring and non-naturally occurring nucleotides can be used to generate the nucleic acid molecules of the sensors provided herein (such as those of the trigger module and the sensory module).

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

The nucleotides disclosed herein also include nucleotides containing modified bases, modified sugar moieties and modified phosphate backbones, for example as described in U.S. Pat. No. 5,866,336 to Nazarenko et al. A particular example includes a non-hydrolyzable nucleotide.

Nucleotides can be modified at any position on their structures. Examples include, but are not limited to, the modified nucleotides 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified sugar moieties which can be used to modify nucleotides at any position on their structures include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Peptide Nucleic Acid (PNA): A class of informational molecules containing a neutral peptide-like backbone with nucleobases allowing it to hybridize to complementary RNA or DNA with higher affinity and specificity than conventional oligonucleotides. The structure of a PNA molecule is analogous with DNA, wherein the deoxyribose phosphate backbone has been replaced by a backbone similar to that found in peptides. In particular examples, PNA is resistant to nucleases and proteases. PNAs can include a functional group at the N(5)-terminus, such as a fluorophore (for example an acceptor fluorophore). In particular examples, PNAs are included as part of a sensor provided herein.

Pharmaceutically acceptable carrier: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations that can be used with the sensors provided herein. In one example the pharmaceutically acceptable carrier is a pharmaceutically and physiologically acceptable fluid such as water, physiological saline, a balanced salt solution, aqueous dextrose, glycerol or the like. In addition to biologically-neutral carriers, pharmaceutical compositions can contain minor amounts of non-toxic auxiliary substances, such as wetting or emulsifying agents, preservatives, and pH buffering agents and the like, for example sodium acetate or sorbitan monolaurate.

Figure 16A:
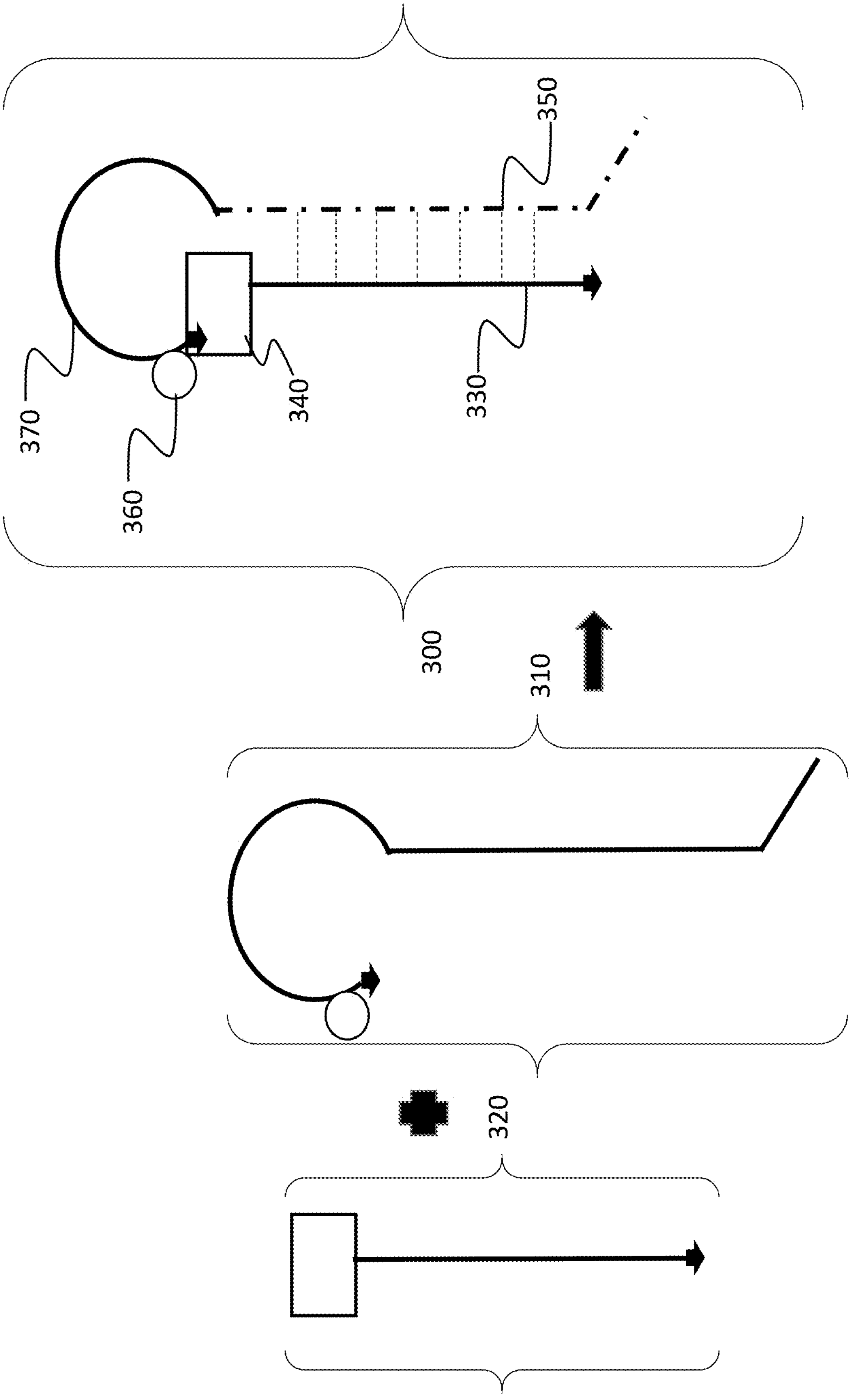
FIG. 16A is a schematic drawing showing an exemplary sensor 300, which includes a trigger module 310 and a sensory module 320, which hybridize to one another to form sensor 300. In this example, the trigger module 310 includes a nucleic acid molecule that includes at least two portions, an aptamer portion 350 and a linker portion 370 (which in some examples is a poly (T) or poly (A) sequence, such as 1 to 60 nt), and an inhibitor 360 (e.g., at or near 5'-end of the linker portion 370). The sensory module 320 includes a nucleic acid molecule 330 and a terminal protein 340 (e.g., at or near the 5'-end of nucleic acid molecule 330. Arrowheads indicate 5'-end (an exemplary embodiment). Nucleic acid molecule 330 is complementary in sequence to at least a portion of aptamer 350. In some examples, the protein 340 is an enzyme, and the inhibitor 360 is an inhibitor of the enzyme 340.
Figure 16B:
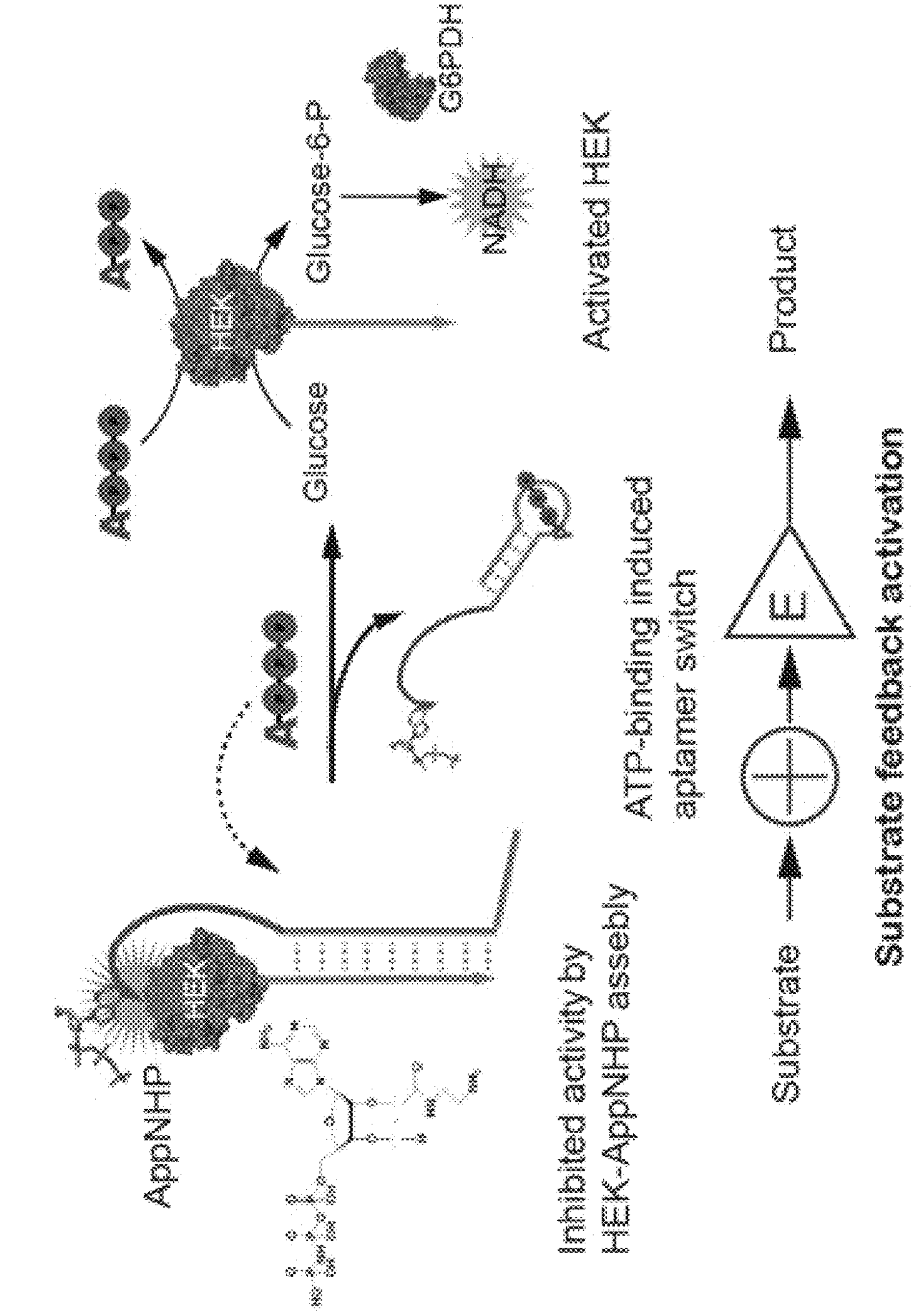
FIG. 16B shows an exemplary design scheme of a sensor that uses feedback control to monitor inhibition of an enzyme using allosteric feedback, specifically substrate (ATP) feedback activation of an inhibited HEK-AppNHP pair for phosphorylating glucose. Other enzyme-inhibitor pairs can be used (e.g., see Table 2).
Figure 16C:
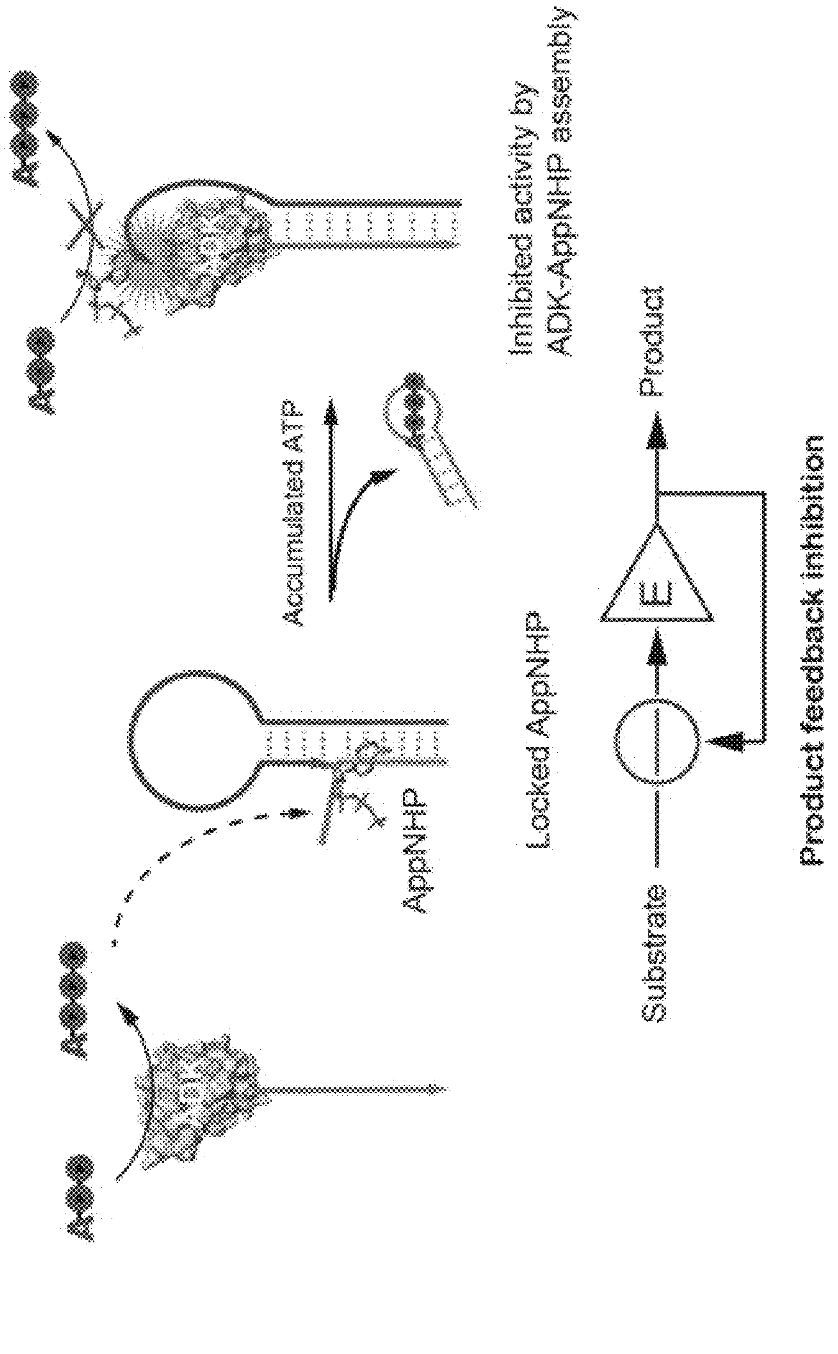
FIG. 16C shows an exemplary design product (ATP) feedback inhibition of an ADK enzyme. Other enzyme-cofactor pairs can be used (e.g., see Table 2).

Sensor: A molecule or device that is used to detect the presence of a target, or the activity of a protein, such as an enzyme. The disclosed sensors in some embodiments (e.g, FIGS. 1A-1H) include a trigger module molecule that is specific for the target agent, and a sensory module that includes an enzyme which can interact with a cofactor of the trigger module, resulting in a detectable reaction (e.g., fluorescence, colorimetric or electrochemical signal). Other embodiments are shown in FIGS. 16A-16C.

Subject: Living multi-cellular organisms, including vertebrate organisms, a category that includes both human and non-human mammals (e.g., cats, dogs, rats, mice, rabbits, pigs and cows). In some examples, a sample analyzed using the disclosed sensors and methods is obtained from a subject.

Target Agent: Any substance whose detection is desired, including, but not limited to, a chemical compound, metal, pathogen, toxin, nucleic acid (such as DNA or RNA, such as miRNA), protein (such as am antibody, cytokine, hormone or antigen), small molecules (such as drug), as well as particular cells (such as a cancer cell or bacterial cell), viruses, or spores.

Under conditions sufficient for: A phrase that is used to describe any environment that permits a desired activity. In one example the desired activity is formation of a complex between a target agent and a trigger module of the sensors provided herein, resulting in a conformational change of the trigger module that allows the cofactor of the trigger module to activate an enzyme of the sensor module, thereby producing or generating a detectable reaction (e.g., fluorescence, colorimetric or electrochemical signal).

Overview

Over the past few decades, nucleic acids have been used to engineer smart nanodevices for applications in molecular sensing, diagnosis, and therapeutics through such strategies as molecular beacons, aptamer switches and toehold displacement. DNA assembly circuits were developed for the specific, sensitive, and rapid detection of molecular targets, such as single-nucleotide polymorphisms or rare DNA variants. To amplify low-abundance signals, enzyme-based or enzyme-free circuits (e.g. entropy-driven DNA circuitry, catalytic hairpin assemblies or deoxyribozymes) were designed to catalyze the production of reporter DNA strands. in vivo toehold switches regulated gene expression and detected virus RNA genome. Alternatively, DNA nanostructures were used to mediate the proximity interaction of catalytic components for actuating chemical reactions. The nucleic acid circuits can be integrated with commercially available glucose meters and pregnancy strips test for detecting multiple biotargets.

In one example, provided herein is a robust and smart DNA nanodevice capable of sensing various bio-targets and reporting an easy-to-read signal. The nanodevice utilizes DNA logic-gated structures to mediate the proximity assembly of enzyme/cofactor system for producing colorimetric or fluorescence signals. Compared with commonly used fluorophore/quencher systems, the actuated reaction produces more detectable signal over time.

Sensors for Detecting Target Agents

Provided herein are sensors that can be used to detect a target agent of interest. Such sensors can be engineered using the methods provided herein to detect a broad range of targets, including nucleic acid molecules (e.g., DNA or RNA, such as mRNA or miRNA), proteins, peptides, antibodies, pathogens (e.g., viruses, bacteria, fungi), cells (e.g., cancer cells, bacterial cells, circulating tumor cells) and small molecules (e.g., drugs, metals). In some examples, the method is qualitative. In some examples, the methods are quantitative. The disclosed sensors include individual nucleic acid molecules (e.g., DNA) that hybridize to one another (e.g., due to complementarity between individual nucleic acid strands, or portions thereof) to form a stem-loop structure containing an enzyme co-factor, which can specifically bind to a target agent. Upon specific binding to the target, in the presence of a sensory enzyme (which is part of the sensory module portion of the sensor), the sensor changes conformation such that a portion of the sensor is released, allowing the sensory enzyme to interact with its co-factor, producing a detectable (e.g., color) reaction, such as a visible color change. Such a sensor can be used in point-of-care (POC) testing. POC testing typically has an easy operation, is reliable, and provides an easy-to-read signal, in diverse and in-home locations by nonspecialists.

Figure 1A:
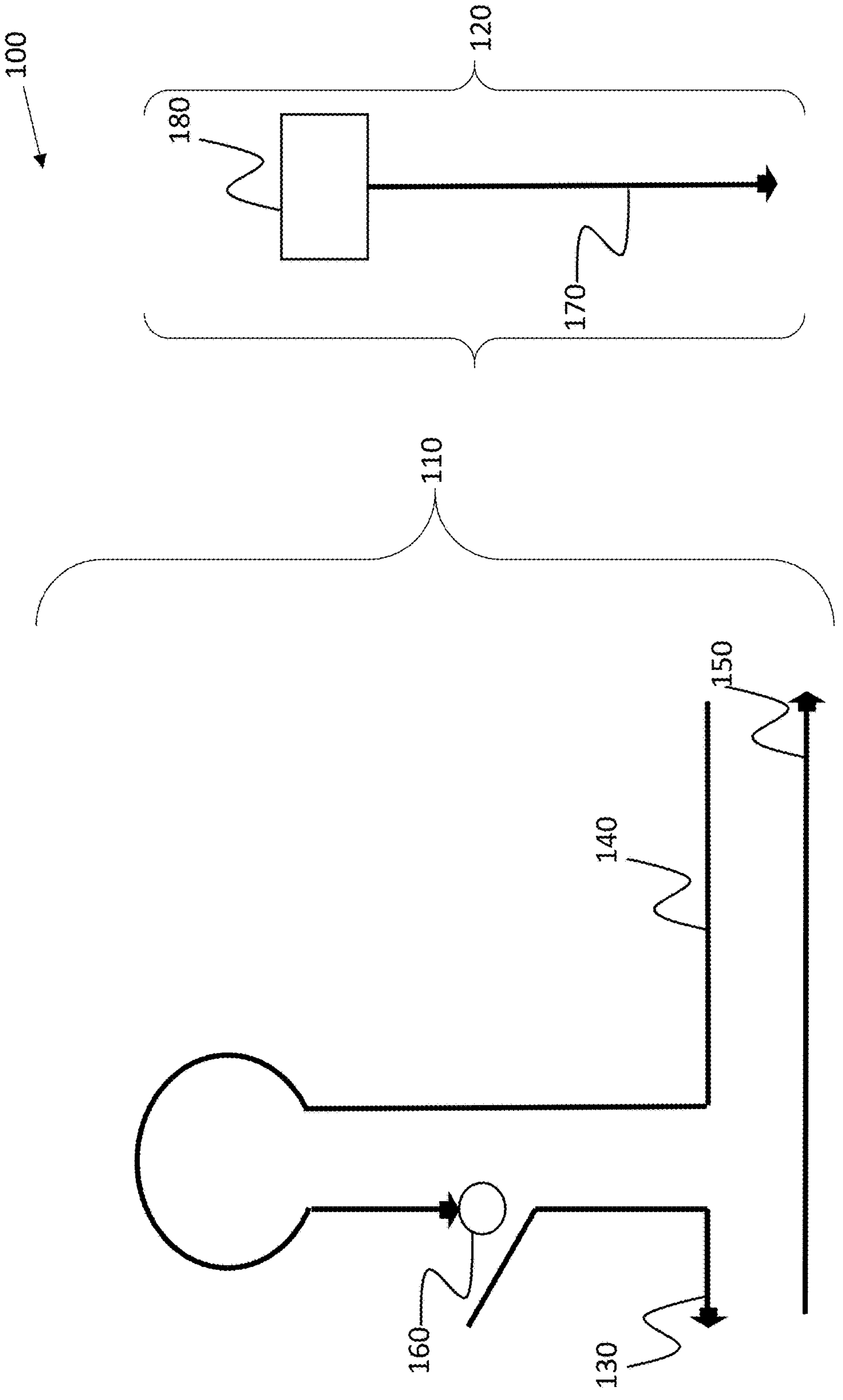
FIG. 1A is a schematic drawing showing an exemplary sensor 100, which includes a trigger module 110 and a sensory module 120. In this example, the trigger module 110 includes three nucleic acid molecules 130, 140, 150 (but nucleic acid molecule 150 is optional, see e.g., FIG. 1B). Nucleic acid molecule 140 includes a terminal cofactor 160 (e.g., at or near 5' or 3'-end nucleic acid molecule 140). The sensory module 120 includes a nucleic acid molecule 170 and a terminal enzyme 180 (e.g., at or near 5' or 3'-end nucleic acid molecule 170, or even near the middle of nucleic acid molecule 170), which is activated by cofactor 160. Arrowheads indicate 5'-end (an exemplary embodiment). Nucleic acid molecule 170 is complementary in sequence to a portion of nucleic acid molecule 140, namely stem 144 (see FIG. 1D).
Figure 1B:
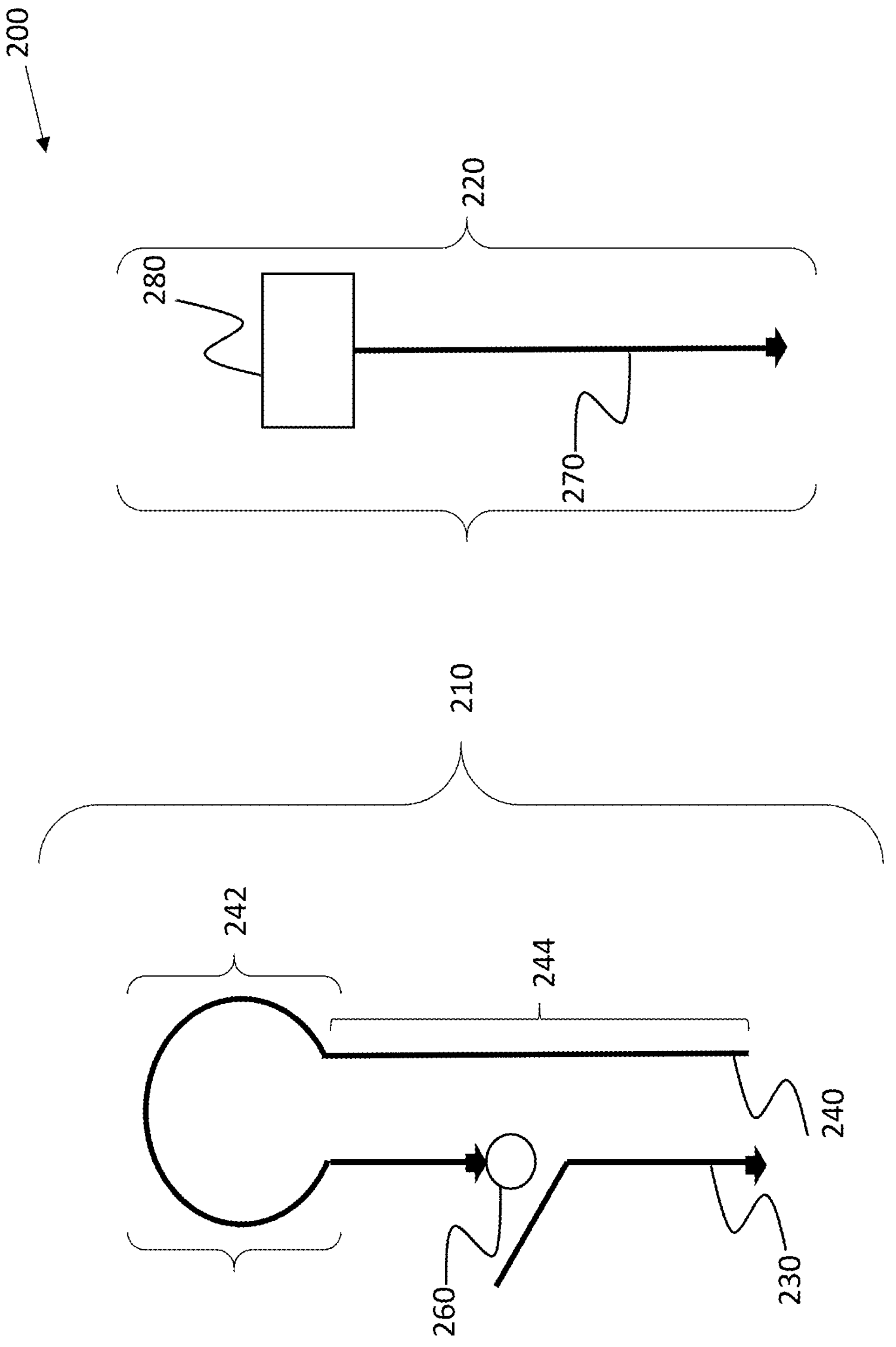
FIG. 1B is a schematic drawing showing an exemplary sensor 200, which includes a trigger module 210 and a sensory module 220. In this example, the trigger module 110 includes nucleic acid molecules 230, 240. Nucleic acid molecule 240 includes a terminal cofactor 260 (e.g., at or near 5' or 3'-end nucleic acid molecule 140). Nucleic acid molecule 240 includes a loop portion 242 and a stem portion 244. The sensory module 220 includes a nucleic acid molecule 270 and a terminal enzyme 280 (e.g., at or near 5' or 3'-end nucleic acid molecule 170, or even near the middle of nucleic acid molecule 270), which is activated by cofactor 260. Arrowheads indicate 5'-end (an exemplary embodiment). Nucleic acid molecule 120 is complementary in sequence to a portion of nucleic acid molecule 240. In some examples, cofactor 260 is instead an inhibitor of enzyme 280 (e.g., see FIG. 16C).

Two different embodiments of the sensor (referred to herein as a DNA nanodevice) are shown in FIGS. 1A and 1B. Other embodiments are shown in FIGS. 16A-16C. Exemplary sensors 100 and 200 are shown in FIGS. 1A and 1B, respectively. Sensors 100 and 200 include two general portions, trigger module 110 or 210 that is specific for the target agent, and sensory module 120 or 220 that competes with a portion of the trigger module (portion 130 or 230) for binding to the trigger module 110 or 210. Thus, kits that include trigger module 110 or 210 and sensory module 120 or 220 are provided (for example in a liquid or solid form). In one example, trigger module 110 and sensory module 120 (or trigger module 210 and sensory module 220) are in separate containers or vials (e.g., glass or plastic). In some examples, the kit is a "one-vial" assay, wherein trigger module 110 and sensory module 120 (or trigger module 210 and sensory module 220) are in the same container or vial, wherein upon addition of a sample containing the target, results in the proximity assembly of enzyme and cofactor, with subsequent production of color or other detectable signal. In one example, the sensor is present on a paper-based detection platform (e.g., see FIGS. 4A-4C). Thus, the kit can include the trigger module and the sensory module dried on a solid support, such as paper (e.g., nitrocellulose).

Exemplary sensor 100 shown in FIG. 1A includes trigger module 110 comprising three nucleic acid molecules 130, 140, 150, and a co-factor 160. In one example, nucleic acid molecules 130, 140, 150, are composed of DNA, which can include naturally or non-naturally occurring nucleotide analogs. In some examples, the nucleic acid molecules 130, 140, 150, are composed of DNA, RNA, LNA, PNA, or combinations thereof. The first nucleic acid molecule 130, which is single stranded (ss), can specifically bind to the target, and includes a first portion that can specifically hybridize to a portion of the second nucleic acid molecule 140 and a second portion that can hybridize to a portion of the third nucleic acid molecule 150. The second nucleic acid molecule 140, which is ss, includes a cofactor 160 at or near one end (such as at or near the 3'- or 5'-end). The second nucleic acid molecule 140, in the absence of the target, forms a stem-loop structure that embeds the cofactor 160, wherein a portion of the stem is complementary to a portion of the first nucleic acid molecule 130, thereby allowing hybridization of the first nucleic acid strand 130 to the second nucleic acid molecule 140. The third nucleic acid molecule 150, which is ss, includes a first portion that is complementary to the first nucleic acid molecule 130, a second portion that is not complementary to either the first nucleic acid molecule 130 or the second nucleic acid molecule 140, and a third portion that this complementary to the second nucleic acid strand 140, thereby allowing the third nucleic acid molecule 150 to hybridize to the first 130 and second 140 nucleic acid molecule. As shown in FIG. 1A, exemplary sensory module 120 includes a ss nucleic acid molecule 170, which is complementary in sequence to the stem of the second nucleic acid strand 140, and an enzyme (such as glucose-6-phosphate) 180 at or near one end (such as at or near the 3'- or 5'-end) or even at or near the middle, which has activity in the presence of cofactor 160. In some examples, the ss nucleic acid molecule 170 has a length of at least 15 nt, at least 20 nt, at least 25 nt, or at least 30 nt, such as 15 to 40 nt, 15 to 30 nt, or 15 to 50 nt, such as 15, 16, 17, 18, 19, 20, 25, 30, 35, 40, 45, or 50 nt.

In some examples, the first nucleic acid strand 130 has a length of at least 15 nt, at least 20 nt, at least 25 nt, or at least 30 nt, such as 15 to 40 nt, 15 to 30 nt, 15 to 50 nt, or 15 to 60 nt. In some examples, the second nucleic acid strand 140 has a length of at least 15 nt, at least 20 nt, at least 25 nt, or at least 30 nt, such as 15 to 40 nt, 15 to 30 nt, 15 to 50 nt, or 15 to 60 nt. In some examples, the third nucleic acid strand 150 has a length of at least at least 15 nt, at least 20 nt, at least 25 nt, or at least 30 nt, such as 15 to 40 nt, 15 to 30 nt, 15 to 50 nt, or 15 to 60 nt, such as 15, 16, 17, 18, 19, 20, 25, 30, 35, 40, 45, 50, 55, or 60 nt.

Exemplary sensor 200 shown in FIG. 1B includes trigger module 210 comprising two nucleic acid molecules 120, 240, and a co-factor 260. In some examples, such as sensor is used when nucleic acid molecule 230 comprises an aptamer. In one example, nucleic acid molecules 230, 240 are composed of DNA, which can include naturally or non-naturally occurring nucleotide analogs. In some examples, the nucleic acid molecules 230, 240 are composed of DNA, RNA, LNA, PNA, or combinations thereof. The first nucleic acid molecule 230, which is single stranded (ss), can specifically bind to the target, and includes a first portion that can specifically hybridize to a portion of the second nucleic acid molecule 240. The second nucleic acid molecule 240, which is ss, includes a cofactor 260 at or near one end (such as at or near the 3'- or 5'-end). The second nucleic acid molecule 240, in the absence of the target, forms a stem-loop structure that embeds the cofactor 260, wherein a portion of the stem is complementary to a portion of the first nucleic acid molecule 230, thereby allowing hybridization of the first nucleic acid strand 230 to the second nucleic acid molecule 240. As shown in FIG. 1B, exemplary sensory module 220 includes a ss nucleic acid molecule 270, which is complementary in sequence to the stem 244 of the second nucleic acid strand 240, and an enzyme (such as glucose-6-phosphate) 280 at or near one end (such as at or near the 3'- or 5'-end) or even at or near the middle, which has activity in the presence of cofactor 260. In some examples, the ss nucleic acid molecule 170 has a length of at least 15 nt, at least 20 nt, at least 25 nt, or at least 30 nt, such as 15 to 40 nt, 15 to 30 nt, or 15 to 50 nt, such as 15, 16, 17, 18, 19, 20, 25, 30, 35, 40, 45, or 50 nt. In some examples, the first nucleic acid strand 230 has a length of at least 15 nt, at least 20 nt, at least 25 nt, or at least 30 nt, such as 15 to 40 nt, 15 to 30 nt, 15 to 50 nt, or 15 to 60 nt. In some examples, the second nucleic acid strand 240 has a length of at least 15 nt, at least 20 nt, at least 25 nt, or at least 30 nt, such as 15 to 40 nt, 15 to 30 nt, 15 to 50 nt, or 15 to 60 nt. In some examples cofactor 260 is not a co-factor but instead an enzyme inhibitor (e.g., see FIG. 16C, and specific examples in Table 2).

Figure 1C:
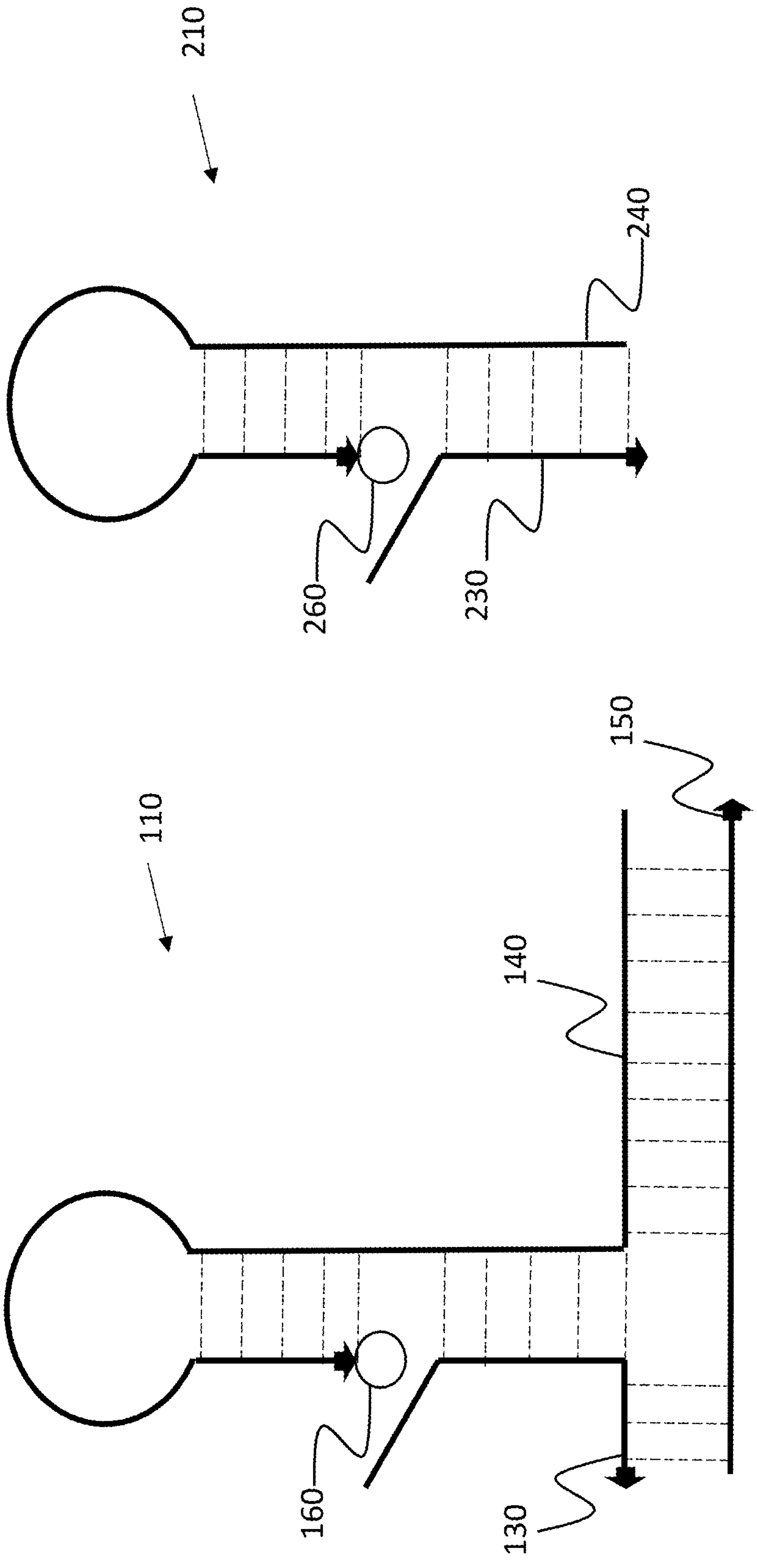
FIG. 1C is a schematic drawing showing exemplary trigger modules 110, 210 portion of sensor 100, 200, respectively, and how the individual nucleic acid molecules 130, 140 and 150 of trigger module 110 can hybridize to one another (dashed lines), and how the individual nucleic acid molecules 230, 240 of trigger module 210 can hybridize to one another (dashed lines).

FIG. 1C shows how the individual nucleic acid strands 130, 140, 150 of trigger module 110 hybridize to one another (shown schematically as dashed lines between the strands), to form a trigger module 110 with secondary structure, and how the individual nucleic acid strands 230, 240 of trigger module 210 hybridize to one another (shown schematically as dashed lines between the strands), to form a trigger module 210 with secondary structure. Arrowheads shown in FIGS. 1A, 1B, 1C represent the 5'-end of the individual nucleic acid molecules 130, 140, 150, 230 and 240. One skilled in the art will appreciate that this can be switched for each of the three nucleic acid molecules 130, 140, 150, 230, 240 (e.g., for each nucleic acid molecule 130, 140, 150, 230, 240 the 5'- and the 3'-end can be reversed). Thus, in one example (e.g., see FIG. 1C, left structure), the 5'-end of the first nucleic acid molecule 130 hybridizes to the 3'-end of the third nucleic acid molecule 150, the 3'-end of the first nucleic acid molecule 130 includes the region specific for the target, a central region of the first nucleic acid molecule 130 hybridizes to a central region of the second nucleic acid molecule 140, a 5'-end of the second nucleic acid molecule 140, which includes the cofactor 160, hybridizes to a central region of the second nucleic acid molecule 140 to form a loop and part of the stem, and the 3'-end of the second nucleic acid molecule 140 hybridizes to the 5'-end of the third nucleic acid molecule 150. Alternatively (not shown), the 3'-end of the first nucleic acid molecule 130 hybridizes to the 5'-end of the third nucleic acid molecule 150, the 5'-end of the first nucleic acid molecule 130 includes the region specific for the target, a central region of the first nucleic acid molecule 130 hybridizes to a central region of the second nucleic acid molecule 140, a 3'-end of the second nucleic acid molecule 140, which includes the cofactor 160, hybridizes to a central region of the second nucleic acid molecule 140 to form part of the stem, and the 5'-end of the second nucleic acid molecule 140 hybridizes to the 3'-end of the third nucleic acid molecule 150. Thus, in one example (e.g., see FIG. 1C, right structure), the 5'-end of the first nucleic acid molecule 230 hybridizes to the 3'-end of the second nucleic acid molecule 240, wherein the 3'-end of the first nucleic acid molecule 230 includes the region specific for the target (e.g., is a functional nucleic acid molecule) that does not hybridize to the second nucleic acid molecule 240. A 5'-end of the second nucleic acid molecule 240, which includes the cofactor 260, hybridizes to a central region of the second nucleic acid molecule 240 to form the loop region and part of the stem. Alternatively (not shown), the 3'-end of the first nucleic acid molecule 230 hybridizes to the 5'-end of the second nucleic acid molecule 24, the 5'-end of the first nucleic acid molecule 230 includes the region specific for the target, a 3'-end of the second nucleic acid molecule 240, which includes the cofactor 260, hybridizes to a central region of the second nucleic acid molecule 240 to form a loop and part of the stem.

Figure 1E:
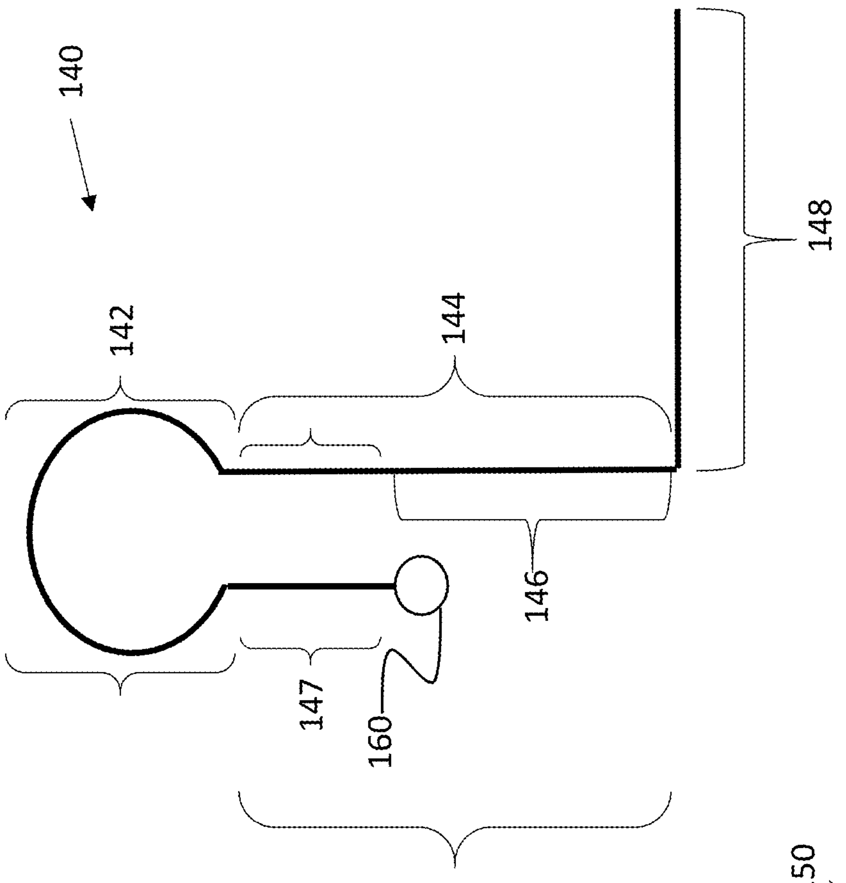
FIG. 1E is a schematic drawing showing second nucleic acid molecule 140 of exemplary trigger molecule 110, which includes a terminal cofactor 160, a loop 142 formed upon hybridization between portions 147 due to their complementarity, stem 144 (which includes regions 146 and 147), and portion 148 that is complementary in sequence to region 154 of the third nucleic acid strand 150, thereby allowing hybridization of portion 148 of the second nucleic acid strand to portion 154 of the third nucleic acid strand.
Figure 1D:
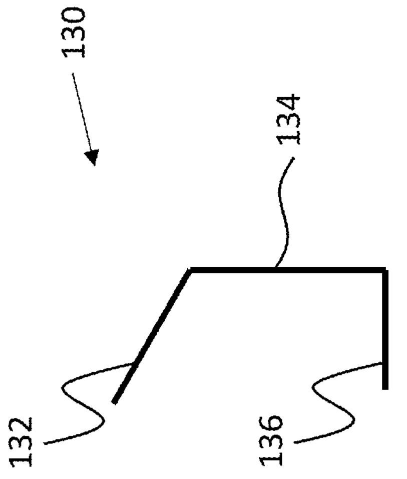
FIG. 1D is a schematic drawing showing exemplary first nucleic acid molecule 130 of exemplary trigger molecule 110, having three parts 132, 134, 136. Portion 132 is specific for the target. Portion 134 of first nucleic acid molecule 130 is complementary in sequence to portion 146 of stem 144 of second nucleic acid molecule 140, thereby allowing hybridization of portion 134 of the first nucleic acid strand to portion 144 of the second nucleic acid strand. Portion 136 of the first nucleic acid molecule 130 is complementary in sequence to portion 152 of the third nucleic acid molecule 150, thereby allowing hybridization of portion 136 of the first nucleic acid strand to portion 152 of the third nucleic acid strand.
Figure 1F:
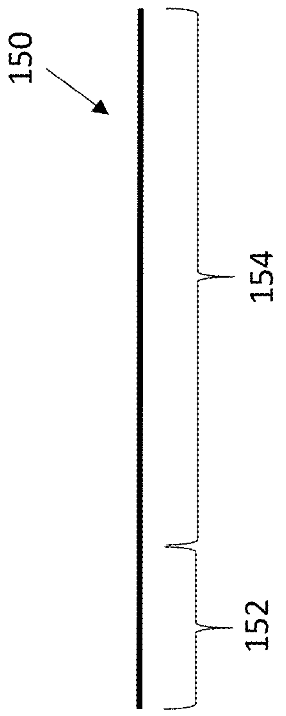
FIG. 1F is a schematic drawing showing the third nucleic acid molecule 150 of exemplary trigger molecule 110, having two regions 152 and 154. Portion 152 is complementary in sequence to portion 136 of the first nucleic acid strand 130, allowing these two portions to hybridize to one another, and portion 154 is complementary in sequence to portion 148 of the second nucleic acid strand 140, allowing these two portions to hybridize to one another.

FIG. 1D shows portions 132, 134, and 136 of exemplary first nucleic acid molecule 130 of trigger module 110. FIG. 1E shows portions 142, 144, 146, 147, and 148 of exemplary second nucleic acid molecule 140 (with a terminal cofactor 160) of trigger module 110. FIG. 1F shows portions 152 and 154 of the third nucleic acid molecule 150 of trigger module 110.

As shown in FIG. 1D, the first nucleic acid strand 130 includes three portions 132, 134, and 136. Portion 132 is specific for the target. In some examples, the target is a nucleic acid molecule (such as a nucleic acid molecule specific for disease or infection, such as a cancer-specific DNA or RNA, such as an miRNA), and portion 132 of the first nucleic acid strand 130 is complementary to a region the target nucleic acid molecule, such that the target nucleic acid molecule can hybridize to the first nucleic acid molecule 130 at portion 132. In other examples, portion 132 of the first nucleic acid strand 130 is an aptamer or aptazyme (or other functional nucleic acid molecule) specific for the target (such as a small molecule, such as a drug or metal). In some examples, portion 132 has a length of at least 6 nt, at least 7 nt, at least 8 nt, at least 9 nt, or at least 10 nt, such as 6 to 10 nt, 6 to 50 nt, or 6 to 20 nt, such as 6, 7, 8, 9, 10, 11, 12, 13, 14, 15, 16, 17, 18, 19 or 20 nt. Portion 134 of the first nucleic acid molecule 130 is complementary in sequence to portion 146 of stem 144 of the second nucleic acid molecule 140, thereby allowing hybridization of portion 134 of the first nucleic acid strand to portion 144 of the second nucleic acid strand (see FIGS. 1C, 1D, 1E). In some examples, portion 134 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt. Portion 136 of the first nucleic acid molecule 130 is complementary in sequence to portion 152 of the third nucleic acid molecule 150, thereby allowing hybridization of portion 136 of the first nucleic acid strand to portion 152 of the third nucleic acid strand (see FIGS. 1B, 1C, 1E). In some examples, portion 136 is at least 3 nt, at least 4 nt, or at least 5 nt, such as 3 to 10 nt, 3 to 6 nt, or 3 to 5 nt, such as 3, 4, 5, 6, 7, 8, 9 or 10 nt.

As shown in FIG. 1E, the second nucleic acid strand 140 includes portions 142, 144 (which includes portions 146, 147), 148 and 160. The second nucleic acid strand 140 includes a terminal co-factor 160 (e.g., NAD, ATP or hemin) and a hairpin loop having stem 144 and loop 142 portions. The loop 142 in some examples includes 3 to 20 nucleotides, such as 3 to 10 nt, 3 to 6 nt, or 5 to 6 nt (such as 3, 4, 5, 6, 7, 8, 9, 10, 11, 12, 13, 14, 15, 16, 17, 18, 19 or 20 nt). In some examples, the loop 142 is a poly-T or poly-A sequence, such as 3, 4, 5, 6, 7, 8, 9, 10, 11, 12, 13, 14, 15, 16, 17, 18, 19 or 20 As or 3, 4, 5, 6, 7, 8, 9, 10, 11, 12, 13, 14, 15, 16, 17, 18, 19 or 20 Ts (such as 3 to 20 As or Ts, such as 3 to 10 As or Ts, 3 to 6 As or Ts, or 5 to 6 As or Ts). Nucleotides of the loop do not hybridize to one another. The stem 144 embeds the cofactor 160 in the absence of the target. The stem 144 includes region 147 closest to the loop 142 (and includes a terminal co-factor 160), and portion 146 away from the loop. Portion 147 is double stranded (see FIG. 1C). Portion 146 is complementary to region 134 of the first nucleic acid strand 130, thus allowing hybridization between portions 134 and 146 in the absence of the target (see FIG. 1C). Portion 148 of the second nucleic acid strand 140 is complementary in sequence to region 154 of the third nucleic acid strand 150, thereby allowing hybridization of portion 148 of the second nucleic acid strand to portion 154 of the third nucleic acid strand (see FIGS. 1C, 1E, 1F). In some examples, stem 144 has a length of at least 10 nt, at least 15 nt, at least 20 nt, at least 25 nt, at least 30 nt, or at least 50 nt, such as 10 to 20 nt, 10 to 30 nt, 10 to 40 nt, 10 to 50 nt, or 10 to 60 nt, such as 10, 11, 12, 13, 14, 15, 16, 17, 18, 19, 20, 25, 30, 35, 40, 45, 50, 55, or 60 nt. In some examples, portion 146 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt. In some examples, each part of portion 147 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt. In some examples, portion 148 is at least 5 nt, at least 8 nt, at least 10 nt, or at least 20 nt, such as 10 to 30 nt, 10 to 20 nt, or 10 to 15 nt, such as 10, 11, 12, 13, 14, 15, 16, 17, 18, 19, 20, 21, 22, 23, 24, 25, 26, 27, 28, 29, or 30 nt.

As shown in FIG. 1F, the third nucleic acid strand 150 forms the base of the sensor. The third nucleic acid molecule 150 includes portions 152 and 154. In some examples, the third nucleic acid molecule 150 is at least 10 nt, at least 15 nt, at least 20 nt, at least 25 nt, at least 30 nt, or at least 50 nt, such as 10 to 20 nt, 10 to 30 nt, 10 to 40 nt, 10 to 50 nt, or 10 to 60 nt, such as 10, 11, 12, 13, 14, 15, 16, 17, 18, 19, 20, 25, 30, 35, 40, 45, 50, 55, or 60 nt. As discussed above, portion 152 is complementary in sequence to portion 136 of the first nucleic acid strand 130, allowing these two portions to hybridize to one another, thereby forming a ds region (see FIG. 1C). In some examples, portion 152 (and portion 136) is at least 3 nt, at least 4 nt, or at least 5 nt, such as 3 to 10 nt, 3 to 6 nt, or 3 to 5 nt, such as 3, 4, 5, 6, 7, 8, 9 or 10 nt. As discussed above, portion 154 is complementary in sequence to portion 148 of the second nucleic acid strand 140, allowing these two portions to hybridize to one another, thereby forming a ds region (see FIG. 1C). In some examples, portion 154 (and portion 148) is longer than portion 152, such as at least 2×, at least 3×, at least 4×, at least 5×, at least 6×, at least 7×, at least 8×, at least 9×, or at least 10× the length of portion 152 (such as at least 10, at least 15, or at least 20 more nt than portion 152), such as having a length of at least 5 nt, at least 8 nt, or at least 10 nt, such as 10 to 30 nt, 10 to 20 nt, or 10 to 15 nt, such as 10, 11, 12, 13, 14, 15, 16, 17, 18, 19, 20, 21, 22, 23, 24, 25, 26, 27, 28, 29, or 30 nt.

Figure 1H:
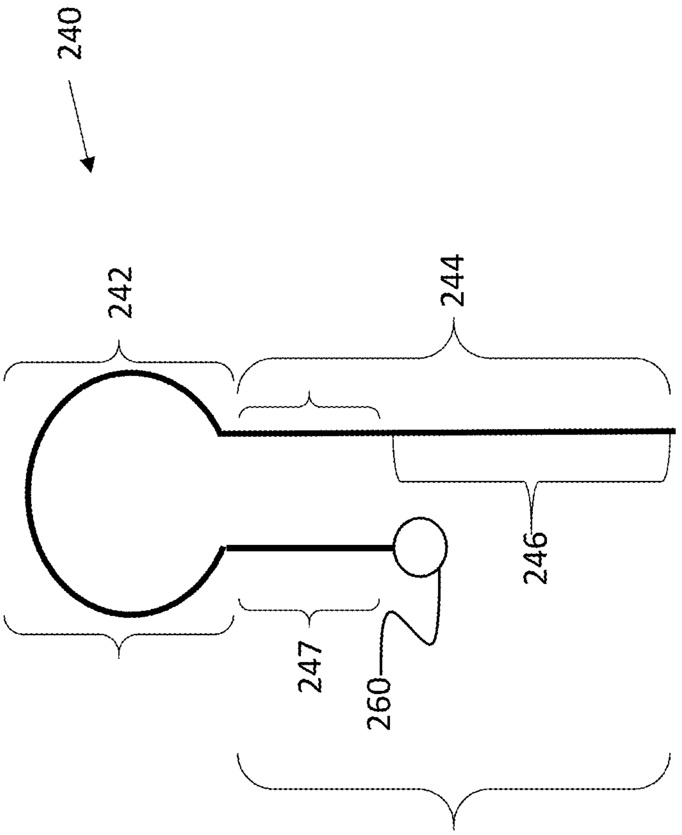
FIG. 1H is a schematic drawing showing second nucleic acid molecule 240 of exemplary trigger molecule 210, which includes a terminal cofactor 260 (or instead an enzyme inhibitor, e.g., see FIG. 16C), a loop 242 formed upon hybridization between portions 247 due to their complementarity and stem 244 (which includes regions 246 and one portion of 247).
Figure 1G:
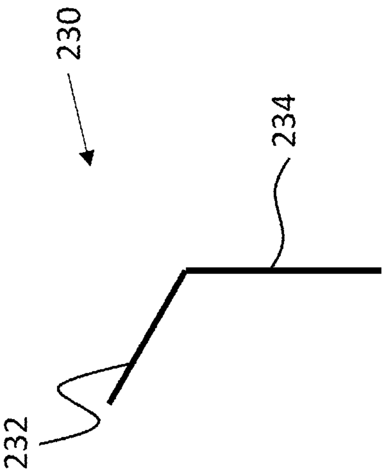
FIG. 1G is a schematic drawing showing exemplary first nucleic acid molecule 230 of exemplary trigger molecule 210, having regions 232, 234. Portion 232 is specific for the target (and is in some examples a functional nucleic acid molecule, such as an aptamer). Portion 234 of first nucleic acid molecule 230 is complementary in sequence to portion 246 of stem 244 of second nucleic acid molecule 240, thereby allowing hybridization of portion 234 of the first nucleic acid strand to portion 244 of the second nucleic acid strand.

FIG. 1G shows portions 232, 234 of exemplary first nucleic acid molecule 230 of trigger module 210 (see FIG. 1B). FIG. 1H shows portions 242, 244, 246, 247 of exemplary second nucleic acid molecule 240 (with a terminal cofactor 260) of trigger module 210 (see FIG. 1B). In some examples terminal cofactor 260 is not a co-factor but instead an enzyme inhibitor (e.g., see FIG. 16C, and specific examples in Table 2).

As shown in FIG. 1G, the first nucleic acid strand 230 of trigger module 210 includes two portions 232 and 234. Portion 232 is specific for the target. In some examples, portion 232 of the first nucleic acid strand 230 is an aptamer or aptazyme (or other functional nucleic acid molecule) specific for the target (such as a small molecule, such as a drug or metal). In some examples, portion 232 has a length of at least 6 nt, at least 7 nt, at least 8 nt, at least 9 nt, or at least 10 nt, such as 6 to 10 nt, 6 to 50 nt, or 6 to 20 nt, such as 6, 7, 8, 9, 10, 11, 12, 13, 14, 15, 16, 17, 18, 19 or 20 nt. Portion 234 of the first nucleic acid molecule 230 is complementary in sequence to portion 246 of stem 244 of the second nucleic acid molecule 240, thereby allowing hybridization of portion 234 of the first nucleic acid strand to portion 244 of the second nucleic acid strand (see FIGS. 1C, 1G, 1H). In some examples, portion 234 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt.

As shown in FIG. 1H, the second nucleic acid strand 240 of trigger module 210 includes portions 242, 244 (which includes portions 246, 247) and 260. The second nucleic acid strand 240 includes a terminal co-factor 260 (e.g., NAD, ATP or hemin) and a hairpin loop having stem 244 and loop 242 portions. IN some example, cofactor 260 is not a co-factor but is instead an enzyme inhibitor (e.g., see FIG. 16C). The loop 242 in some examples includes 3 to 20 nucleotides, such as 3 to 10 nt, 3 to 6 nt, or 5 to 6 nt (such as 3, 4, 5, 6, 7, 8, 9, 10, 11, 12, 13, 14, 15, 16, 17, 18, 19 or 20 nt). In some examples, the loop 242 is a poly-T or poly-A sequence, such as 3, 4, 5, 6, 7, 8, 9, 10, 11, 12, 13, 14, 15, 16, 17, 18, 19 or 20 As or 3, 4, 5, 6, 7, 8, 9, 10, 11, 12, 13, 14, 15, 16, 17, 18, 19 or 20 Ts (such as 3 to 20 As or Ts, such as 3 to 10 As or Ts, 3 to 6 As or Ts, or 5 to 6 As or Ts). Nucleotides of the loop do not hybridize to one another. The stem 244 embeds the cofactor 260 in the absence of the target. The stem 244 includes region 247 closest to the loop 242 (and includes a terminal co-factor 260), and portion 246 away from the loop. Portion 247 is double stranded (see FIG. 1C). Portion 246 is complementary to region 234 of the first nucleic acid strand 230, thus allowing hybridization between portions 234 and 246 in the absence of the target (see FIG. 1C). In some examples, stem 244 has a length of at least 10 nt, at least 15 nt, at least 20 nt, at least 25 nt, at least 30 nt, or at least 50 nt, such as 10 to 20 nt, 10 to 30 nt, 10 to 40 nt, 10 to 50 nt, or 10 to 60 nt, such as 10, 11, 12, 13, 14, 15, 16, 17, 18, 19, 20, 25, 30, 35, 40, 45, 50, 55, or 60 nt. In some examples, portion 246 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt. In some examples, each part of portion 247 has a length of at least 8 nt, at least 9 nt, at least 10 nt, at least 20 nt, at least 25 nt, at least 30 nt, or at least 50 nt, such as 8 to 20 nt, 8 to 30 nt, 8 to 40 nt, 8 to 50 nt, or 8 to 60 nt, such as 8, 9, 10, 11, 12, 13, 14, 15, 16, 17, 18, 19, 20, 25, 30, 35, 40, 45, 50, 55, or 60 nt.

Thus, provided are compositions that include trigger module 110 that is specific for the target agent and sensory module 120 that competes with the target for binding with trigger module 110. Also provided are compositions that include trigger module 210 that is specific for the target agent and sensory module 220 that competes with the target for binding with trigger module 210. Such compositions can include other reagents, such as water, saline or a buffer. In some examples, such compositions further include detectable reagent, such as those listed in Table 3.

In some examples the sensor of the present application includes allosteric feedback control (e.g., DNA logic gate), which can allow for the identification of a molecule with a desired functions. In some examples, such a sensor can be used to determine the activity of a protein, such as an enzyme.

An example of such a sensor is shown in FIG. 16A. The sensor 300 includes trigger module 310 and sensory module 320, which are hybridized together (dashed lines joining the two nucleic acid strands). This dsDNA scaffold includes a protein 340 (such as an enzyme), and an inhibitor of the protein 360 (e.g., inhibitor of the enzyme).

The trigger module 310 includes a nucleic acid molecule, which at its 3'-end is an aptamer sequence 350 (dashed-dotted line) and at its 5'-end a linker nucleic acid sequence 370 (solid line) and an inhibitor 360. The inhibitor 360 can be at or near the 5'-end of the nucleic acid molecule of the trigger module 310. Exemplary inhibitors that can be used include 2'/3'-O-(2-Aminoethyl-carbamoyl)-adenosine-5'-[(β, γ)-imido] triphosphate (AppNHP), lonidamine, and 2-deoxy-d-glucose. In some examples, the aptamer sequence 350 has a length of at least 20 nt, at least 25 nt, at least 30 nt, or at least 50 nt, such as 20 to 100 nt, 20 to 50 nt, 20 to 35 nt, 25 to 35 nt, or 30 to 50 nt, such as 20, 25, 30, 35, 40, 45, 50, 55, or 60 nt. In some examples, linker nucleic acid sequence 370 has a length of at least 1 nt, at least 2 nt, at least 3, nt, at least 4, nt, at least 5, nt, at least 6, nt, at least 7, nt, 8 nt, at least 9 nt, at least 10 nt, at least 20 nt, at least 25 nt, at least 30 nt, or at least 50 nt, such as 1 to 60 nt, 10 to 30 nt, 15 to 30 nt, 20 to 40 nt, 20 to 25 nt, or 15 to 25 nt, such as 8, 9, 10, 11, 12, 13, 14, 15, 16, 17, 18, 19, 20, 21, 22, 23, 24, 25, 26, 27, 28, 29, 30, 35, 40, 45, 50, 55, or 60 nt. In some examples, the linker 370 is a poly-T or poly-A sequence, such as 1, 2, 3, 4, 5, 6, 7, 8, 9, 10, 11, 12, 13, 14, 15, 16, 17, 18, 19 or 20 As or 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 Ts (such as 10 to 40 As or Ts, such as 15 to 25 As or Ts). Nucleotides of the linker 370 do not hybridize to one another. In some examples, the nucleic acid molecule (350+370) of trigger module 310 has a length of at least 30 nt, at least 35 nt, at least 40 nt, at least 45 nt, at least 50 nt, at least 55 nt, or at least 60 nt, such as 30 to 100 nt, 30 to 80 nt, 30 to 60 nt, 40 to 60 nt, or 45 to 55 nt, such as 30, 35, 40, 41, 42, 43, 44, 45, 46, 47, 48, 49, 50, 51, 52, 53, 54, 55, 56, 57, 58, 59 or 60 nt.

The sensory module 320 includes a nucleic acid molecule 330 and a terminal protein 340 (such as an enzyme, for example a kinase). The nucleic acid molecule 330 of the sensory module 320 includes some complementarity to the aptamer sequence 350 (thereby allowing hybridization of the nucleic acid sequence 330 of the sensory module 320 to a central portion of the nucleic acid molecule of trigger module 310), and includes a protein 340. The protein 340 is at or near the 3'-end of the nucleic acid molecule 330, and in some examples is an enzyme, such as a kinase, for example HEK, pyruvate kinase, acetate kinase, adenylate kinase, or creatine kinase. In some examples the protein 340 is glucose oxidase, diaphroase, or glucose dehydrogenase. In some examples, nucleic acid molecule 330 has a length of at least 8 nt, at least 9 nt, at least 10 nt, at least 20 nt, at least 25 nt, at least 30 nt, or at least 50 nt, such as 10 to 30 nt, 15 to 30 nt, 20 to 40 nt, 20 to 25 nt, or 15 to 25 nt, such as 8, 9, 10, 11, 12, 13, 14, 15, 16, 17, 18, 19, 20, 21, 22, 23, 24, 25, 26, 27, 28, 29, 30, 35, 40, 45, 50, 55, or 60 nt. In some examples, the nucleic acid molecule 330 of the sensory module 320 includes at least 10 complementarity nt to aptamer sequence 350, such as at least 15, at least 20 nt, at least 25 nt, at least 30 nt, or at least 50 nt, such as 10 to 30 nt, 15 to 30 nt, 20 to 40 nt, 20 to 25 nt, or 15 to 25 nt, such as 8, 9, 10, 11, 12, 13, 14, 15, 16, 17, 18, 19, 20, 21, 22, 23, 24, 25, 26, 27, 28, 29, 30, 35, 40, 45, 50, 55, or 60 nt complementarity to aptamer sequence 350.

In the absence of a molecule that the aptamer specifically binds, the protein 340 and the inhibitor 360 are in proximity such that the inhibitor 350 significantly reduces the activity of the protein 340 (such as a reduction of at least 50%, at least 75%, at least 90%, or 100%). However, in the presence of the molecule which the aptamter specifically binds (such as ATP), the aptamer 350 will bind to the molecule, resulting in a conformational change in the aptamer 350, release of the trigger module 310 from the sensor 300, allowing activation of protein 340 (e.g., as it is no longer in proximity to inhibitor 360). The activity of the protein 340 can then be monitored, such as phosphorylation of a protein.

In one example, nucleic acid molecules 330, 350, 370, are composed of DNA, which can include naturally or non-naturally occurring nucleotide analogs. In some examples, the nucleic acid molecules 330, 350, 370, are composed of DNA, RNA, LNA, PNA, or combinations thereof. Each first nucleic acid molecule 330, 350, 370 can be single stranded (ss).

Generation of Trigger Module

To generate the trigger sensor 110 or 210, individual nucleic acid strands (e.g., 130, 140 and 150, or 230 and 240) are incubated under conditions that allow the nucleic acid strands to hybridize, for example at pH 7-9 in the presence of a salt buffer containing phosphate, Tris, HEPESS at room temperature, or a temperature gradient from 90° C. to 4° C. The hybridization may take 0.5 hour to 3 hour. ~0.5-4 mM Mg2+ can be included to stabilize the hybridization assembly. Additional details are found at Fu et al., *Nat. Protocols* 2016, 11, 2243-2273.

Attachment of Cofactor to Nucleic Acid Molecule

Nucleic acid molecules can be modified with cofactors for controlling catalytic function. For example, as described in Fu et al., *Nat. Protocols* 2016, 11, 2243-2273, an amino-modified NAD analogue (an enzyme cofactor) is conjugated to an amine-modified oligonucleotide using a disuccinimidyl suberate (DSS) linker on anion-exchange DEAE-Sepharose resin. The $NAD^+$-modified DNA is purified using high-performance liquid chromatography (HPLC) and can be characterized using mass spectrometry.

Similar methods can be used to attach an enzyme or enzyme inhibitor to a nucleic acid molecule (e.g., 360, 340, 330, and 370 of FIG. 16A).

Functional Nucliec Acids (FNA)

In one example, the target is a small molecule (such as a drug, protein, or metal), and portion 132 of the first nucleic acid strand 130 or portion 232 of the first nucleic acid strand 230 is a functional nucleic acid molecule, such as an aptamer or aptazyme (e.g., DNAzyme or RNAzyme). FNAs can also contain native or modified nucleotides. FNAs may be selected to bind to a wide range of analytes with high affinity and specificities.

Aptamers are nucleic acids (such as DNA or RNA) that recognize targets with high affinity and specificity. For example, the adenosine aptamer binds adenosine as its corresponding target. Aptazymes (also called allosteric DNA/RNAzymes or allosteric (deoxy) ribozymes) are DNA/RNAzymes regulated by an effector (the target molecule). They typically contain an aptamer domain that recognizes an effector and a catalytic domain. The effector can either decrease or increase the catalytic activity of the aptazyme through specific interactions between the aptamer domain and the catalytic domain. Therefore, the activity of the aptazyme can be used to monitor the presence and quantity of the effector (i.e., target).

Methods of identifying a functional DNA that is specific for a particular target agent have been described in several patents (e.g., U.S. Pat. Nos. 7,192,708; 7,332,283; 7,485,419; 7,534,560; and 7,612,185, and US Patent Publication Nos. 20070037171 and 20060094026, describe methods of identifying functional DNA molecules that can bind to particular ions, such as lead and cobalt). In vitro selection methods can be used to obtain aptamers for a wide range of target molecules with exceptionally high affinity, having dissociation constants as high as in the picomolar range (Brody and Gold, *J. Biotechnol.* 74: 5-13, 2000; Jayasena, *Clin. Chem.*, 45:1628-1650, 1999; Wilson and Szostak, *Annu. Rev. Biochem.* 68: 611-647, 1999). For example, aptamers have been developed to recognize metal ions such as Zn(II) (Ciesiolka et al., *RNA* 1: 538-550, 1995) and Ni(II) (Hofmann et al., *RNA*, 3:1289-1300, 1997); nucleotides such as adenosine triphosphate (ATP) (Huizenga and Szostak, *Biochemistry*, 34:656-665, 1995); and guanine (Kiga et al., *Nucleic Acids Research*, 26:1755-60, 1998); co-factors such as NAD (Kiga et al., *Nucleic Acids Research*, 26:1755-60, 1998) and flavin (Lauhon and Szostak, *J. Am. Chem. Soc.*, 117:1246-57, 1995); antibiotics such as viomycin (Wallis et al., *Chem. Biol.* 4: 357-366, 1997) and streptomycin (Wallace and Schroeder, *RNA* 4:112-123, 1998); proteins such as HIV reverse transcriptase (Chaloin et al., *Nucleic Acids Research*, 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques*, 32: pp. 178-180 and 182-183, 2002); and bacterial spores such as the anthrax (Bruno and Kiel, *Biosensors & Bioelectronics*, 14:457-464, 1999). Aptamers are also available for other targets, including lysozyme, thrombin, human immunodeficiency virus trans-acting responsive element (HIV TAR), hemin, interferon γ, vascular endothelial growth factor (VEGF), prostate specific antigen (PSA) dopamine, and heat shock factor 1 (HSF1). In one example, the aptamer is specific for thrombin. Aptamers are also available for cells, such as cancer cells and bacteria. In addition, general strategies to design DNA aptazymes, by introducing aptamer motifs close to the catalytic core of DNAzymes, are available (Wang et al., *J. Mol. Biol.*, 318:33-43, 2002). In one example, a hemin-binding G-quadruplex DNAzyme is utilized.

Methods of Using Sensors to Detect Target Agents

The disclosed sensors can be used to detect a variety of targets, including nucleic acid molecules, proteins, cells, pathogens, small molecules such as metals and drugs, and the like. In some examples, the methods are multiplexed, for example by detecting multiple targets in a single sample, by using appropriate sensors specific for each target of interest. In some examples, multiple samples are analyzed simultaneously or contemporaneously. Samples that can be analyzed include biological, organic, and environmental samples.

Figure 2:
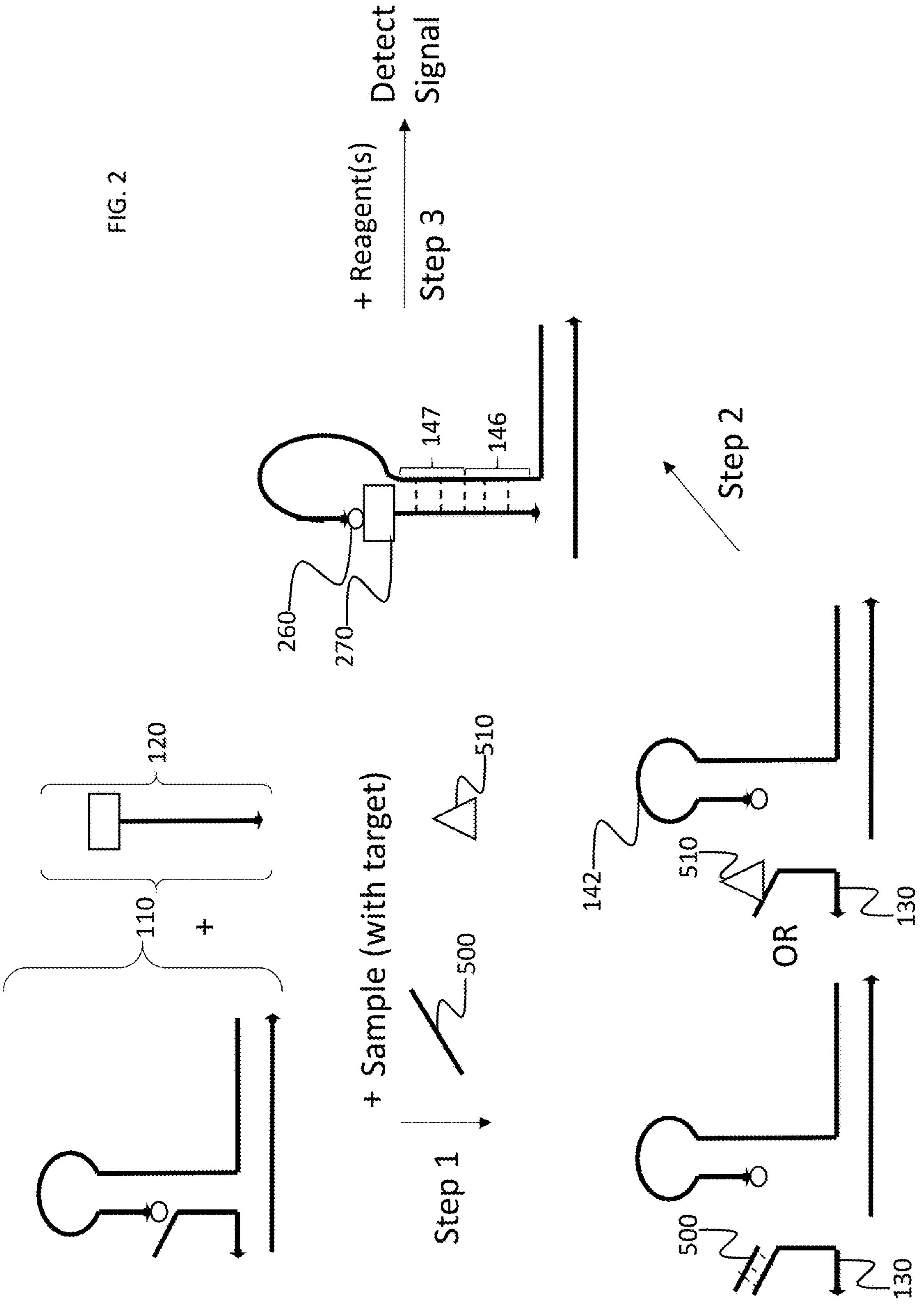
FIG. 2 is a schematic drawing showing an overview of the method for using exemplary sensor 100 (FIG. 1A) that includes trigger module 110 and sensory module 120 to detect a target agent (e.g., nucleic acid molecule 500 or small molecule 510 (such as a metal or drug)).
Figure 3:
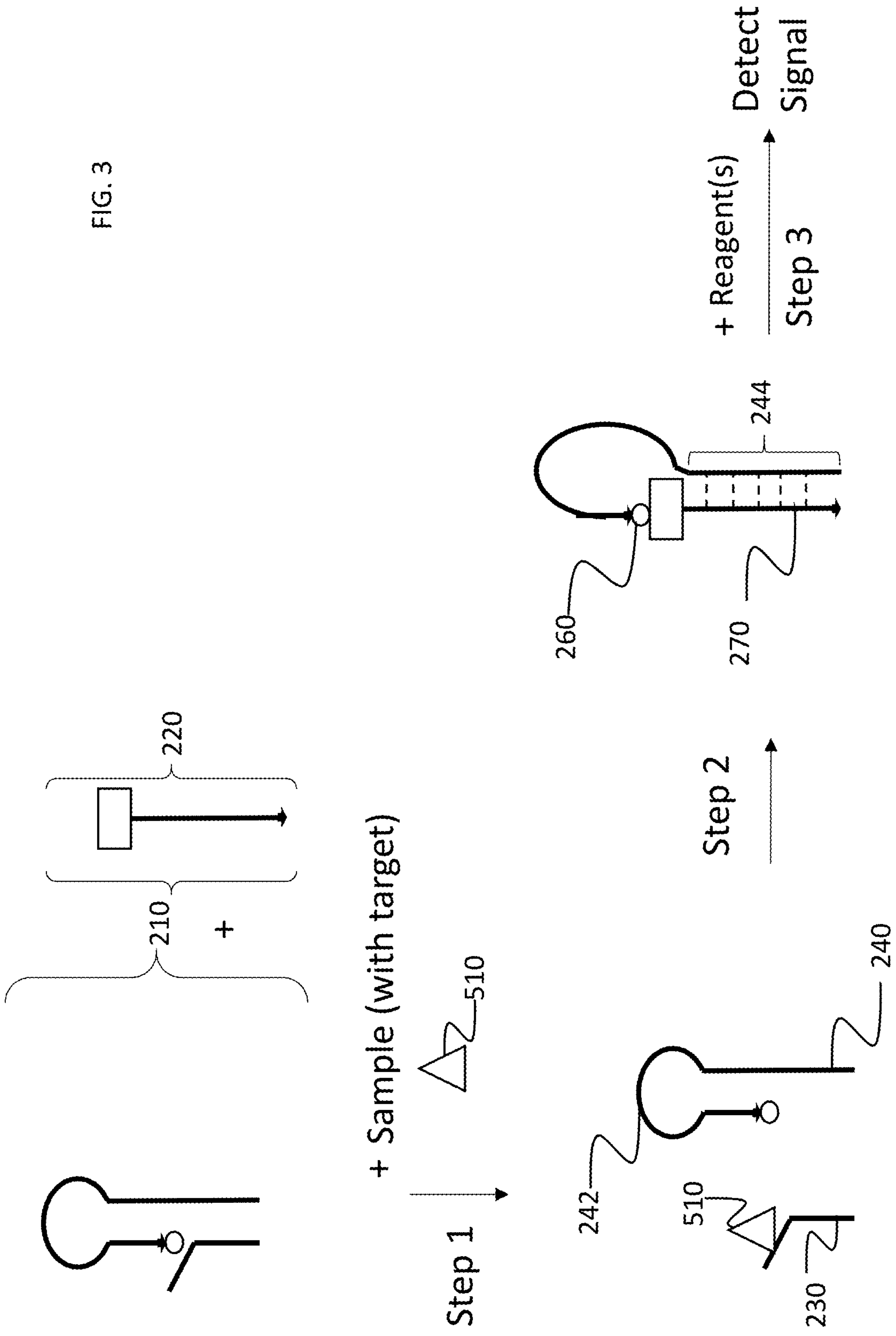
FIG. 3 is a schematic drawing showing an overview of the method for using exemplary sensor 200 (FIG. 1B) that includes trigger module 210 and sensory module 220 to detect a target agent (e.g., small molecule 510, such as a metal or drug).

Exemplary schematic overviews of the method are provided in FIGS. 2 and 3. FIG. 2 shows an example using sensor 100, while FIG. 3 shows an example using sensor 200. As shown in FIG. 2, at step 1, a sample (such as a biological or environmental or food sample), is contacted with the trigger module 110 and the sensory module 120 described above. The sample contains (or is thought to contain) the target, which can be a nucleic acid 500, or a small molecule 510 (such as a drug or metal). The sample is incubated with the trigger module 110 and the sensory module 120 under conditions that allow the target 500 or 510 to hybridize to (e.g., if the target is a nucleic acid molecule), or bind to (e.g., if the target is a small molecule 510), the nucleic acid molecule 130 of the trigger module 110 that has specificity for the target 500 or 510. The interaction (e.g., binding or hybridization) between the target 500, 510 with the nucleic acid molecule 130 of the trigger module 110 that has specificity for the target 500 or 510, results in a conformational change in the trigger module 110. As shown in Step 2, this conformation changes results in destabilization of the upper portion of the stem 147 (which was ds), which separates (e.g., is no longer ds and the trigger module 110 is no longer hybridized to itself) thereby opening the loop 142 of the trigger module 110. This conformational changes provides the sensory module 120 access to the stem region 147, 146 of the trigger module 110. The sensory module 120 can then hybridize to the stem region 147, 146 of the trigger module 110 due to the complementarity between the nucleic acid portion 170 of the sensory module 120 and the stem region 147, 146 of the trigger module 110, forming a ds nucleic acid molecule formed of the nucleic acid portion 170 of the sensory module 120 and the stem region 147, 146 of the trigger module 110. This brings the enzyme 180 of the sensory module 120 and the cofactor 160 of the trigger module 110 in close proximity, allowing the two to interact or bind to one another. As shown in Step 3, in the presence of the appropriate reagents (see examples in Table 3), activation of the enzyme 170 by the cofactor 160 results in the enzyme activating one or more reagents, to produce a visual signal that is detected. In some examples, the signal is a color or fluorescent signal, such as a change in color. Thus, if the target is present in the sample, a visual signal will be generated (e.g., change in color), while if the target is not present in the sample, no visual signal will be generated (e.g., no change in color).

As shown in FIG. 3, at step 1, a sample (such as a biological or environmental or food sample), is contacted with the trigger module 210 and the sensory module 220 described above. The sample contains (or is thought to contain) the target, which can be a small molecule 510 (such as a drug or metal). The sample is incubated with the trigger module 210 and the sensory module 220 under conditions that allow the target 510 to bind nucleic acid molecule 230 of the trigger module 210 that has specificity for target 510. The interaction (e.g., binding or hybridization) between the target 510 with the nucleic acid molecule 230 of the trigger module 210 that has specificity for the target 510, results in a conformational change in the trigger module 210. As shown in Step 2, this conformation changes results in destabilization of the upper portion of the stem 247 (which was ds), which separates (e.g., is no longer ds and the trigger module 210 is no longer hybridized to itself) thereby opening the loop 242 of the trigger module 210. This conformational changes provides the sensory module 220 access to the stem region 244 of the trigger module 210. The sensory module 220 can then hybridize to the stem region 244 of the trigger module 210 due to the complementarity between the nucleic acid portion 270 of the sensory module 220 and the stem region 244 (which includes 246 and part of 247) of the trigger module 210, forming a ds nucleic acid molecule formed of the nucleic acid portion 270 of the sensory module 220 and the stem region 244 of the trigger module 110. This brings the enzyme 280 of the sensory module 220 and the cofactor 260 of the trigger module 210 in close proximity, allowing the two to interact or bind to one another. As shown in Step 3, in the presence of the appropriate reagents (see examples in Table 3), activation of the enzyme 270 by the cofactor 260 results in the enzyme activating one or more reagents, to produce a visual signal that is detected. In some examples, the signal is a color or fluorescent signal, such as a change in color. Thus, if the target is present in the sample, a visual signal will be generated (e.g., change in color), while if the target is not present in the sample, no visual signal will be generated (e.g., no change in color).

It will be appreciated that the assays shown in FIGS. 2 and 3 can be performed in a single container or vial (such as a clear or transparent container/vial). For example, the container can include trigger module 110 or 210, sensory module 120 or 220, and the reagents needed to generate a visual signal. The sample is then simply added to the vial, where the reaction takes place, and the visual signal can be observed. In another example, the container can include trigger module 110 or 210 and sensory module 120 or 220. The sample and the reagents needed to generate a visual signal are added to the vial (in some examples contemporaneously, in some examples the sample followed by the reagents, or in some examples the reagents followed by the sample).

In some examples, the assay is performed in a liquid environment. That is, the reaction takes place in a buffer. For example, trigger module 110 or 210, sensory module 120 or 220, and the reagents are incubated in a liquid, for example in a vial or container (such as one that is transparent), and the sample added. The liquid buffer can be at pH 7-9, and the materials incubated at 4° C.-50° C., such as room temperature of about 25° C. In some examples, a detectable signal is produced in 1-60 mins.

Figure 4A:
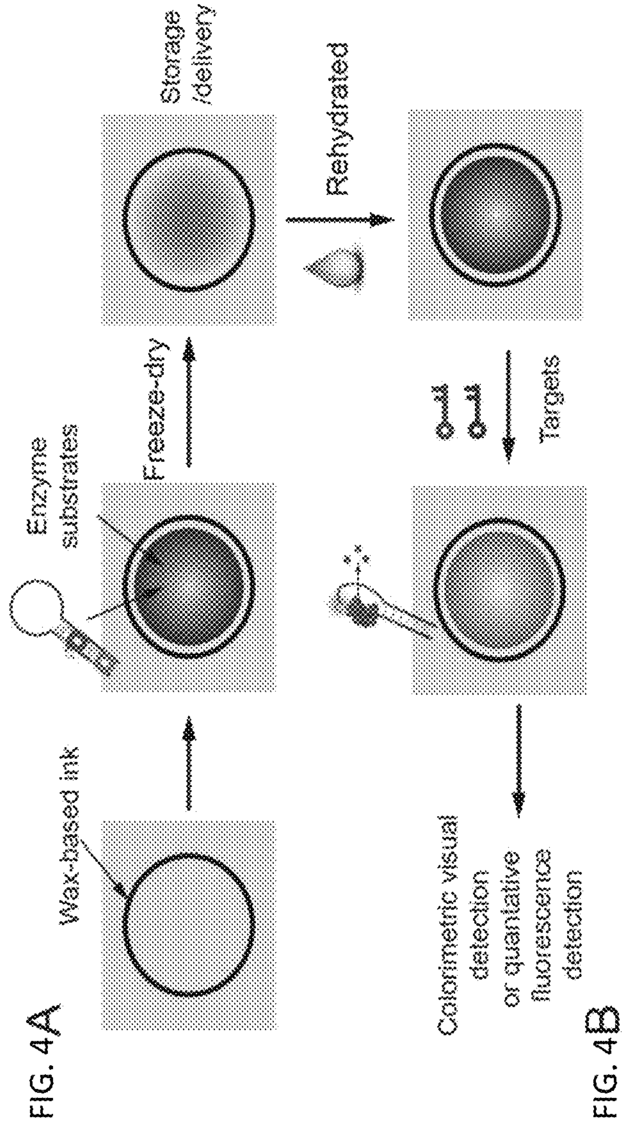
FIGS. 4A-4C demonstrate how the sensors provided herein can be used in a paper-based assay to detect a target. (A) The principle of preparing paper-based system and (B) the time-dependent color change of the resazurin assay from blue to pink within 15 mins. (C) Re-hydrated reaction for solution without NAD+(control) and the solution with NAD+.
Figure 4B:
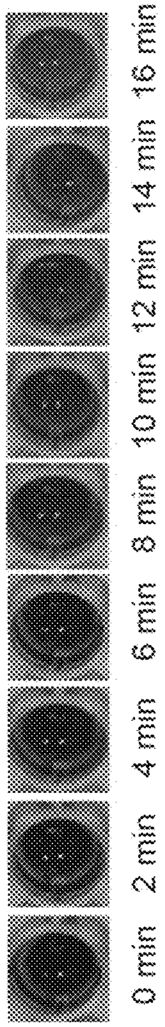
Figure 4C:
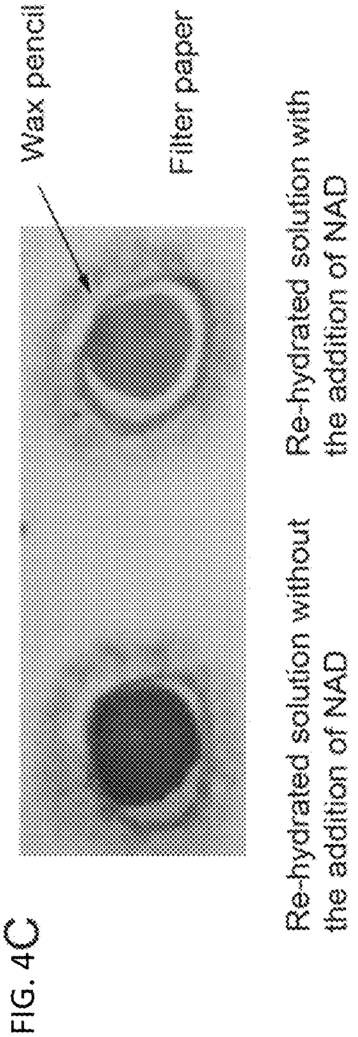

In some examples, the assay is performed on a solid support, such as paper or nitrocellulose. For example, the trigger module 110 or 210 and the sensory module 120 or 220 are applied to a solid support, such as paper or nitrocellulose, and dried. As shown in FIGS. 4A-4C, wax-based ink can be used to print out a hydrophobic boundary on a filter paper (e.g., cellulose-based). Droplets (a few to tens of μL) containing trigger module 110 or 210 and the sensory module 120 or 220 are added into the printed circle. Then, liquid on the paper is allowed to dry (e.g., freeze dried using a lyophilizer). The dried sensors may be more stable under storage. At the time of the assay, a few droplets of water or other appropriate buffer is added onto the paper to re-dissolve the trigger module 110 or 210 and the sensory module 120 or 220. The test sample can be added to the re-hydrated sensor, allowing recognition of target molecules in the sample, to produce a detectable signal (e.g., convert a blue-colored reasazurin to a pink-colored resorufin, as shown in FIG. 4B). In another example, trigger module 110 or 210, sensory module 120 or 220, and the reagents are applied to different areas of a solid support, such as a lateral flow strip. The sample is then added to the sample region of the solid support, where the sample travels along the solid support, interacting with the trigger module 110 or 210, the sensor module 120 or 210, and the reagents to produce a visual signal that can be observed. The liquid buffer can be at pH 7-9, and the materials incubated at 4° C.-50° C., such as room temperature of about 25° C. In some examples, a detectable signal is produced in 1-60 mins.

In one example, the method includes incubating or contacting the disclosed sensors (both the trigger module and the sensory module, e.g., 110 and 120 of FIG. 1A or 210 and 220 of FIG. 1B) with a sample, under conditions that allow a target in the sample to bind to the first portion of the first nucleic acid molecule that is specific for the target (e.g., 132 of FIG. 1D or 232 of FIG. 1G), thereby displacing the first nucleic acid molecule (e.g., 130 of FIG. 1A or 230 of FIG. 1B) from the second nucleic acid molecule (e.g., 140 of FIG. 1A or 240 of FIG. 1B). This results in a conformational change of the trigger molecule, which allows or permits the nucleic acid molecule of the sensory module (e.g., 170 of FIG. 1A or 270 of FIG. 1B) to hybridize to the first and second stem portion (e.g., 144 of FIG. 1D) of the second nucleic acid molecule (e.g., due to complementarity between the two nucleic acid molecules). This allows the enzyme and cofactor to assemble or bind to one another, and for the cofactor (e.g., 160 of FIG. 1D or 260 of FIG. 1H) to activate the enzyme (e.g., 180 of FIG. 1A or 280 of FIG. 1B). The resulting activated enzyme is allowed to interact with one or more reagents to produce a visual signal. The resulting visual signal is detected (for example by eye, for example with a POC device), wherein the production of a visual signal (such as a change of color) indicates the presence of the target agent in the sample. If no visual signal is produced (such as no change in color) this indicates that the target agent is not in the sample (e.g., the sample is negative).

The reagent that produces a visual signal can include multiple agents (e.g., one or more reagents), and can be matched to the enzyme. Non-limiting examples are shown in Table 3.

TABLE 3

Exemplary Reagents that produce a colorimetric or fluorescent read out

| Reagents | Enzyme | Visual Read Out |
|---|---|---|
| glucose 6-phosphate PMS (phenazine methosulfate) and resazurin | Glucose-6-phosphate dehydrogenase, NAD cofactor | resorufin (excitation max~ 544 nm, emission max~ 590 nm) or a visible color change from blue (resazurin) to pink (resorufin) |
| Glucose, PMS (phenazine methosulfate) and resazurin | Hexokinase, glucose-6-phosphate dehydrogenase, ATP cofactor | resorufin (excitation max~ 544 nm, emission max~ 590 nm) or a visible color change from blue (resazurin) to pink (resorufin) |
| Amplex Red, H2O2 | Hemin-binding G-quadruplex, hemin cofactor | Amplex red is converted to resorufin (excitation max~ 544 nm, emission max~ 590 nm) or a visible color change from clear (Amplex Red) to pink (resorufin) |

The reaction will happen in the buffer (e.g., one containing phosphate, Tris, HEPESS, or combinations thereof) from pH 7-9, and produce signals in 1-60 min at 4° C.-50° C. In one example, reaction happens at room temperature of about 25° C.

In some examples, the method includes amplifying the reaction using DNA hairpin assembly (see FIGS. 12A-12B, 13A-13C). For example, FIG. 13B provides an example wherein following binding of the target to the trigger module, and the change in conformation of the trigger module, this releases the target-specific nucleic acid molecule of the trigger module (e.g., 130 of FIG. 1A or 230 of FIG. 1B). This released nucleic acid molecule (trigger in FIGS. 13B and 13C) subsequently catalyzes the assembly of multiple hairpin structures (e.g., 140+120 in FIG. 1A or 240+220 in FIG. 1B, e.g., the structure before step 3 in FIGS. 2 and 3), which is used to assemble multiple copies of enzyme/cofactor pairs (e.g., a nanotube structure shown in FIG. 13B (which can be at least 40 nt, at least 48 nt, at least 50 nt, at least 100 nt, at least 200 nt, at least 300 nt, at least 400 nt, at least 500 nt, at least 600 nt, at least 700 nt, at least 800 nt, or at least 900 nt, such as 40 nt to 960 nt, 48 nt to 960 nt, 100 nt to 1000 nt, or 500 nt to 1000 nt), or short ds nucleic acid molecules (duplex), shown in FIG. 13C). The gain of the signaling module can be estimated as the product of the number of catalyzed hairpins assembly (N hairpin assembly) timing the enhancement fold of an enzyme/cofactor reaction (F enzyme/cofactor).

The sensors shown in FIGS. 16A-16C can be used to determine an activity of protein, such as a response to a particular concentration of reagents (e.g., response to glucose at a particular concentration). In one example, such a sensor is used to identify allosteric enzymes In one example, variants of a target protein can be part of the sensor moiety 320. For example protein 340 can be mutated or otherwise altered, and the sensor used to identify variant proteins having the desired activity. The variant protein 340 can be part of sensor 300, wherein the trigger module 310 includes an inhibitor 360 of the native protein. The sensor 300 is incubated with an appropriate molecule that activates the aptamer (such as ATP), and other reagents that the variant protein can act on. Variant proteins with increased activity can then be detected.

In one example, a sensor shown in FIGS. 16A-16C is used to determine the activity of an enzyme present on the sensory module. For example, the sensor containing the protein to be assayed is incubated with a molecule that specifically binds to the aptamer portion under conditions that permit that molecule bind to the aptamer portion, thereby separating the sensory module from the trigger module. For example, if the aptamer is specific for ATP, ATP is added. Separation of the sensory module from the trigger module also separates the inhibitor from the enzyme (e.g., removes the inhibitory effect on the enzyme), allowing the enzyme to have activity (or be activated). The activated enzyme can then be incubated with one or more reagents to produce a signal (such as a visual signal), which can be detected. Production of a signal indicates the activity of the enzyme, which in some examples is quantitative.

Samples

Any specimen that may contain (or is known to contain or is suspected of containing) a target agent can be used, including biological, organic, and environmental samples. Biological samples are typically obtained from a subject and can include genomic DNA, RNA (including mRNA and miRNA), proteins, or combinations thereof. Examples include a tissue or tumor biopsy, fine needle aspirate, bronchoalveolar lavage, cells, cell lysates, bone marrow, amniocentesis samples, circulating tumor cells, pleural fluid, spinal fluid, saliva, sputum, surgical specimen, lymph node fluid, ascites fluid, peripheral blood (such as serum or plasma), urine, saliva, vaginal swab, semen, buccal swab, and autopsy material. Serum or other blood fractions can be prepared in the conventional manner. Samples can also include fermentation fluid and tissue culture fluid.

Environmental samples include those obtained from an environmental media, such as water, air, soil, dust, wood, plants or food.

In other examples, a sample includes a control sample, such as a sample known to contain or not contain a particular target agent.

In one example the sample is a food sample, such as a meat, fruit, or vegetable sample. For example, using the methods provided herein, adulterants in food products can be detected, such as a pathogen or toxin or other harmful product.

The sample can be used directly, concentrated (for example by centrifugation or filtration), purified, liquefied, diluted in a fluid, or combinations thereof. In some examples, proteins or nucleic acids or pathogens are extracted from the sample, and the resulting preparation (such as one that includes isolated DNA and/or RNA) analyzed using the methods provided herein. In some examples, nucleic acid molecules in the sample are isolated, amplified (e.g., using PCR), reverse transcribed, or combinations thereof, prior to testing with the disclosed sensors and methods.

Target Agents

The disclosed sensors can be designed to detect any target agent of interest. Thus, the methods and devices provided herein can be used to detect any target agent of interest, such as the specific examples provided herein. Selecting an appropriate nucleic acid molecule specific for the target (e.g., 132 of FIG. 1D), allows one to develop a sensor that can be used to detect a particular target agent. Exemplary target agents are provided below; however one skilled in the art will appreciate that other target agents can be detected with the disclosed sensors and devices (such as a lateral flow device) using the disclosed methods. Exemplary target agents include metals, pathogens, small molecules (such as tetrahydrocannabinol cocaine, heroin, methamphetamine, or other recreational drugs, opiates and opioids (such as oxycodone), ethanol, nicotine, $UO_2^{2+}$, caffeine, or adenosine), proteins, (such as interferon-γ (IFN-γ)), cells, and nucleic acid molecules.

Metals

In one example the target agent is a metal (e.g., elements, compounds, or alloys that have high electrical conductivity), such as a heavy metal or a nutritional metal. Metals occupy the bulk of the periodic table, while non-metallic elements can only be found on the right-hand-side of the Periodic Table of the Elements. A diagonal line drawn from boron (B) to polonium (Po) separates the metals from the nonmetals. Most elements on this line are metalloids, sometimes called semiconductors. Elements to the lower left of this division line are called metals, while elements to the upper right of the division line are called non-metals.

Heavy metals include any metallic chemical element that has a relatively high density and is toxic, highly toxic or poisonous at low concentrations. Examples of heavy metals include mercury (Hg), cadmium (Cd), arsenic (As), chromium (Cr), thallium (Tl), uranium (U), plutonium (Pu), and lead (Pb).

Nutritional metal ions include those important in animal nutrition and may be necessary for particular biological functions, include calcium, iron, cobalt, magnesium, manganese, molybdenum, zinc, cadmium, and copper.

Aptamers specific for particular metals are known, such as those specific for metal ions such as $Hg^{2+}$ and $Cu^{2+}$ (e.g., Qu et al., *ACS Nano,* 10:7558-65, 2016), Zn(II) (Ciesiolka et al., *RNA* 1: 538-550, 1995) and Ni(II) (Hofmann et al., *RNA,* 3:1289-1300, 1997). Such aptamers can be used to generate a sensor of the disclosure (e.g., 132 of FIG. 1D).

Pathogens/Microbes

Any pathogen or microbe can be detected using the sensors and methods provided herein. For example, particular antimicrobial antigens (or antibodies generated therefrom) and nucleic acid molecules (such as DNA or RNA), as well as bacterial spores, can be detected. In some examples, a particular microbial cell is detected, or a particular virus. In some examples, intact microbes are detected, for example by detecting a target surface protein (such as a receptor) using sensors that include for example aptamers specific for the target protein, such as those specific for HIV reverse transcriptase (Chaloin et al., *Nucleic Acids Research,* 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques,* 32: pp. 178-180 and 182-183, 2002); and bacterial spores such as anthrax (Bruno and Kiel, *Biosensors & Bioelectronics,* 14:457-464, 1999). In other examples, a conserved DNA or RNA specific to a target microbe is detected, for example by obtaining nucleic acids from a sample (such as from a sample known or suspected of containing the microbe), wherein the resulting nucleic acids (such as DNA or RNA or both) are then contacted with the sensors disclosed herein (which include the complementary nucleic acid sequence that can hybridize to the target nucleic acid).

Exemplary pathogens include, but are not limited to, viruses, bacteria, fungi, nematodes, and protozoa. A non-limiting list of pathogens that can be detected using the sensors provided herein are provided below.

In one example, the target is a positive-strand or negative-strand RNA viruse. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain). Exemplary negative-strand RNA viruses include, but are not limited to: Orthomyxyoviruses (such as the influenza virus), Rhabdoviruses (such as Rabies virus), and Paramyxoviruses (examples of which include measles virus, respiratory syncytial virus, and parainfluenza viruses).

In one example the target is a DNA virus. DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

In one example the target is a Retrovirus. Examples of retroviruses include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In some examples, the virus detected with the disclosed methods is one or more of HIV (for example an HIV antibody, p24 antigen, or HIV genome); Hepatitis A virus (for example an Hepatitis A antibody, or Hepatitis A viral genome); Hepatitis B (HB) virus (for example an HB core antibody, HB surface antibody, HB surface antigen, or HB viral genome); Hepatitis C (HC) virus (for example an HC antibody, or HC viral genome); Hepatitis D (HD) virus (for example an HD antibody, or HD viral genome); Hepatitis E virus (for example a Hepatitis E antibody, or HE viral genome); a respiratory virus (such as influenza A & B, respiratory syncytial virus, human parainfluenza virus, or human metapneumovirus), Zika virus, Ebola virus, or West Nile Virus.

In some examples, the virus detected (e.g., nucleic acid or protein thereof) with the disclosed sensors is from one of the following genera (family): Dependovirus (Parvoviridae), Kobuvirus (Picornaviridae), Lyssavirus (Rhabdoviridae), Polyomavirus (Polyomaviridae), Seadornavirus (Reoviridae), Alphavirus (Togaviridae), Orthobunyavirus (Bunyaviridae), Orthobunyavirus (Bunyaviridae), Orthobunyavirus (Bunyaviridae), Lymphocryptovirus (Herpesviridae), Vesiculovirus (Rhabdoviridae), Alphavirus (Togaviridae), Cosavirus (Picornaviridae), Orthopoxvirus (Poxviridae), Enterovirus (Picornaviridae), Nairovirus (Bunyaviridae), Flavivirus (Flaviviridae), Thogotovirus (Orthomyxoviridae), Nairovirus (Bunyaviridae), Lys savirus (Rhabdoviridae), Alphavirus (Togaviridae), Ebolavirus (Filoviridae), Enterovirus (Picornaviridae), Cardiovirus (Picornaviridae), Lymphocryptovirus (Herpesviridae), Lyssavirus (Rhabdovirus), Pegivirus (Flaviviridae), Hantavirus (Bunyaviridae), Henipavirus (paramyxoviridae), Hepatovirus (picornaviridae), Orthohepadnavirus (Hepadnaviridae), Hepacivirus (Flaviviridae), Hepevirus (Unassigned), Deltavirus (Unassigned), Orthopoxvirus (Poxviridae), Mastadenovirus (Adenoviridae), Mamastrovirus (Astroviridae), Alphacoronavirus (Coronaviridae), Cytomegalovirus (Herpesviridae), Enterovirus (Picornaviridae), Simplexvirus (Herpesviridae), Simplexvirus (Herpesviridae), Roseolovirus (Herpesviridae), Roseolovirus (Herpesviridae), Rhadinovirus (Herpesviridae), Lentivirus (Retroviridae), Mupapillomavirus (Papillomaviridae), Alphapapillomavirus (Papillomaviridae), Alphapapillomavirus (Papillomaviridae), Respirovirus (Paramyxoviridae), Erythrovirus (Parvoviridae), Pneumovirus (Pneumoviridae), Enterovirus (Picornaviridae), Betacoronavirus (Coronaviridae), Spumavirus (Retroviridae), Deltaretrovirus (Retroviridae), Torovirus (Coronaviridae), Influenzavirus A (Orthomyxoviridae), Influenzavirus B (Orthomyxoviridae), Influenzavirus C (Orthomyxoviridae), Vesiculovirus (Rhabdoviridae), Polyomavirus (Polyomaviridae), Flavivirus (Flaviviridae), Arenavirus (Arenaviridae), Polyomavirus (Polyomaviridae), Flavivirus (Flaviviridae), Lyssavirus (Rhabdoviridae), Marburgvirus (Filoviridae), Flavivirus (Flaviviridae), Arenavirus (Arenaviridae), Norovirus (Caliciviridae), Flavivirus (Flaviviridae), Arenavirus (Arenaviridae), Arenavirus (Arenaviridae), Alphavirus (Togaviridae), Betacoronavirus (Coronaviridae), Morbilivirus (Paramyxoviridae), Cardiovirus (Picornaviridae), Polyomavirus (Polyomaviridae), Lyssavirus (Rhabdoviridae), Molluscipoxvirus (Poxviridae), Orthopoxvirus (Poxviridae), Rubulavirus (Paramyxoviridae), Flavivirus (Flaviviridae), Hantavirus (Bunyavirus), Henipavirus (Paramyxoviridae), Norovirus (Caliciviridae), Alphavirus (Togaviridae), Parapoxvirus (Poxviridae), Orthobunyavirus (Bunyaviridae), Arenavirus (Arenaviridae), Enterovirus (Picornaviridae), Phlebovirus (Bunyaviridae), Hantavirus (Bunyavirus), Lyssavirus (Rhabdoviridae), Phlebovirus (Bunyaviridae), Rosavirus (Picornaviridae), Alphavirus (Togaviridae), Rotavirus (Reoviridae), Rotavirus (Reoviridae), Rotavirus (Reoviridae), Rubivirus (Togaviridae), Alphavirus (Togaviridae), Salivirus (Picornaviridae), Phlebovirus (Bunyaviridae), Sapovirus (Caliciviridae), Alphavirus (Togaviridae), Hantavirus (Bunyavirus), Spumavirus (Retroviridae), Rubulavirus (Paramyxoviridae), Alphavirus (Togaviridae), Norovirus (Caliciviridae), Flavivirus (Flaviviridae), Flavivirus (Flaviviridae), Alphatorquevirus (Anelloviridae), Phlebovirus (Bunyaviridae), Phlebovirus (Bunyaviridae), Orthopoxvirus (Poxviridae), Varicellovirus (Herpesviridae), Orthopoxvirus (Poxviridae), Alphavirus (Togaviridae), Vesiculovirus (Rhabdoviridae), Alphavirus (Togaviridae), Polyomavirus (Polyomaviridae), Flavivirus (Flaviviridae), Orthopoxvirus (Poxviridae), Orthopoxvirus (Poxviridae), Flavivirus (Flaviviridae), and Flavivirus (Flaviviridae). In specific examples, the virus is an Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16,18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, or Zika virus.

In one example, the sensor can distinguish between an infectious versus a non-infectious virus.

In one example the target is a bacteria. Bacteria can be classified as gram-negative or gram-positive. Exemplary gram-negative bacteria include, but are not limited to: *Escherichia coli* (e.g., K-12 and O157:H7), *Shigella dysenteriae*, and *Vibrio cholerae*. Exemplary gram-positive bacteria include, but are not limited to: *Bacillus anthracis, Staphylococcus aureus, Listeria*, pneumococcus, gonococcus, and streptococcal meningitis. Examples of target bacteria whose nucleic acids or proteins can be detected with the disclosed methods, include without limitation: *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii biovar sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providen-*

*cia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes, Group A streptococci, Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio* furnisii), *Yersinia* sp. (such as *Yersinia enterocolitica, Yersinia pestis*, and *Yersinia pseudotuberculosis*) and *Xanthomonas maltophilia* among others.

In one example the target is a protozoa, nemotode, or fungi (e.g., target protozoa, nemotode, or fungal nucleic acid molecule or protein). Exemplary protozoa include, but are not limited to, *Plasmodium* (e.g., *Plasmodium falciparum* to diagnose malaria), *Leishmania, Acanthamoeba, Giardia, Entamoeba, Cryptosporidium, Isospora, Balantidium, Trichomonas, Trypanosoma* (e.g., *Trypanosoma brucei*), *Naegleria*, and *Toxoplasma*. Exemplary fungi include, but are not limited to, *Aspergillus* sp. (including *Aspergillus fumigatus*), *Candida* sp., (such as *Candida albicans*), *C. neoformans, C. gattii, Coccidioides* sp., *Coccidiodes immitis, Trichophyton* sp., *Microsporum* sp., *Epidermophyton* sp., *Tinea* sp., and *Blastomyces dermatitidis.*

In one example, bacterial spores are detected. For example, the genus of *Bacillus* and *Clostridium* bacteria produce spores that can be detected. Thus, *C. botulinum, C. perfringens, B. cereus*, and *B. anthracis* spores can be detected (for example detecting anthrax spores). One will also recognize that spores from green plants can also be detected using the methods and devices provided herein.

Proteins

The disclosed sensors and methods also permit detection of a variety of proteins, such as cell surface receptors, cytokines, antibodies, hormones, as well as toxins. In particular examples, the nucleic acid molecule that can specifically bind to the protein target is a functional nucleic acid. In some examples, a target protein is selected that is associated with a disease or condition, such that detection (or absence) of the target protein can be used to infer information (such as diagnostic or prognostic information for the subject from whom the sample is obtained) relating to the disease or condition.

In one example the protein detected is a cytokine. Cytokines are small proteins secreted by immune cells that have effects on other cells. Examples include interleukins (IL) and interferons (IFN), and chemokines, such as IL-1, IL-2, IL-4, IL-6, IL-8, IL-10, IFN-γ, IFN-β, transforming growth factor (TGF-β), and tumor necrosis factor (TNF)-α.

In one example the protein detected is a hormone. A hormone is a chemical messenger that transports a signal from one cell to another. Examples include plant and animal hormones, such as endocrine hormones or exocrine hormones. Particular examples include follicle stimulating hormone (FSH), human chorionic gonadotropin (hCG), thyroid stimulating hormone (TSH), growth hormone, progesterone, and the like.

In yet another example the protein detected is a toxin. Toxins are poisonous substances produced by cells or organisms, such as plants, animals, microorganisms (including, but not limited to, bacteria, viruses, fungi, rickettsiae or protozoa). Particular examples include botulinum toxin, ricin, diphtheria toxin, Shiga toxin, Cholera toxin, Staphylococcal enterotoxin B, and anthrax toxin. In another example, the toxin is an environmental toxin. In one example the toxin is a mycotoxin, such as: aflatoxin, citrinin, ergot alkaloids, patulin, fusarium toxins, or ochratoxin A. In one example the toxin is a cyanotoxin, such as: microcystins, nodularins, anatoxin-a, aplysiatoxins, cylindrospermopsins, lyngbyatoxin-a, and saxitoxins. In one example the toxin is an endotoxin, hemotoxin, necrotoxin, neurotoxin, or cytotoxin.

In one example, the target protein is a tumor-associated or tumor-specific antigen, such as CA-125 (ovarian cancer marker), alphafetoprotein (AFP, liver cancer marker); carcinoembryonic antigen (CEA; bowel cancers), BRCA1 and 2 (breast cancer), and the like.

In one example the target protein is a fertility-related biomarker, such as hCG, luteinizing hormone (LH), follicle-stimulating hormone (FSH), or fetal fibrinogen.

In one example the target protein is a diagnostic protein, such as prostate-specific antigen (PSA, for example GenBank Accession No. NP_001025218), C reactive protein, cyclic citrullinate peptides (CCP, for example to diagnose rheumatoid arthritis) or glycated hemoglobin (Hb A1c). In another example, the protein is one found on the surface of a target microbe or cell, such as a bacterial cell, virus, spore, or tumor cell. Such proteins, such as receptors, may be specific for the microbe or cell (for example HER2, IGF1R, EGFR or other tumor-specific receptor noted below in "nucleic acids"). In one example the protein is prostate-specific antigen (PSA, for example GenBank Accession No. NP_001025218).

Nucleic Acids

The disclosed sensors also permit detection of nucleic acid molecules, such DNA and RNA, such as a DNA or RNA sequence that is specific for a particular pathogen or cell of interest. For example, target pathogens can have conserved DNA or RNA sequences specific to that pathogen (for example conserved sequences for Zika, Ebola, HIV, bird flu and swine flu), and target cells may have specific DNA or RNA sequences unique to that cell, or provide a way to distinguish a target cell from another cell (such as distinguish a tumor cell from a benign cell).

In some examples, a target sequence is selected that is associated with a disease or condition, such that detection of hybridization between the target nucleic acid and a sensor provided herein can be used to infer information (such as diagnostic or prognostic information for the subject from whom the sample is obtained) relating to the disease or condition.

In specific non-limiting examples, a target nucleic acid sequence associated with a tumor (for example, a cancer) is selected. Numerous chromosome abnormalities (including translocations and other rearrangements, reduplication (amplification) or deletion) have been identified in neoplastic cells, especially in cancer cells, such as B cell and T cell leukemias, lymphomas, breast cancer, colon cancer, neurological cancers and the like.

Exemplary target nucleic acids include, but are not limited to: the SYT gene located in the breakpoint region of chromosome 18q11.2 (common among synovial sarcoma soft tissue tumors); HER2, also known as c-erbB2 or HER2/neu (a representative human HER2 genomic sequence is provided at GENBANK™ Accession No. NC_000017, nucleotides 35097919-35138441) (HER2 is amplified in human breast, ovarian, gastric, and other cancers); p16 (including D9S1749, D9S1747, p16(INK4A), p14(ARF), D9S1748, p15(INK4B), and D9S1752) (deleted in certain bladder cancers); EGFR (7p12; e.g., GENBANK™ Accession No. NC_000007, nucleotides 55054219-55242525), MET (7q31; e.g., GENBANK™ Accession No. NC_000007, nucleotides 116099695-116225676), C-MYC (8q24.21; e.g., GENBANK™ Accession No. NC_000008, nucleotides 128817498-128822856), IGF1R (15q26.3; e.g., GENBANK™ Accession No. NC_000015, nucleotides 97010284-97325282), D5S271 (5p15.2), KRAS (12p12.1; e.g. GENBANK™ Accession No. NC_000012, complement, nucleotides 25249447-25295121), TYMS (18p11.32; e.g., GENBANK™ Accession No. NC_000018, nucleotides 647651-663492), CDK4 (12q14; e.g., GENBANK™ Accession No. NC_000012, nucleotides 58142003-58146164, complement), CCND1 (11q13, GENBANK™ Accession No. NC_000011, nucleotides 69455873-69469242), MYB (6q22-q23, GENBANK™ Accession No. NC_000006, nucleotides 135502453-135540311), lipoprotein lipase (LPL) (8p22; e.g., GENBANK™ Accession No. NC_000008, nucleotides 19840862-19869050), RB1 (13q14; e.g., GENBANK™ Accession No. NC_000013, nucleotides 47775884-47954027), p53 (17p13.1; e.g., GENBANK™ Accession No. NC_000017, complement, nucleotides 7512445-7531642), N-MYC (2p24; e.g., GENBANK™ Accession No. NC_000002, complement, nucleotides 15998134-16004580), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), aALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054-69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994017-28026515); Fill (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89718512), AKT2 (19q13.1-q13.2; e.g., GENBANK™ Accession No. NC_000019, complement, nucleotides 45428064-45483105), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In examples where the target molecule is a nucleic acid molecule, the sample to be tested can be treated with agents that permit disruption of the cells or pathogen. The nucleic acid molecules can be extracted or isolated, and then exposed to a sensor disclosed herein containing a sequence that is complementary to the target DNA or RNA sequence, such that the complementary nucleic acid sequence can hybridize to the target nucleic acid, thereby permitting detection of the target nucleic acid.

Recreational and Other Drugs

The disclosed sensors also permit detection of a variety of drugs, such as pharmaceutical or recreational drugs, for example wherein the trigger module 110 includes a nucleic acid (such as a functional nucleic acid) specific for the drug (e.g., 132 of FIG. 1D is specific for the drug). For example, the presence of caffeine, cocaine, opiates and opioids (such as oxycodone), cannabis (for example by detecting tetrahydrocannabinol (THC)), heroin, methamphetamines, crack, ethanol, acetaminophen, benzodiazepines, methadone, phencyclidine, or tobacco (for example by detecting nicotine), can be detected using the disclosed sensors and devices. In one example, the target is a therapeutic drug, such as theophylline, methotrexate, tobramycin, cyclosporine, rapamycin, or chloramphenicol.

Cells

The disclosed sensors also permit detection of a variety of cells, such as tumor or cancer cells, as well as other diseased cells. In on example, the sensor can distinguish between a tumor cell and a normal cell of the same cell type, such as a normal breast cell from a cancerous breast cell. Tumors are abnormal growths which can be either malignant or benign, solid or liquid (for example, hematogenous). In some examples, cells are detected by using a sensor that includes a nucleic acid (such as a functional nucleic acid) specific for a surface or other protein associated with the cell (e.g., 132 of FIG. 1D is specific for the protein), such as a receptor on the surface of the cell. In some examples, cells are detected by using a sensor that includes a nucleic acid specific for (e.g., complementary to) a nucleic acid molecule associated with the cell (e.g., 132 of FIG. 1D is specific for the nucleic acid target associated with the cell), such as a tumor specific nucleic acid molecule or a bacterial specific nucleic acid molecule.

Examples of hematological tumors (or cells) that can be detected with the disclosed sensors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenstrom's macroglobulinemia, heavy chain disease, myelodysplastic syndrome, mantle cell lymphoma and myelodysplasia.

Examples of solid tumors, such as sarcomas and carcinomas, that can be detected with the disclosed sensors include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Compositions and Kits

The disclosure also provides compositions and kits that include one or more of the sensors disclosed herein, for example sensors that are in a liquid (such as water or a buffer), as well as sensors that are immobilized on a solid support (such as paper or part of a lateral flow device). For example, a kit can include at least 2 different sensors permitting detection of at least two different target agents, such as at least 3, at least 4, at least 5, or at least 10 different sensors. In a specific example, a kit can include at least 2 different solid supports permitting detection of at least two different target agents, such as at least 3, at least 4, at least 5, or at least 10 different solid supports.

In one example, a liquid composition includes one or more sensors, and water, saline, or a liquid buffer. In some examples, the buffer includes Tris saline, HEPEss, or combinations thereof. In one example, a composition includes one or more sensors immobilized on a solid support, such as one that is part of a lateral flow device. In one example, the solid support is paper. In some examples, such a composition is generated by applying a liquid composition that includes one or more sensors to the solid support, and drying the liquid, thereby immobilizing the one or more sensors.

In addition to the sensors, the kits can include one or more color detection reagents, such as one or more of glucose-6-phosphate, phenazine methosulfate, resazurin, amplex red, and $H_2O_2$.

The kit can include a vial or solid support containing one or more of the sensors disclosed herein and a separate vial or solid support containing the one or more color detection reagents. Or the one or more of the sensors disclosed herein and the one or more color detection reagents can be present in the same vial or solid support.

The sensor of the kit can be present in a vial, tube, box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control sample containing the target agent), diluents (such as, water, phosphate buffers, or saline buffers).

The kit can further include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain droppers, Dispo-pipettes, capillary tubes, rubber bulbs (e.g., for capillary tubes), and the like. Still other kit embodiments may include disposal means for discarding a used device and/or other items used with the device (such as patient samples, etc.). Such disposal means can include, without limitation, containers that are capable of containing leakage from discarded materials, such as plastic, metal or other impermeable bags, boxes or containers.

In some examples, a kit will include instructions for the use.

Solid Supports

In some examples, one or more sensors are immobilized on a solid support. The solid support can be formed from a water immiscible material. The surface of a solid support may be activated by chemical processes that cause covalent linkage of an agent (e.g., a nucleic acid molecule specific for the target) to the support. However, any other suitable method may be used for immobilizing an agent (e.g., a nucleic acid molecule specific for the target) to a solid support including, without limitation, ionic interactions, hydrophobic interactions, covalent interactions and the like.

In one example the solid support is a particle, such as a bead. Such particles can be composed of metal (e.g., gold, silver, platinum), metal compound particles (e.g., zinc oxide, zinc sulfide, copper sulfide, cadmium sulfide), non-metal compound (e.g., silica or a polymer), as well as magnetic particles (e.g., iron oxide, manganese oxide). In some examples the bead is a latex, agarose resin, or glass bead.

In another example, the solid support is a bulk material, such as a paper, membrane, porous material, water immiscible gel, water immiscible ionic liquid, water immiscible polymer (such as an organic polymer), and the like. For example, the solid support can comprise a membrane, such as a semi-porous membrane that allows some materials to pass while others are trapped. In one example the membrane comprises nitrocellulose. In a specific example the solid support is part of a lateral flow device that includes a region containing the sensors disclosed herein.

In some embodiments, porous solid supports, such as nitrocellulose, are in the form of sheets or strips, such as those found in a lateral flow device. The thickness of such sheets or strips may vary within wide limits, for example, at least 0.01 mm, at least 0.1 mm, or at least 1 mm, for example from about 0.01 to 5 mm, about 0.01 to 2 mm, about 0.01 to 1 mm, about 0.01 to 0.5 mm, about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm).

In one example, the solid support is composed of an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof).

In yet other examples, the solid support is a material containing, such as a coating containing, any one or more of or a mixture of the ingredients provided herein.

The solid support can be any format to which the molecule specific for the test agent can be affixed, such as microtiter plates, ELISA plates, test tubes, inorganic sheets, dipsticks, lateral flow devices, and the like. One example includes a linear array of molecules specific for the target agent, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range.

In another example the format is filter paper. In yet another example the format is a glass slide. In one example, the solid support is a polypropylene thread. One or more polypropylene threads can be affixed to a plastic dipstick-type device; polypropylene membranes can be affixed to glass slides.

In one example the solid support is a microtiter plate. For example sensors can be affixed to the wells of a microtiter plate (for example wherein some wells can contain a sensor to detect target X, while other wells can contain a sensor to detect target Y; or several wells might include the same sensor, wherein multiple samples can be analyzed simultaneously). The test sample potentially containing a target of interest can be placed in the wells of a microtiter plate containing a sensor disclosed herein, and the presence of the target detected using the methods provided herein in.

Each of the supports and devices discussed herein (e.g., ELISA, lateral flow device) can be, in some embodiments, formatted to detect multiple targets by the addition of sensors specific for the other targets of interest. For example, certain wells of a microtiter plate can include sensors specific for the other targets of interest. Some lateral flow device embodiments can include secondary, tertiary or more capture areas containing sensors specific for the other targets of interest.

Lateral Flow Devices

In one example, the solid support is a lateral flow device, which can be used to determine the presence and/or amount of one or more target agents in a fluid sample. A lateral flow device is an analytical device having a test strip, through which flows a test sample fluid that is suspected of (or known to) containing a target agent. Based on the principles of a pregnancy strip, lateral flow devices that incorporate the disclosed sensors can be developed. In some examples, by using such as lateral flow devices, samples can be directly contacted with or applied to the lateral flow device, and no further liquid transfer or mixing is required. Such devices can be used to detect target agents, for example qualitatively or quantitatively.

Lateral flow devices are known, and have a wide variety of physical formats. Any physical format that supports and/or houses the basic components of a lateral flow device in the proper function relationship is contemplated by this disclosure. In one example, the lateral flow devices disclosed in U.S. Pat. No. 7,799,554, Liu et al. (*Angew. Chem. Int. Ed.* 45:7955-59, 2006), Apilux et al. (*Anal. Chem.* 82:1727-32, 2010), Dungchai et al. (*Anal. Chem.* 81:5821-6, 2009), or Dungchai et al. (*Analytica Chemica Acta* 674:227-33, 2010) are used, such as one made using the Millipore Hi-Flow Plus Assembly Kit. There are a number of commercially available lateral flow type tests and patents disclosing methods for the detection of large analytes (MW greater than 1,000 Daltons) (see for example U.S. Pat. Nos. 5,229,073; 5,591,645; 4,168,146; 4,366,241; 4,855,240; 4,861,711; and 5,120,643; European Patent No. 0296724; WO 97/06439; and WO 98/36278). There are also lateral flow type tests for the detection of small-analytes (MW 100-1,000 Daltons) (see for example U.S. Pat. Nos. 4,703,017; 5,451,504; 5,451,507; 5,798,273; and 6,001,658).

The construction and design of lateral flow devices is known, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810.

A lateral flow device can be used to detect a plurality of different target agents in a single sample.

Example 1

DNA Nanosensors

One exemplary design of the sensor includes the integration of the following functions: (1) a sensing module to induce conformational switch (i.e., trigger module 110 in FIG. 1A); (2) an assembly module (i.e., sensor module 120 in FIG. 1A) that is triggered by the sensing module to assemble enzyme/cofactor pair; (3) an easy-to-read detection platform. As shown in FIG. 6A, the design is based on DNA-mediated proximity interaction of an enzyme/cofactor assembly: the catalytic cofactor (e.g., β-nicotinamide adenine dinucleotide, NAD+; adenosine triphosphate, ATP) is first locked into a DNA nanostructure with little accessibility to enzymes (almost no activity). The locked cofactor has little accessibility to enzymes with almost no activity. The opened hairpin allows a cofactor to interact with or allows access to enzymes, but with low activity due to the poor mass transport in solution. To actuate biochemical reaction, the enzyme and cofactor are co-assembled onto a double stranded DNA (dsDNA) scaffold with proximity-boosted activities (e.g., 100-fold more) due to the close proximity between an enzyme/cofactor pair, as well as facilitated substrate channeling.

A logic-gated cofactor arm (e.g., 132 in FIG. 1D) is used, which is regulated by target binding-triggered structural DNA switches, such as toehold displacement or aptamer switch. The DNA-target binding induces a structural cascade to direct the assembly of enzymes and its cofactor arms on DNA scaffolds. Then, the assembled enzyme/cofactor complex actuates a biochemical reaction to produce detectable signals. To provide an easy-to-read detection platform, the assembled enzyme/cofactor pair is used to catalyze a reaction with the production of fluorescence or visible color signals, which can be further applied to a paper-based detection system.

As shown in FIG. 6B, a co-assembled enzyme/cofactor pair (glucose-6-phosphate dehydrogenase (G6PDH) and NAD+) was 100-fold more active than a DNA hairpin-locked cofactor and was also higher than a partially hairpin-opened cofactor and a fully exposed cofactor. Enzyme activity was analyzed by the slope value of reaction curves, which indicated the speed of a reaction. This result provided a foundation for designing a biochemical sensing circuit, in which a sensing module of DNA structural switches is used to trigger the assembly of an enzyme/cofactor pair to catalyze a reaction for producing detectable signals (FIG. 6C).

Example 2

The Catalytic Enzyme/Cofactor System

Figure 7:
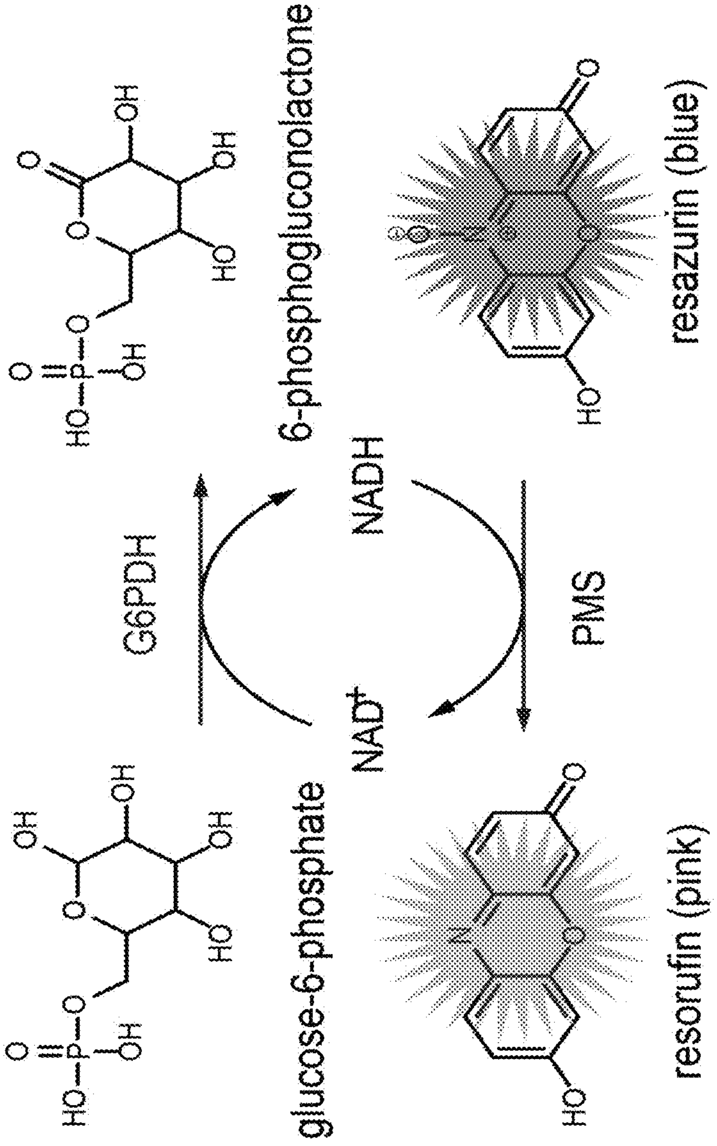
FIG. 7 is a schematic showing a PMS-resazurin coupled assay for detecting the activity of G6pDH and NAD+ cofactor.

As shown in FIG. 7, an exemplary simple catalytic system includes glucose 6-phosphate dehydrogenase (G6pDH) and its corresponding NAD+ cofactor. G6pDH (homodimeric, ~100 kDa) catalyzes the oxidation of glucose 6-phosphate to 6-phosphogluconolactone, while concurrently reducing NAD+ to NADH with a turnover rate of ~700 $s^{-1}$. The dehydrogenase cascade channeled by a NAD+ swinging arm was almost 100-fold more active than free pair of enzyme and cofactors. The actuated G6pDH/NAD+ pair can catalyze a coupled assay of PMS (phenazine methosulfate) and resazurin, which converts resazurin to strongly fluorescent resorufin (excitation max ~544 nm, emission max ~590 nm). The assay is also colorimetric with visible color change from blue (resazurin) to pink (resorufin).

Example 3

DNA-Locked Cofactor

Figure 8B:
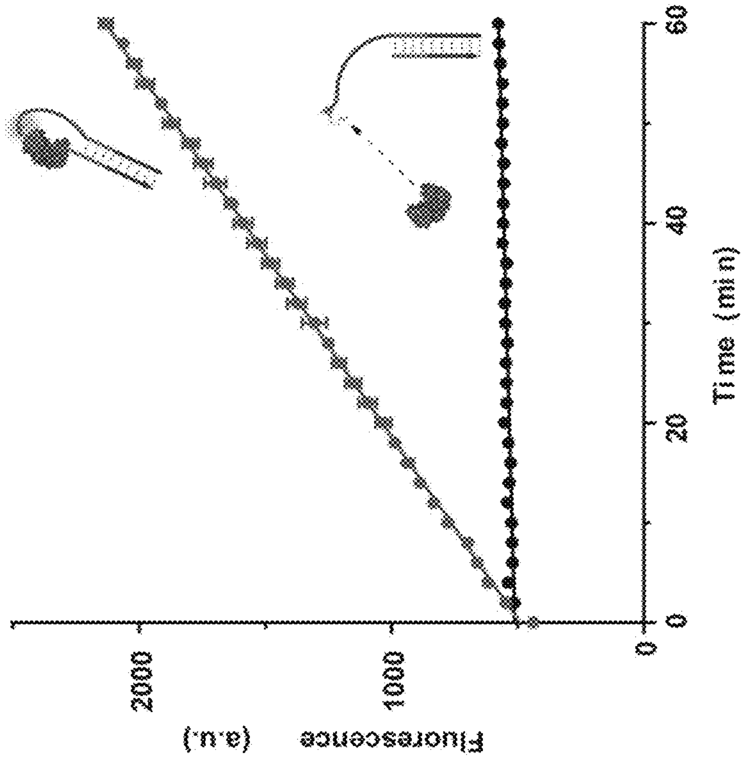
FIGS. 8A-8B: (A) Activities of locked NAD+, partially opened NAD+ and opened NAD+. (B) Actuated reaction by assembling together an enzyme/cofactor pair as compared with a freely diffused enzyme/cofactor pair (black line).
Figure 8A:
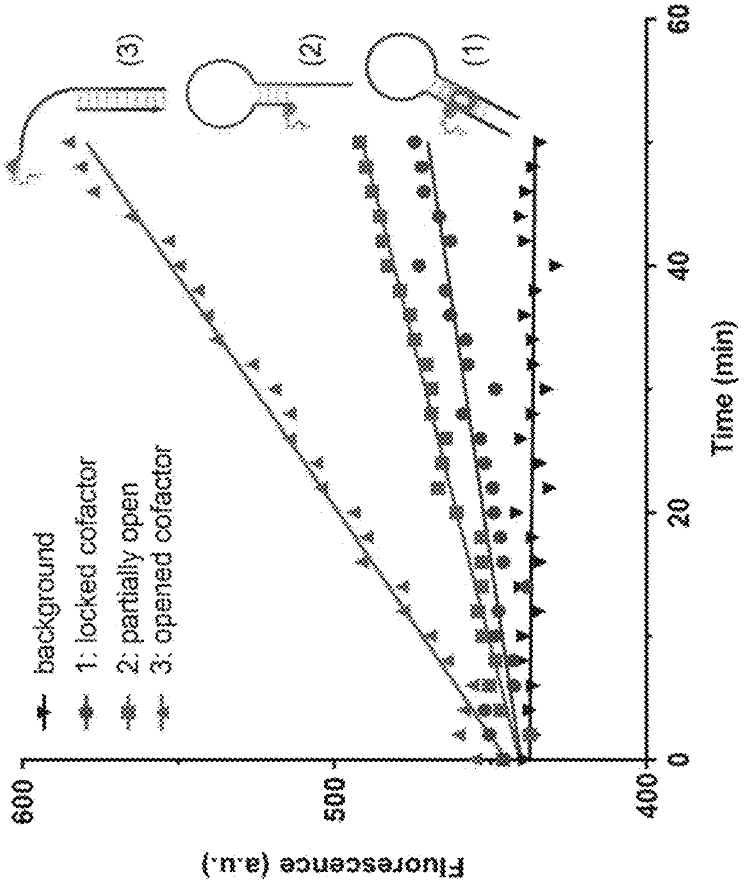

As shown in FIGS. 8A-8B, a DNA-locked NAD+ structure was generated and tested where the cofactor was folded within a DNA hairpin. The locked cofactor (structure (1) in FIG. 8A) arm had little accessibility to an enzyme (glucose-6-phosphate dehydrogenase, G6pDH) with very low activity. As DNA switch triggered the opening of this cofactor arm, the corresponding activities were increased to ~1.7-fold more for a partially opened cofactor arm (structure (2)) and ~5-fold more for a fully opened cofactor arm (structure (3)). To further actuate the enzyme/cofactor reaction, the opened cofactor is assembled with a G6pDH enzyme (FIG. 8B), which catalyzed the production of a strongly fluorescent resorufin, 1 producing 30-fold more activity as compared with unassembled enzyme and cofactor. Combining results in FIG. 8A and FIG. 8B, the overall enhanced activity for an assembled enzyme/cofactor pair is >150-fold of that for the locked cofactors.

Example 4

DNA Binding-Triggered Assembly of Enzyme/Cofactor Pair

A DNA logic-gated assembly of an enzyme/cofactor pair was designed. As shown in FIG. 9A, a DNA hairpin structure is composed of a toehold strand (I), a hairpin strand (II), and a base strand (III). An enzyme cofactor is conjugated to the 5' end of the hairpin strand. A trigger strand (I') hybridizes with the exposed toehold region (green) of the strand (I) and displaces it from the hairpin. Then, an enzyme conjugated with a strand (II') recognizes the newly exposed region and hybridizes with the hairpin strand (II) to produce a co-assembled enzyme/cofactor. The overall assembly is controlled by an AND gate with the inputs of both a trigger strand (I') and a sensing enzyme (II').

The assembly of DNA logic-gated structure was characterized by polyacrylamide gel electrophoresis (PAGE). The base strand (III) was used to stabilize the hybridization of a toehold strand (I) and a hairpin strand (II) and to reduce the nonspecific co-assembly of an enzyme and a cofactor. To optimize the performance, the length of the hairpin loop was varied from 3 T to 20 T. As shown in FIG. 9B, the loop length d from 6 T to 12 T gave the highest activity for the co-assembled enzyme/cofactor pair. Thus, in some examples, the loop region of a sensor provided herein is 6 to 12 nt. An optimized length of a ssDNA-linked cofactor provides the flexibility for mapping the enzyme surface to reach the active site but does not significantly decrease the local cofactor concentration.

Figure 10A:
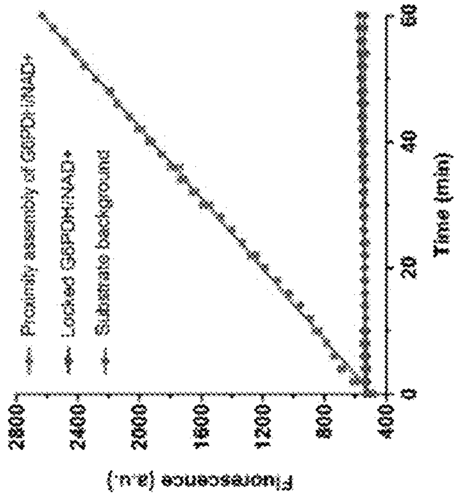
FIGS. 10A-10C: The DNA logic-gated assembly was used to mediate (A) a glucose-6-phosphate dehydrogenase (G6PDH)/NAD+ pair, (B) a hexokinase (HEK)/ATP pair and (C) a G-quadruplex/hemin complex. Error bar: range of data from three replicates.
Figure 10B:
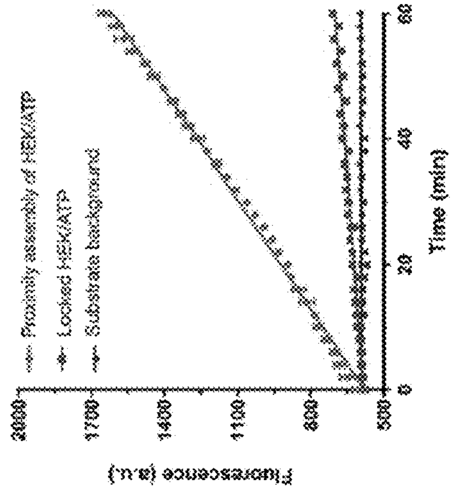
Figure 10C:
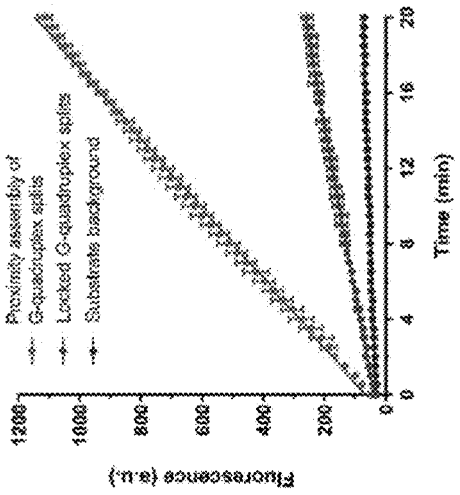

To test the versatility, the DNAlocked cofactor was used to mediate multiple biochemical reactions, including a G6PDH/NAD+ pair (FIG. 10A, ca. 53-fold enhancement) and a hexokinase (HEK)/ATP pair (FIG. 10B, ca. 10-fold enhancement). The assembly of a complete G-quadruplex/hemin pair to from two split halves was tested (FIG. 10C, ca. 5.6-fold enhancement). Among these reactions, the G6PDH/NAD+ assembly gave the highest activity enhancement (>50-fold). Thus, this enzyme/cofactor system was chosen for studies of the sensing of biochemical targets.

It is also possible to use other enzyme/cofactor systems, such as FAD-dependent glucose oxidase, FAD dependent glucose dehydrogenase, and FMN-dependent diaphorase.

Example 5

Aptamer Switch-Triggered Assembly of Enzyme/Cofactor Pair

Figures 11A, 11B, 11C:
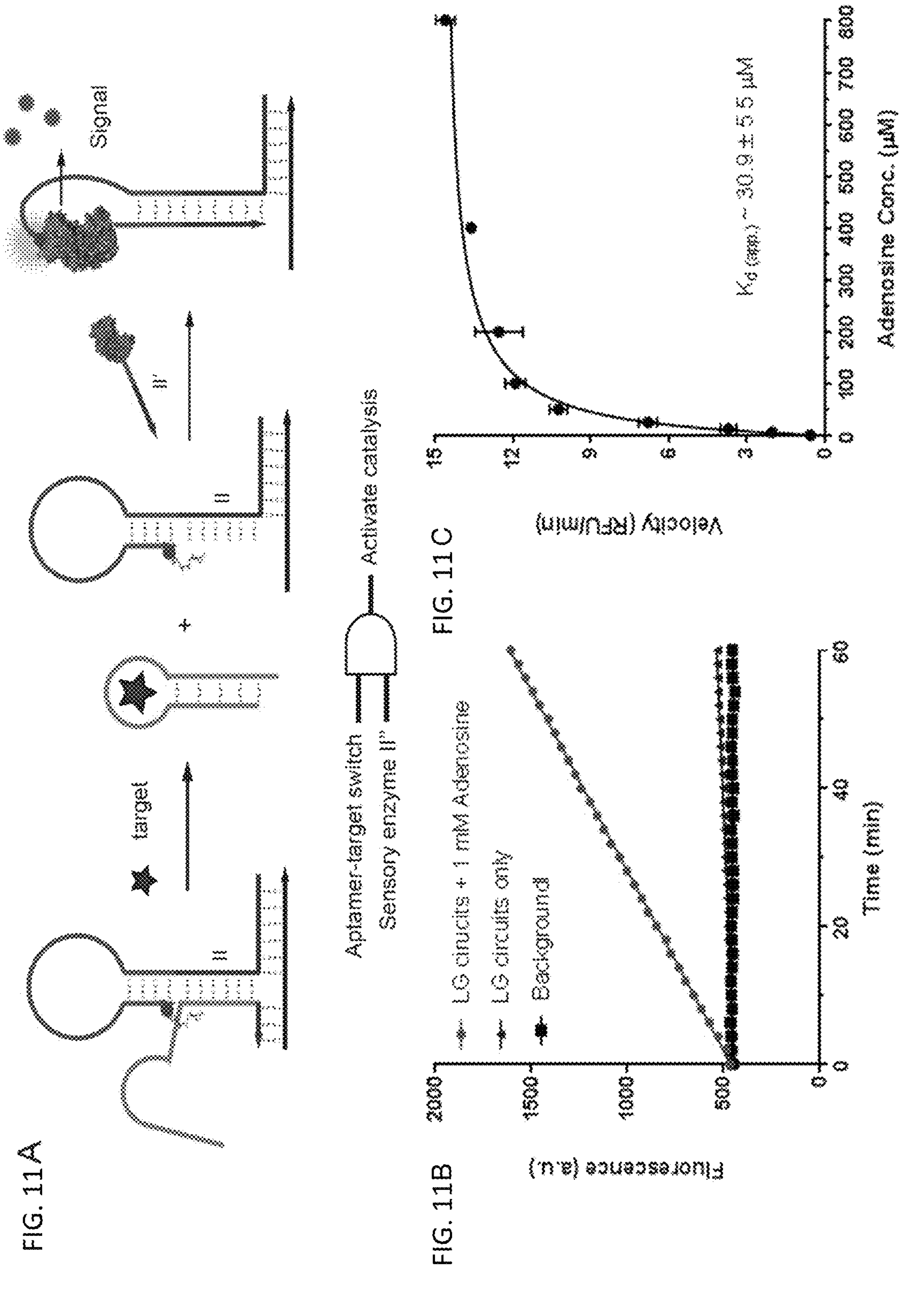
FIGS. 11A-11C: (A) Aptamer switch-triggered assembly of enzyme/cofactor pair. Detection of adenosine (B) and titration of the apparent dissociate constant (C).

An aptamer-complement duplex was used to lock a NAD cofactor within the hairpin structure (FIG. 11A). The presence of the target disrupts the aptamer-complement duplex, allowing the aptamer to re-fold into the aptamer-target binding conformation. This will expose a toehold (II) for the subsequent assembly of an enzyme/cofactor pair. For proof of concept, an adenosine-binding aptamer was incorporated into DNA structures for locking a NAD. One skilled in the art will appreciate that other aptamers specific for other targets can be used, such as one specific for a protein (e.g., thrombin), or a metal ion (e.g., $Mg^{2+}$, $Zn^{2+}$).

As shown in FIG. 11B, the addition of 1 mM adenosine actuated the biochemical reaction with the triggered assembly of enzyme/cofactor pair. In FIG. 11C, the adenosine concentrations were titrated for actuating the enzyme/cofactor circuit, with an apparent Kd value against adenosine of about 31 μM.

Example 6

DNA Hairpin Assembly Circuit of Amplifying Enzyme/Cofactor Nanostructures

Figure 12A:
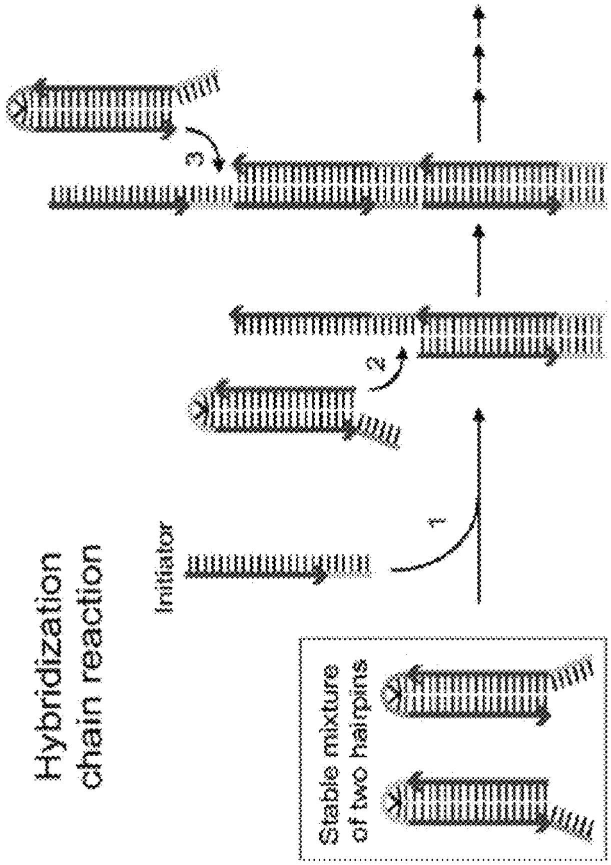
FIGS. 12A-12B. (A) HCR assembly and (B) CHA circuit for amplifying product.
Figure 12B:
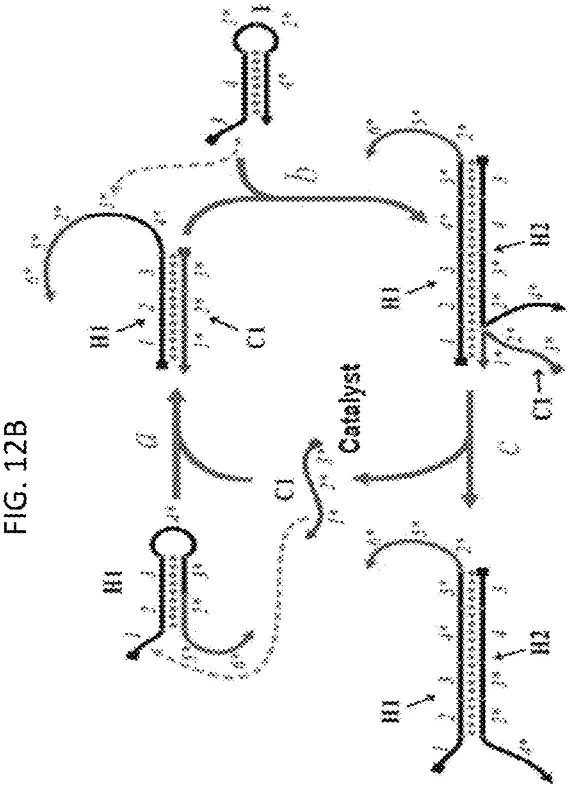

DNA hairpin assembly circuit is an enzyme-free amplification method used to amplify, transduce and assemble nucleic acids structures and signals (Jiang et al., *J. Am Chem Soc* 2013, 135:7430-3). In FIG. 12A, the DNA hybridization chain reaction (HCR) (Dirks et al., *Proc Nat Acad Sci* 2004, 101:15275-8; Evanko, *Nat Meth* 2004, 1:186-187) is a method wherein two stable DNA hairpin monomers assemble together into a long DNA duplex upon the triggering of an single-stranded DNA (ssDNA) initiator. In FIG. 12B, the catalytic hairpin assembly (CHA) circuit is developed to amplify a short double-stranded DNA (dsDNA) product with using a ssDNA catalyst and two hairpin substrates. The dsDNA products further release fluorescence signals by strand displacement with the fluorophore-quenched reporter strands (Li et al., *Nucleic Acids Res* 2011, 39:e110; Yin et al., *Nature* 2008, 451:318-22).

Example 7

Method of Detection

Since its mixture with the enzyme and the substrate shows low activity in the absence of the trigger, the DNA hairpin-locked cofactor can be used as sensing agent. As shown in FIG. 13A, a simple assay was performed by adding an analyte into this sensing solution to trigger an enzyme/cofactor reaction. Detection of a microRNA 21 (hsa-miR-21; SEQ ID NO: 11), a frequently upregulated miRNAs in solid tumors, such as breast cancer, was tested. As shown in FIG. 13B, a DNA toehold displacement (SEQ ID NO: 10) was designed to recognize the hsa-miR-21 sequence, which subsequently triggered the co-assembly of an enzyme/cofactor pair. As shown in FIGS. 13C and 13D, the activity of the G6PDH/NAD+ reaction was proportional to the added concentration of hsa-miR-21. A detection limit of about 1 nm miRNA was estimated based on the 3×SD criterion, where SD is the standard deviation of three reaction slopes for blank samples.

Figure 13F:
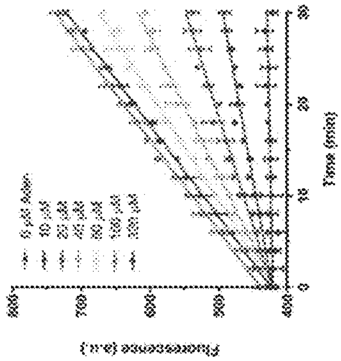
Figure 13G:
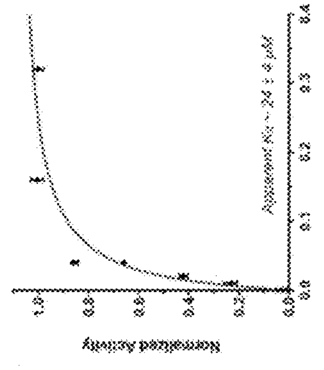

Alternatively, an aptamer switch can be incorporated into the DNA hairpin structure for responding to small molecules. As shown in FIG. 13E, adenosine aptamer (Ade-Apt) (SEQ ID NO: 14) was used to lock the hairpin structure with a stem region of a 11-bp aptamer-complement duplex. The adenosine-aptamer binding induced a conformational switch to trigger the coassembly of enzyme and cofactor, similarly as described in FIGS. 9 and 10. To facilitate the aptamer switch, a base strand was not used in this case. A titration curve showed that the activity of G6PDH/NAD+ pair increased corresponding to the concentration of adenosine from 0-320 μm (FIGS. 13F and 13G). The detection limit was estimated to be lower than 10 μm based on the definition of 3×SD. The apparent dissociation constant (Kd) of this aptamer lock was about 24±4 μm. Additionally, the sensitivity of the aptamer circuit can be tuned by increasing the stability of aptamer-hairpin hybridization. For example, the detection limit of adenosine was increased to about 400 μm by using a base strand to stabilize aptamer-hairpin hybridization, with an apparent Kd about 2.5±0.5 mm. This allows for engineering a series of sensors with tunable dynamic range for detecting targets from low-nanomolar to high-millimolar concentrations.

Example 8

DNA Hairpin Assembly-Mediated Actuation of Enzyme/Cofactor Pairs for Increasing the Detection Sensitivity In the above systems, one target molecule triggered the assembly of one enzyme/cofactor pair. To increase the signal production, a DNA hairpin assembly circuit was used to bring together multiple enzyme/cofactor pairs by one trigger molecule. As shown in FIG. 14A, a sensing circuit first releases a trigger strand upon recognizing a target. Then, the trigger strand induces the assembly of hairpins into either a long duplex by hybridization chain reaction (HCR) (Dirks et al., *Proc Nat Acad Sci* 2004, 101:15275-8), or produces many short duplexes by catalytic hairpin assembly (CHA) (Yin et al., *Nature* 2008, 451:318-22). The assembled hairpin structures are used to anchor multiple pairs of enzymes and cofactors. The gain of this signal production can be estimated by multiplying the assembled enzyme/cofactor pairs (Nhairpin assembly) and the boosted activity of an enzyme/cofactor pair (Fenzyme/cofactor).

Figure 15C:
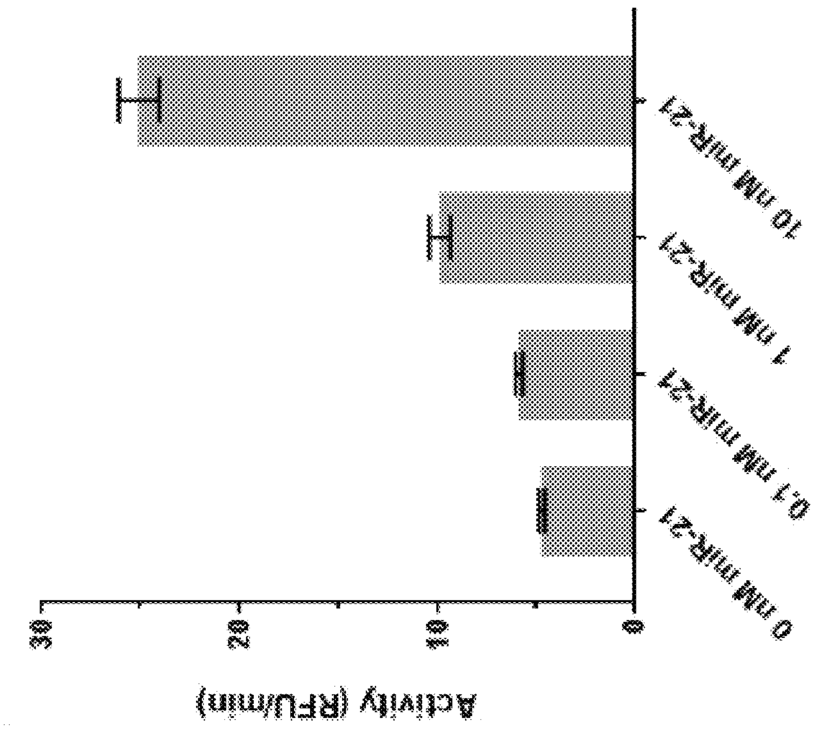
FIG. 15B-15C miR-21 detection using a CHA circuit-mediated assembly of enzyme/cofactor pairs. (B) Raw activity curves of titrating miR-21 concentration from 0 nM to 10 nM. (C) The measured enzyme activity (slope of curves) depending on the concentration of miR-21. Error bar: range of data from three replicates. Detailed assay condition: In Step-1, 10 nM sensor and 10 nM hairpin-locked catalyst were first thermally annealed separately. Then, the mixture of 10 nM sensor and 10 nM hairpin-locked catalyst were incubated with a solution of miR-21 for 30 mins at about 25° C. In Step-2, the reaction mixture of Step-1 was incubated with 100 nM CHA hairpins for three hours at about 25° C. Then, the solution was incubated with 100 nM locked NAD+ and 100 nM G6PDH for 30 mins at about 25° C. The enzyme activity was assayed in a substrate solution of 1 mM G6P, 500 μM PMS and 500 μM resazurin. All incubations and assays were performed in 1×TBS-Mg (pH about 7.4; 4 mM $MgCl_2$) buffer.
Figure 15B:
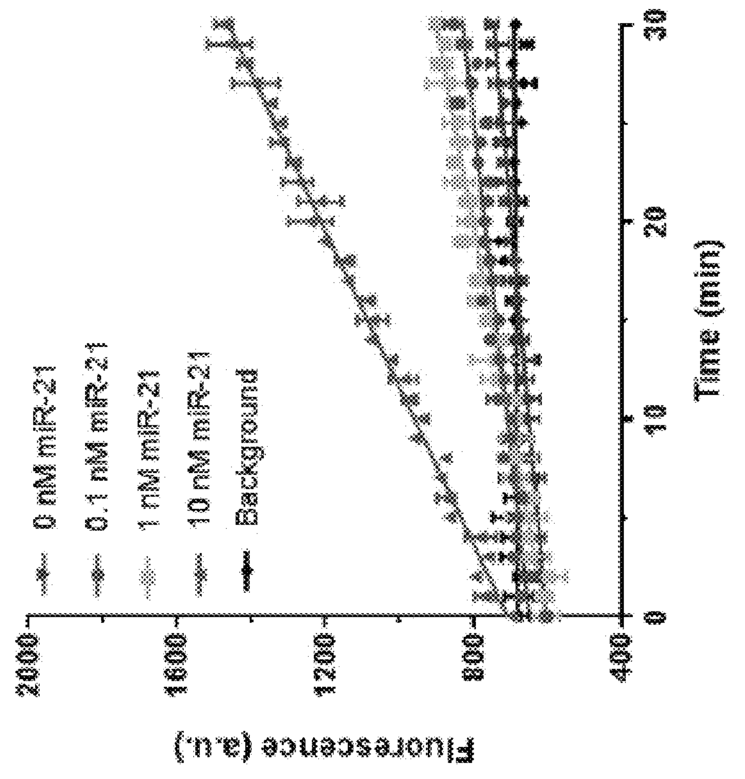

As shown in FIG. 14B, a CHA circuit (Jiang et al., *Angew. Chem. Int. Ed.* 2014, 53:1845-8*; Angew. Chem.* 2014, 126:1876-79) was used to produce short DNA duplexes displaying a probe (probe "a") for triggering the assembly of enzyme/cofactor pairs. As shown in FIG. 14C, native PAGE was used to characterize the CHA-produced short DNA duplexes by titrating the trigger strand from 0.1 nm to 100 nm. The band-shifts of DNA gel showed that almost all hairpins were assembled into short duplexes at 10 nm trigger strand. These CHA-produced duplexes were also validated to react with a toehold locked hairpin by Forster resonance energy transfer (FRET). The assembly of a locked hairpin and an enzyme-DNA strand was confirmed by increased Cy3-Cy5 FRET signals (FIG. 14C, right panel). As shown in FIG. 14D, the dependence of G6PDH/NAD+ reaction activity on the added trigger strands was tested. A nonspecific enzyme activity was observed at 0 nm trigger owing to the assembly leakage of CHA circuit. Increases of enzyme activity were detected for the trigger strand from 0.1 nm to 100 nm. Enzyme activity was close to the saturated activity when the trigger strand was higher than 10 nm. This result was consistent with the PAGE characterization in FIG. 14C. Using this CHA assembly circuit, w0.1 nm miR-21 was detected with a signal-to-noise ratio greater than 3 (FIGS. 15A-15C). This detection limit of this CHA assembly circuit was one magnitude lower than the single DNA-hairpin locked enzyme/cofactor pair (FIG. 13B).

In summary, a nanoscale molecular circuit was used to control the proximity assembly of enzyme/cofactor pairs. A DNA hairpin structure was used to lock a catalytic cofactor to inhibit the enzyme/cofactor reaction. The targeted molecular inputs could trigger the opening of the DNA lock with the subsequent assembly of an enzyme/cofactor pair for actuating a biochemical reaction to produce detectable signals. It is also possible to use DNAzymes to replace the enzyme/cofactor for producing signals. The DNA proximity assembly circuit only consisted of a few ssDNA strands and could be engineered to detect various molecular targets (Oh et al., *Angew. Chem.* 2018, 13:13270-4).

Example 9

Materials and Methods

This example describes the materials and method used for Examples 1-8.

1.1 Chemicals and Materials

40% Acrylamide/Bis solution (19:1, A-Stock) was from Bio-Rad. Water (DNA Grade For DNA Work), tris base, HEPES (4-(2-hydroxyethyl)-1-piperazineethanesulfonic acid), ethylenediamine tetraacetic acid (EDTA), magnesium acetate tetrahydrate (MgAc), magnesium chloride (MgCl), ammonium persulfate (APS), boric acid, urea, 10×TBS (Tris Buffered Saline), triethylamine acetate (TEAA), SPDP (succinimidyl 3-(2-pyridyldithio)propionate), DSS (disuccinimidyl suberate), tetramethylethyl-enediamine (TEMED), N,N-diisopropylethylamine (DIPEA), GeneRuler Low Range DNA Ladder, SYBRTM Green I Nucleic Acid Gel Stain—10,000× concentrate in DMSO, Amplex Red, hydrogen peroxide (H2O2), Tris(2-carboxyethyl)phosphine hydrochloride (T-CEP) and ethidium bromide (EB) were purchased from Fisher Scientific. Acetic acid was from Acros Organics. Adenosine, bromophenol blue tracking dye, hexokinase from *Saccharomyces cerevisiae*, acetate kinase, glucose-6-phosphate (G6P), resazurin, phenazine methosulfate (PMS), and DEAE-Sepharose resin were purchased from Sigma. β-Nicotinamide-N6-(2-aminoethyl) adenine dinucleotide (6-AE-NAD+) was purchased from BIOLOG Life Science Institute. Distilled water (DI water) was from local grocery stores. Hemin (porcine), 97+% was purchased from Alfa Aesar. N6-(6-Amino)hexyl-ATP was from Axxora. Cyanine3 NHS ester and Cyanine5 NHS ester were purchased from Lumiprobe. Glucose 6-phosphate dehydrogenase (G6PDH) was purchased from Worthington. denosine powder was dissolved in distilled water to make a stock concentration of 10 mM. All oligonucleotides were from Integrated DNA Technologies (IDT).

1.2. Preparation of Buffer

10×TAE-MgAc stock buffer (pH 8.5) was prepared as previously described, 1 which was composed of: 0.4 M Tris Base, 0.2 M Acetic Acid, 0.02 M EDTA, and 125 mM magnesium acetate. In the preparation of DNA assembly, 10×TAE-MgAc buffer was diluted to 1×TAE-MgAc (12.5 mM) buffer. For aptamer and CHA, 10×TBS-$MgCl_2$ (pH 7.5) stock buffers were prepared, which was composed of: 250 mM Tris Base and 40 mM magnesium chloride. In the preparation of aptamer and CHA structures, 10×TBS-$MgCl_2$ buffer was diluted to 1×TBS-MgCl2 (4 mM) buffer.

1.3 Purification of DNA Strands and Quantification of DNA Concentration

8% denaturing PAGE was used to purify DNA strands ordered from IDT. DNA concentrations were quantified using a Nanodrop (Thermo Scientific) at 260 nm. The purified DNA strands were stored at −20° C. in DNA grade water.

1.4. Anneal DNA Structures

DNA nanostructures were assembled by using a thermal-annealing program of a PCR Thermocycler (Eppendorf). The annealing of DNA starts at 80° C. for 1 min, followed by a series of cooling steps to 1° C. as:

| Temperature | Time |
|---|---|
| 80° C. | 1 min |
| 78° C. | 1 min |
| 76° C. | 2 mins |
| 72° C. | 2 mins |
| 68° C. | 5 mins |
| 64° C. | 5 mins |
| 60° C. | 5 mins |
| 56° C. | 5 mins |
| 52° C. | 5 mins |
| 48° C. | 5 mins |
| 44° C. | 5 mins |
| 40° C. | 5 mins |
| 36° C. | 5 mins |
| 32° C. | 5 mins |
| 28° C. | 5 mins |
| 24° C. | 5 mins |
| 15° C. | hold |

1.5. Native PAGE Characterization of DNA Structures

5% Native PAGE gels were prepared at room temperature and were left to polymerize for 3 hours. After loading the samples and a low-range DNA ladder, the gel ran for 2.5 to 3 hours at a constant voltage of 200 V. Then, the gel was stained with Ethidium Bromide for 5 minutes or SYBRTM Green I for 20 minutes and rinsed in DI water for another 5 minutes. The gel was imaged using a UVP ChemiDoc-It2 Imager instrument. For DNA toehold displacement circuit, 1×TAE 12.5 mM $Mg^{2+}$ was loaded into the upper chamber for maintaining the same $Mg^{2+}$ concentration during the gel electrophoresis. For aptamer circuits, 1×TAE buffer was loaded into the upper chamber.

1.6. Conjugation of Cofactor and Dye to Oligonucleotide

NAD or ATP analogue was conjugated to an aminomodified hairpin strand using a DSS linker. An amino-modified NAD analogue was conjugated to a 5' amine-modified oligonucleotide by a disuccinimidyl suberate (DSS) linker on anion-exchange DEAE-Sepharose resin. After conjugation, High Performance Liquid Chromatography (HPLC, Agilent 1260 series) was used for purifying NAD+-modified oligonucleotides with an elution gradient from 25% (vol/vol) methanol/100 mM TEAA to 35% (vol/vol) methanol/100 mM TEAA. The flow rate should be set at 1.0 mL/min. The collected fractions of sample peak was characterized by mass spectrometry, lyophilized (freeze-dried), and rehydrated using DNA grade water.

For the dye-labelled oligonucleotide, NHS-Cy3 or NHS-Cy5 was first reacted with amine-modified DNA in 50 mM HEPES buffer (pH 8.5) for one hour in the dark. Then, the reaction solution was filtrated with DNA grade water by using an Amicon molecular weight cut-off filter for three times. The purified dye-labelled DNA was stored at −20° C.

1.7. Conjugation of Enzyme to DNA

Thiol-modified DNA is three times more expensive than amine-modified DNA if they are purchased commercially. Thus, a protocol to convert amine-modified DNA to thiol-modified DNA by SPDP chemistry was developed. Briefly, 1000 μL, 200 μM amine-modified DNA is first reacted with SPDP (20× excess) in 50 mM HEPES (pH 8.5) for one hour. Then, excess SPDP is removed by the filtration with 50 mM HEPES (pH 7.5) using an Amicon Molecular Weight cut-off filter for three times. SPDP-modified DNA is treated with T-CEP (20× excess) in 50 mM HEPES (pH 7.5) buffer for one hour. The thiol-modification yield can be estimated by the increased absorbance at 343 nm due to the production of pyridine 2-thione. Excess T-CEP and pyridine 2-thione are removed by the filtration with DNA Grade water using an Amicon Molecular Weight cut-off filter for three times. The purified thiol-modified DNA is quantified for concentration and is stored at −20° C.

A SPDP cross-linking chemistry was used for attaching oligonucleotides to proteins. SPDP first reacts with lysine residues on the protein surface in 50 mM HEPES (pH 8.5), followed by the activation of the pyridyl disulfide group to facilitate a disulfide bond exchange with thiol-modified DNA. After conjugation, the reaction mixture was first washed using Amicon molecular weight cut-off filter with two times of 50 mM HEPES and 1.5 M NaCl (pH 7.5), and two times of 50 mM HEPES (pH 7.5). Then, anion-exchange HPLC was used for purifying enzyme-DNA conjugates with an elution gradient from 25% (vol/vol) solvent B to 70% (vol/vol) solvent B. The flow rate should be set at 1.0 mL/min. Solvent A: 50 mM HEPES (pH 7.5); Solvent B: 50 mM HEPES+1 M NaCl (pH 7.5). The collected fractions were analyzed by UV absorbance at 260 nm and 280 nm.

1.8. Enzyme/Cofactor Assay

A simple catalytic system includes glucose 6-phosphate dehydrogenase (G6PDH) and its corresponding NAD+ cofactor. 4 G6PDH (homodimeric, ~100 kDa) catalyzes the oxidation of glucose 6-phosphate to 6-phosphogluconolactone, while concurrently reducing NAD+ to NADH with a turnover rate of about 700 $s^{-1}$. G6PDH is a commercially available enzyme with large quantity production, lower cost and good stability. The actuated G6PDH/NAD+ pair can catalyze a coupled assay of PMS (phenazine methosulfate) and resazurin, which converts resazurin to strongly fluorescent resorufin (excitation max about 544 nm, emission max about 590 nm). The assay is also visible with the color change from blue (resazurin) to pink (resorufin). 6 The assay was performed by first adding 100 nM DNA hairpin-locked cofactor and 100 nM enzyme-II' conjugate into 1×TBS-Mg (pH about 7.4; 4 mM $MgCl_2$) buffer, followed by the addition of the trigger DNA-I'. The mixture was incubated for 30 minutes at room temperature (about 25° C.) in the dark. Then, the solution was mixed with the substrate solution of 1 mM G6P, 500 μM PMS, and 500 μM resazurin in pH 7.5, 1×TBS-Mg buffer. The enzyme/cofactor reaction was monitored by fluorescence for up to one hour using a Cytation 3 plate reader (Biotek, Winooski, Vt.) with 532-nm excitation and 590-nm emission. The activity of enzyme solution was determined by fitting the initial velocity of the reaction curves where the slope of the curve is a straight line prior to the reaction reaching equilibrium. All reactions were carried out in a 96-well black plate with at least three replicates.

The hexokinase (HEK)/ATP pair was assayed by a coupled reaction. HEK first uses ATP to convert glucose to glucose-6-phosphate (G6P). Then, the enzyme G6PDH oxidizes G6P to produce NADH. The production of NADH is measured by a fluorescent PMS/resazurin as described above. Acetate kinase (AK) is also added to cycle ADP back to ATP for the continuous reaction of HEK/ATP pair. The assay is similar to that for G6PDH/NAD+ pair except for the substrate solution of 1 mM glucose, 1 mM acetyl phosphate, 100 nM AK, 100 nM G6PDH, 1 mM NAD+ and 500 μM of PMS and resazurin. The assembly of G-quadruplex/hemin reaction was performed by first assembling a 150 nM DNA hairpin-locked G-quadruplex halve from G-halve-hairpin and TH (toehold strand) in 1×TBS-Mg—K (pH ~7.5; 4 mM MgCl2, 20 mM KCl) buffer. Then, a trigger DNA was added into the solution to open the hairpin by strand displacement. The full G-quadruplex structure was subsequently assembled by adding 150 nM G-halve-II and 37.5 nM hemin. The mixture was incubated for 30 minutes at room temperature in the dark. The activity of the solution was measured by adding a substrate solution of 100 μM $H_2O_2$ and 100 μM Amplex-Red in 1×TBS—Mg-Kbuffer. The reaction was monitored by fluorescence with 532-nm excitation and 590-nm emission.

1.9. CHA Circuit-Mediated Assembly of Enzyme/Cofactor Pairs

CHA strands were prepared in 1×TBS buffer (pH 7.4) with the pre-incubation on the PCR thermocycler at 95° C. for 5 minutes and cooled down to 25° C. by 6° C./min. DNA hairpin-locked NAD+ was prepared in 1×TBS-12.5 mM $MgCl_2$ buffer, and was incubated on the PCR thermocycler using an annealing program.

Detailed assay condition: The trigger strand was first incubated with 100 nM CHA hairpins for three hours at about 25° C. Then, the CHA solution was incubated with 100 nM locked NAD+ and 100 nM G6PDH for 30 mins at about 25° C. The enzyme activity was assayed in a substrate solution of 1 mM G6P, 500 μM PMS and 500 μM resazurin. All incubations and assays were performed in 1×TBS-Mg (pH about 7.4; 4 mM $MgCl_2$) buffer.

Example 10

Aptamer Switch-Regulated Substrate Cooperative Activation

In some examples the sensor of the present application includes allosteric feedback control (e.g., DNA logic gate), which can allow for the identification of a molecule with a desired functions.

A specific example of such a sensor is shown in FIG. 16B, which uses ATP-feedback activation of hexokinase (HEK). HEK uses ATP to phosphorylate glucose, to produce glucose-6-phosphate, which can be detected by G6PDH with NADH production. The enzyme HEK and an inhibitor AppNHP ((2'/3'-O-(2-Aminoethyl-carbamoyl)-Adenosine-5'-[(β, γ)-imido] triphosphate) are assembled on a dsDNA scaffold with the proximity-enhanced inhibition of the enzyme activity. The hybrid protein/DNA duplex structures comprise an aptamer (orange) binding to a ATP molecule. AppNHp is a broad-spectrum kinase inhibitor with a structure resembling ATP except for a non-hydrolysable phosphate bond. This analogue can be conjugated to amine-modified DNA using disuccinimidyl suberate (DSS) chemistry as described herein. In the presence of ATP molecules, the ATP-binding aptamer switch will disrupt the hybridization of HEK with AppNHP, releasing an active HEK for phosphorylating glucose and producing NADH in a HEK-G6PDH cascade. As shown in the Hill equation below, $$\frac{d[P]}{dt} = \frac{V_{max}[S]^n}{K_m + [S]^n}$$

the substrate feedback activation can be analyzed by fitting the Hill coefficient (n) of a reaction kinetics. Positive substrate cooperativity will show a sigmoidal curve (n>1) of velocity versus substrate concentration.

In one example the sensor includes the following sequences:

| Sample | DNA Sequence (SEQ ID NO:) | # Bases |
|---|---|---|
| Nucleic Acid-1 (comprised of an Aptamer (underlined; here adenosine aptamer) and a 5'-linked inhibitor, suchas AppNHP) | 5'-Inhibitor-TTTTTTTTTTTTTT TTTTTT GAG AAC CTG GGG GAG TAT TGC GGA GGA AGG T (28) | 51 |
| Nucleic Acid-2 (linked with an enzyme) | 5'-CC CAG GTT CTC TTTTT-enzyme (29) | 24 |

To engineer the product feedback inhibition, an aptamer-locked hairpin can be used to lock an AppNHP analogue with no inhibition of an ADK (Adenylate kinase) enzyme (FIG. 16C). An enzyme, such as ADK, can convert ADP to ATP and AMP. As ATP accumulates in the ADK-catalyzed reaction, it will bind to the aptamer lock and disrupt the locked the structure to release an AppNHP. The subsequent assembly of ADK and AppNHP will inhibit the enzyme activity. Thus, this competitive assay uses an enzyme inhibitor and the enzyme.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A sensor, comprising:

(a) a trigger module, comprising (i) a first nucleic acid molecule, comprising a first portion specific for a target, a second portion, and a third portion, (ii) a second nucleic acid molecule comprising a terminal cofactor, a first stem portion, a loop portion, a second stem portion, a third stem portion, and a fourth portion, wherein the first stem portion includes the terminal cofactor and is complementary to the second stem portion, thereby resulting in hybridization between the first stem portion and the second stem portion, thereby producing the loop potion, wherein the third stem portion is complementary to the second portion of the first nucleic acid molecule, thereby resulting in hybridization between the third stem portion and the second portion of the first nucleic acid molecule, (iii) a third nucleic acid molecule, comprising a first portion and second portion, wherein the first portion of the third nucleic acid molecule is complementary to the third portion of the first nucleic acid molecule thereby resulting in hybridization between the first portion of the third nucleic acid molecule and the third portion of the first nucleic acid molecule, wherein the second portion of the third nucleic acid molecule is complementary to the fourth portion of the second nucleic acid molecule thereby resulting in hybridization between the second portion of the third nucleic acid molecule and the fourth portion of the second nucleic acid molecule, wherein hybridization between nucleotides of the first and second nucleic acid molecules, first and third nucleic acid molecules, and second and third nucleic acid molecules, forms the trigger module, (b) sensory module, comprising (i) a fourth nucleic acid molecule comprising a nucleic acid strand; and (ii) an enzyme, wherein the nucleic acid strand of the fourth nucleic acid molecule is complementary to the second and third stem portion of the second nucleic acid molecule, and wherein the enzyme is activated by the cofactor.

2. The sensor of claim 1, wherein the first nucleic acid molecule, the second nucleic acid molecule, the third nucleic acid molecule, and the fourth nucleic acid molecule are DNA.

3. The sensor of claim 1, wherein first portion specific for the target of the first nucleic acid molecule comprises a nucleic acid sequence complementary to a nucleic acid target.

4. The sensor of claim 3, wherein the nucleic acid target is DNA or RNA.

5. The sensor of claim 4, wherein the RNA is mRNA or miRNA.

6. The sensor of claim 3, wherein the nucleic acid target is a cancer-specific nucleic acid molecule or infectious disease-specific nucleic acid molecule.

7. The sensor of claim 6, wherein the cancer-specific nucleic acid molecule comprises miR-21.

8. The sensor of claim 1, wherein the first portion specific for the target of the first nucleic acid molecule comprises a nucleic acid specific for a small molecule target.

9. The sensor of claim 8, wherein the first portion specific for the target of the first nucleic acid molecule comprises an aptamer, aptazyme, or DNAzyme.

10. The sensor of claim 1, wherein the cofactor comprises NAD and the enzyme comprises glucose-6-phosphate dihydrogenase (G6PHD).

11. A composition, comprising a) the sensor of claim 1, and water, saline, or a liquid buffer, b) the sensor of claim 1, and a buffer comprising phosphate, Tris saline, HEPEss, or combinations thereof, c) the sensor of claim 1 immobilized on a solid support, or d) the sensor of claim 1 immobilized on paper.

12. A kit comprising the sensor of claim 1, wherein the fourth nucleic acid molecule comprising a nucleic acid strand and an enzyme is optionally in a container separate from the trigger module.

13. The kit of claim 12, further comprising a color detection reagent.

14. A method of detecting a target agent, comprising:

contacting a sample with the sensor of claim 1, under conditions that permit the target agent to bind to the first nucleic acid portion specific for the target of the first nucleic acid molecule, thereby displacing the first nucleic acid molecule from the second nucleic acid molecule, and that permit the fourth nucleic acid molecule to hybridize to the first and second stem portion of the second nucleic acid molecule;

allowing the cofactor to activate the enzyme;

allowing the activated enzyme to interact with one or more reagents to produce a visual signal; and detecting the visual signal, wherein the production of a visual signal indicates the presence of the target agent in the sample.

15. The method of claim 14, wherein the sample is a biological, organic, or environmental sample.

16. The method of claim 14, wherein the visual signal is a color or fluorescent signal.

17. The method of claim 14, wherein the one or more reagents comprise phenazine methosulfate and resazurin, wherein the visual signal is pink color.

18. The method of claim 14, wherein detecting the visual signal comprises detection by eye.

19. The method of claim 14, wherein the method further comprises performing hybridization chain reaction (HCR), DNA hairpin assembly, or both.

20. The sensor of claim 13, wherein the color detection reagent comprises one or more of glucose-6-phosphate, phenazine methosulfate, resazurin, amplex red, and $H_2O_2$.

21. The sensor of claim 1, wherein:

a) the cofactor comprises $Cu^+$ and the enzyme comprises cytochrome oxidase;

b) the cofactor comprises ferrous or ferric and the enzyme comprises catalase, cytochrome, nitrogenase, or hydrogenase;

c) the cofactor comprises $Mg2^+$ and the enzyme comprises glucose 6-phosphase, hexokinase, or DNA polymerase;

d) the cofactor comprises $Mn2^+$ and the enzyme comprises arginase;

e) the cofactor comprises olybdenum and the enzyme comprises nitrate reductase or nitrogenase;

f) the cofactor comprises nickel and the enzyme comprises urease;

g) the cofactor comprises zinc and the enzyme comprises alcohol dehydrogenase, carbonic anhydrase, or DNA polymerase;

h) the cofactor comprises thiamine pyrophosphate and the enzyme comprises pyruvate dehydrogenase;

i) the cofactor comprises NAD and the enzyme comprises glucose-6-phosphate dehydrogenase or lactate dehydrogenase;

j) the cofactor comprises pyridoxal phosphate and the enzyme comprises aminotransferease;

k) the cofactor comprises methylcobalamin and the enzyme comprises a vitamin B12-dependent enzyme;

l) the cofactor comprises cobalamine and the enzyme comprises methyltransferase;

m) the cofactor comprises biotin and the enzyme comprises a streptavidin-fused enzyme;

n) the cofactor comprises coenzyme A and the enzyme comprises pyruvate dehydrogenase;

o) the cofactor comprises tetrahydrofolic acid and the enzyme comprises dihydrofolate reductase;

p) the cofactor comprises menaquinone and the enzyme comprises y-glutamyl carboxylase;

q) the cofactor comprises ascorbic acid and the enzyme comprises ascorbate peroxidase;

r) the cofactor comprises a flavin adenine dinucleotide and the enzyme comprises glucose oxidase or glucose dehydrogenase;

s) the cofactor comprises a flavin mononucleotide and the enzyme comprises diaphorase;

t) the cofactor comprises coenzyme F420 and the enzyme comprises coenzyme F420 hydrogenase;

u) the cofactor comprises adenosine triphosphate and the enzyme comprises hexokinase, pyruvate kinase, or acetate kinase;

v) the cofactor comprises S-adenosyl methionine and the enzyme comprises radical SAM enzymes;

w) the cofactor comprises coenzyme B and the enzyme comprises enzyme methyl coenzyme M reductase;

x) the cofactor comprises coenzyme M and the enzyme comprises enzyme methyl-coenzyme M reductase;

y) the cofactor comprises cytidine triphosphate and the enzyme comprises aspartate carbamoyltransferase;

z) the cofactor comprises glutathione and the enzyme comprises glutathione reductase;

a2) the cofactor comprises heme and the enzyme comprises horseradish peroxidase or DNA G-quadruplex;

b2) the cofactor comprises lipoamide and the enzyme comprises dihydrolipoyl transacetylase;

c2) the cofactor comprises methanofuran and the enzyme comprises formyltransferase;

d2) the cofactor comprises molybdopterin and the enzyme comprises xanthine oxidase, DMSO reductase, sulfite oxidase, or nitrate reductase;

e2) the cofactor comprises 3'-phosphoadenosine-5'-phosphosulfate and the enzyme comprises adenylyl-sulfate kinase;

f2) the cofactor comprises pyrroloquinoline quinone and the enzyme comprises quinoprotein glucose dehydrogenase; or g2) the cofactor comprises tetrahydrobiopterin and the enzyme comprises tryptophan hydroxylase.

* * * * *

SEQUENCE LISTING

<160> NUMBER OF SEQ ID NOS: 29

<210> SEQ ID NO 1
<211> LENGTH: 46
<212> TYPE: DNA
<213> ORGANISM: Artificial Sequence
<220> FEATURE:
<223> OTHER INFORMATION: hairpin II in FIG. 9A

<400> SEQUENCE: 1
accagccgtt ttttcggctg gtgacggctc cttggcgccg gctttc 46

<210> SEQ ID NO 2
<211> LENGTH: 28
<212> TYPE: DNA
<213> ORGANISM: Artificial Sequence
<220> FEATURE:
<223> OTHER INFORMATION: toehold I in FIG. 9A

<400> SEQUENCE: 2
gtgcgaattg gagccgtcgt tggtgtgc 28

<210> SEQ ID NO 3
<211> LENGTH: 27
<212> TYPE: DNA
<213> ORGANISM: Artificial Sequence
<220> FEATURE:
<223> OTHER INFORMATION: base III in FIGS. 9A and 13B

<400> SEQUENCE: 3
tttagaaagc cggcgccttc gcacttt 27

<210> SEQ ID NO 4
<211> LENGTH: 19
<212> TYPE: DNA
<213> ORGANISM: Artificial Sequence
<220> FEATURE:
<223> OTHER INFORMATION: trigger-I' in FIG. 9A

<400> SEQUENCE: 4
gcacaccaac gacggctcc 19

<210> SEQ ID NO 5
<211> LENGTH: 20
<212> TYPE: DNA
<213> ORGANISM: Artificial Sequence
<220> FEATURE:

<223> OTHER INFORMATION: enzyme DNA II' in FIG. 9A

<400> SEQUENCE: 5
agccgtcacc agccgttttt 20

<210> SEQ ID NO 6
<211> LENGTH: 41
<212> TYPE: DNA
<213> ORGANISM: Artificial Sequence
<220> FEATURE:
<223> OTHER INFORMATION: G-halve-hairpin in FIG. 9A

<400> SEQUENCE: 6
tgggtagggc gggttttcct acccaccttg tcatagagca c 41

<210> SEQ ID NO 7
<211> LENGTH: 45
<212> TYPE: DNA
<213> ORGANISM: Artificial Sequence
<220> FEATURE:
<223> OTHER INFORMATION: G-halve-II' in FIG. 9A

<400> SEQUENCE: 7
gtgctctatg acaaggaccc atgggtaggt tttgggtcct tgtca 45

<210> SEQ ID NO 8
<211> LENGTH: 20
<212> TYPE: DNA
<213> ORGANISM: Artificial Sequence
<220> FEATURE:
<223> OTHER INFORMATION: complimentary of II' in FIG. 9A

<400> SEQUENCE: 8
aaaaacggct ggtgacggct 20

<210> SEQ ID NO 9
<211> LENGTH: 49
<212> TYPE: DNA
<213> ORGANISM: Artificial Sequence
<220> FEATURE:
<223> OTHER INFORMATION: hairpin II in FIG. 13B

<400> SEQUENCE: 9
accagccgtt ttttcggctg gtgactgatg ttgattggcg ccggctttc 49

<210> SEQ ID NO 10
<211> LENGTH: 31
<212> TYPE: DNA
<213> ORGANISM: Artificial Sequence
<220> FEATURE:
<223> OTHER INFORMATION: toehold I in FIG. 13B

<400> SEQUENCE: 10
gtgcgaattt caacatcagt ctgataagct a 31

<210> SEQ ID NO 11
<211> LENGTH: 22
<212> TYPE: RNA
<213> ORGANISM: Homo sapiens

<400> SEQUENCE: 11
uagcuuauca gacugauguu ga 22

<210> SEQ ID NO 12
<211> LENGTH: 23

<212> TYPE: DNA
<213> ORGANISM: Artificial Sequence
<220> FEATURE:
<223> OTHER INFORMATION: enzyme DNA II' in FIG. 13B

<400> SEQUENCE: 12
aacatcagtc accagccgtt ttt 23

<210> SEQ ID NO 13
<211> LENGTH: 48
<212> TYPE: DNA
<213> ORGANISM: Artificial Sequence
<220> FEATURE:
<223> OTHER INFORMATION: hairpin II in FIG. 13E

<400> SEQUENCE: 13
accagccgtt ttttcggctg gtcccaggtt ctcttggcgc cggctttc 48

<210> SEQ ID NO 14
<211> LENGTH: 40
<212> TYPE: DNA
<213> ORGANISM: Artificial Sequence
<220> FEATURE:
<223> OTHER INFORMATION: adenosine aptamer

<400> SEQUENCE: 14
gtgcgaattg agaacctggg ggagtattgc ggaggaaggt 40

<210> SEQ ID NO 15
<211> LENGTH: 24
<212> TYPE: DNA
<213> ORGANISM: Artificial Sequence
<220> FEATURE:
<223> OTHER INFORMATION: enzyme DNA II' in FIG. 13E

<400> SEQUENCE: 15
gagaacctgg gaccagccgt tttt 24

<210> SEQ ID NO 16
<211> LENGTH: 56
<212> TYPE: DNA
<213> ORGANISM: Artificial Sequence
<220> FEATURE:
<223> OTHER INFORMATION: hairpin CH-1 in FIGS. 14B and 15A

<400> SEQUENCE: 16
agaggcatca atgggaatgg gatcatgcct ctaacctagc gatcccattc ccattg 56

<210> SEQ ID NO 17
<211> LENGTH: 72
<212> TYPE: DNA
<213> ORGANISM: Artificial Sequence
<220> FEATURE:
<223> OTHER INFORMATION: hairpin CH-2 in FIGS. 14B and 15A

<400> SEQUENCE: 17
atgggatcgc taggttagag gcatgatccc attcccaaac atgcctctaa cctagccctt 60
gtcatagagc ac 72

<210> SEQ ID NO 18
<211> LENGTH: 24
<212> TYPE: DNA
<213> ORGANISM: Artificial Sequence
<220> FEATURE:
<223> OTHER INFORMATION: trigger sequence -continued

<400> SEQUENCE: 18
gatcccattc ccattgatgc ctct 24

<210> SEQ ID NO 19
<211> LENGTH: 41
<212> TYPE: DNA
<213> ORGANISM: Artificial Sequence
<220> FEATURE:
<223> OTHER INFORMATION: hairpin-cofactor in FIGS. 14B and 15A

<400> SEQUENCE: 19
taccagccgt tttttttcgg ctggtccttg tcatagagca c 41

<210> SEQ ID NO 20
<211> LENGTH: 24
<212> TYPE: DNA
<213> ORGANISM: Artificial Sequence
<220> FEATURE:
<223> OTHER INFORMATION: toehold a* in FIGS. 14B and 15A

<400> SEQUENCE: 20
gtgctctatg acaagggcta ggtt 24

<210> SEQ ID NO 21
<211> LENGTH: 19
<212> TYPE: DNA
<213> ORGANISM: Artificial Sequence
<220> FEATURE:
<223> OTHER INFORMATION: enzyme-DNA in FIGS. 14B and 15A

<400> SEQUENCE: 21
tgacaaggac cagcttttt 19

<210> SEQ ID NO 22
<211> LENGTH: 22
<212> TYPE: DNA
<213> ORGANISM: Artificial Sequence
<220> FEATURE:
<223> OTHER INFORMATION: sensor (purple) in FIG. 15A

<400> SEQUENCE: 22
atgcctctta gcttatcaga ct 22

<210> SEQ ID NO 23
<211> LENGTH: 22
<212> TYPE: DNA
<213> ORGANISM: Artificial Sequence
<220> FEATURE:
<223> OTHER INFORMATION: sensor (red) in FIG. 15A

<400> SEQUENCE: 23
tcaacatcag tctgataagc ta 22

<210> SEQ ID NO 24
<211> LENGTH: 52
<212> TYPE: DNA
<213> ORGANISM: Artificial Sequence
<220> FEATURE:
<223> OTHER INFORMATION: hairpin-locked catalyst in FIG. 15A

<400> SEQUENCE: 24
agtctgataa gctaagaggc atgatcccat tcccattgat gcctcttagc tt 52

<210> SEQ ID NO 25
<211> LENGTH: 22

-continued

```
<212> TYPE: RNA
<213> ORGANISM: Homo sapiens

<400> SEQUENCE: 25

uaacacuguc ugguaaagau gg                                           22


<210> SEQ ID NO 26
<211> LENGTH: 22
<212> TYPE: RNA
<213> ORGANISM: Homo sapiens

<400> SEQUENCE: 26

uuuguucguu cggcucgcgu ga                                           22


<210> SEQ ID NO 27
<211> LENGTH: 26
<212> TYPE: DNA
<213> ORGANISM: Homo sapiens

<400> SEQUENCE: 27

gtcaagatca cagattttgg gcgggc                                       26


<210> SEQ ID NO 28
<211> LENGTH: 51
<212> TYPE: DNA
<213> ORGANISM: Artificial Sequence
<220> FEATURE:
<223> OTHER INFORMATION: strand comprising an adenosine aptamer and a
      5'-AppNHP in FIG. 16

<400> SEQUENCE: 28

tttttttttt tttttttttt gagaacctgg gggagtattg cggaggaagg t           51


<210> SEQ ID NO 29
<211> LENGTH: 16
<212> TYPE: DNA
<213> ORGANISM: Artificial Sequence
<220> FEATURE:
<223> OTHER INFORMATION: nucleic acid linked to enzyme in FIG. 16

<400> SEQUENCE: 29

cccaggttct cttttt                                                  16
```